(12) United States Patent
Guedat et al.

(10) Patent No.: US 7,723,358 B2
(45) Date of Patent: May 25, 2010

(54) AROYL-O-PIPERIDINE DERIVATIVES FOR THE TREATMENT OF DIABETES-RELATED PROBLEMS

(75) Inventors: Philippe Guedat, Montenois (FR); Francois Collonges, Beynost (FR); Olivier Chevreuil, Condeissat (FR); Hervé Dumas, Vaulx-Milieu (FR); Marie Noelle Denault, Ste Anne de Gervonde (FR); Stéphane Yvon, Ste Foy les Lyons (FR); Peter Kane, Cornwall (GB); Julia Lainton, Cornwall (GB); Avril Robertson, Cornwall (GB); Bernd Wendt, Weil (DE)

(73) Assignee: Merck Patent GmbH, Darmstadt (DE)

( * ) Notice: Subject to any disclaimer, the term of this patent is extended or adjusted under 35 U.S.C. 154(b) by 128 days.

(21) Appl. No.: 11/629,176

(22) PCT Filed: May 19, 2005

(86) PCT No.: PCT/EP2005/005440

§ 371 (c)(1),
(2), (4) Date: Dec. 11, 2006

(87) PCT Pub. No.: WO2005/121091

PCT Pub. Date: Dec. 22, 2005

(65) Prior Publication Data

US 2007/0254919 A1    Nov. 1, 2007

(30) Foreign Application Priority Data

Jun. 11, 2004   (EP) .................................. 0406345

(51) Int. Cl.
*A01N 43/40*    (2006.01)
*A61K 31/445*   (2006.01)

(52) U.S. Cl. ...................... 514/317; 546/290; 514/277; 514/315; 514/183

(58) Field of Classification Search ................. 514/183
See application file for complete search history.

(56) References Cited

U.S. PATENT DOCUMENTS

| 2002/0032238 A1 | 3/2002 | Priepke |
| 2004/0034028 A1 | 2/2004 | Guevel |
| 2004/0102490 A1 | 5/2004 | Meerpoel et al. |

OTHER PUBLICATIONS

Richard J. Lewis, Sr., Hawley's Condensed Chemical Dictionary, Fourteenth Edition, 2001, 3 pages.

*Primary Examiner*—James D Anderson
*Assistant Examiner*—Meghan Finn
(74) *Attorney, Agent, or Firm*—Millen, White, Zelano, Branigan, P.C.

(57) ABSTRACT

The present invention relates to derivatives of aroyl-O-piperidine structure of the general formula (I): in which $R^1$, $R^2$, $R^3$ and $R^4$ are as defined in the description. Application of the compounds of the formula (I) to the treatment of hypertriglyceridaemia, hypercholesterolaemia and dyslipidaemia, and to the prevention or treatment of obesity.

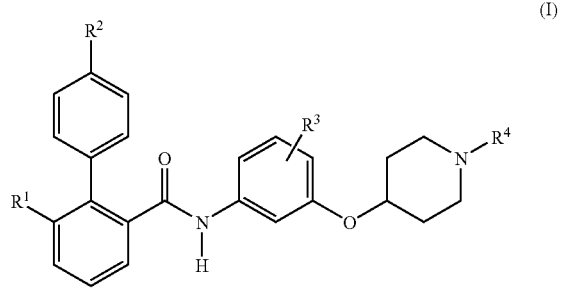

28 Claims, No Drawings

AROYL-O-PIPERIDINE DERIVATIVES FOR THE TREATMENT OF DIABETES-RELATED PROBLEMS

The invention relates to compounds that are inhibitors of microsomal triglyceride transfer protein (MTP), to pharmaceutical compositions comprising them, and to the use thereof in medicine.

MTP (microsomal triglyceride transfer protein) is a transfer protein located in the reticulum of hepatocytes and enterocytes, which catalyses the assembly of biomolecules that transport triglycerides, the apo B lipoproteins.

The term apo B more particularly denotes apoprotein 48 of the intestine and apoprotein 100 of the liver.

Mutations in MTP or in the B apoproteins are reflected in man by very low levels or even an absence of apo B lipoproteins. The lipoproteins containing apo B (chylomicrons, Very Low Density Lipoproteins) and their metabolic residues (chylomicron remnants, Low Density Lipoproteins) are recognised as being a major risk factor in the development of atherosclerosis, a major cause of death in industrialized countries. It is observed that, in individuals who are heterozygous for these mutations, levels reduced on average by a half are associated with a low cardiovascular risk (C. J. Glueck, P. S. Gartside, M. J. Mellies, P. M. Steiner, *Trans. Assoc. Am. Physicians*, 90, 184 (1977)). This suggests that modulation of the secretions of triglyceride-rich lipoproteins by means of MTP antagonists and/or of secretion of apo B might be useful in the treatment of atherosclerosis and more broadly of pathologies characterised by an increase in apo B lipoproteins.

Molecules that inhibit MTP and/or the secretion of apo B might thus be useful for the treatment of diabetes-related hypertriglyceridaemia, hypercholesterolaemia and dyslipidaemia, and also for the prevention and treatment of obesity.

It has now been discovered that certain compounds of aroyl-O-piperidine structure have inhibitory properties on MTP and/or on the secretion of apoB.

As a result of this activity, these compounds have an entirely advantageous possible application in the treatment of diabetes-related hypertriglyceridaemia, hypercholesterolaemia and dyslipidaemia, but also in the prevention and treatment of obesity.

Thus, the present invention relates firstly to compounds of aroyl-O-piperidine structure of the general formula (I):

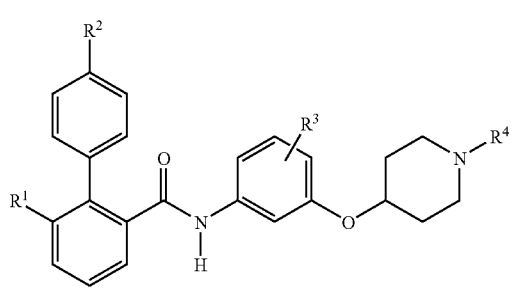

(I)

in which:

$R^1$ is chosen from a hydrogen atom, an alkyl radical and an alkoxy radical;

$R^2$ is chosen from an alkyl radical, an alkoxy radical, a trifluoromethyl radical and a trifluoromethoxy radical;

$R^3$ is chosen from a hydrogen atom and an alkyl radical;

$R^4$ is chosen from a hydrogen atom, an alkyl radical, an alkenyl radical, an alkynyl radical, an aryl radical, an arylalkyl radical, an arylalkenyl radical, an arylalkynyl radical, a cycloalkyl radical, a cycloalkylalkyl radical, a heterocyclyl radical, a heterocyclylalkyl radical, a heteroaryl radical, a heteroarylalkyl radical, a radical —C(=Z)—$R^5$, in which Z represents a sulfur or oxygen atom, and a radical —S(O)$_n$—$R^6$, in which n represents 1 or 2, $R^5$ is chosen from a hydrogen atom, an alkyl radical, an alkenyl radical, an alkynyl radical, a cycloalkyl radical, a cycloalkylalkyl radical, a heterocycloalkyl radical, a heterocycloalkylalkyl radical, an aryl radical, an arylalkyl radical, a heteroaryl radical, a heteroarylalkyl radical, a radical —O—$R^7$, a radical —C(=O)—O—$R^7$, a radical —S—$R^8$ and a radical —NR$^9$R$^{10}$, $R^6$ is chosen from an alkyl radical, an alkenyl radical, an alkynyl radical, a cycloalkyl radical, a heterocycloalkyl radical, an aryl radical, a heteroaryl radical, a cycloalkylalkyl radical, a heterocycloalkylalkyl radical, an arylalkyl radical and a heteroarylalkyl radical;

$R^7$ is chosen from a hydrogen atom, an alkyl radical, an alkenyl radical, an alkynyl radical, an alkoxyalkyl radical, a cycloalkyl radical, a heterocycloalkyl radical, an aryl radical, a heteroaryl radical, a cycloalkylalkyl radical, a heterocycloalkylalkyl radical, an arylalkyl radical and a heteroarylalkyl radical;

$R^8$ is chosen from a hydrogen atom, an alkyl radical, an alkenyl radical and an alkynyl radical;

$R^9$ is chosen from a hydrogen atom and an alkyl radical;

$R^{10}$ is chosen from a hydrogen atom, an alkyl radical, optionally substituted by a radical —C(=O)—O—$R^7$, an alkenyl radical, an alkynyl radical, a radical —S(O)$_n$—$R^6$, in which n represents 1 or 2, a cycloalkyl radical, a heterocycloalkyl radical, an aryl radical, a heteroaryl radical, a cycloalkylalkyl radical, a heterocycloalkylalkyl radical, an arylalkyl radical and a heteroarylalkyl radical;

the possible geometrical and/or optical isomers, epimers and tautomeric forms, and possible oxidised forms, especially amine oxides, thereof the solvates and hydrates of these compounds;

and also the possible pharmaceutically acceptable salts thereof with an acid or a base, or alternatively the pharmaceutically acceptable prodrugs of these compounds.

The following definitions specify the natures of the various groups and radicals defined above. Unless otherwise mentioned, these definitions apply for all the terms of the present invention thus specified.

The term "alkyl" denotes a linear or branched alkyl radical containing from 1 to 6 carbon atoms. Examples of alkyl radicals are methyl, ethyl, propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl and 1-methyl-1-ethylpropyl.

The term "alkenyl" denotes a linear or branched alkyl radical comprising at least one unsaturation in the form of a double bond and containing from 2 to 6 carbon atoms. Examples of alkenyl radicals are ethenyl, propenyl, propadienyl, butenyl, butadienyl, pentenyl, pentadienyl, hexenyl and hexadienyl, and also the branched isomers thereof; the absence of indication of the position of the double bond(s) should be understood as not placing any limitation on the double bond(s). For example, the "pentenyl" radical includes, without preference, the pent-1-en-1-yl, pent-2-en-1-yl and pent-3-en-1-yl radicals, but also the pent-1-en-2-yl, pent-2-en-2-yl and pent-3-en-2-yl radicals, and equally the pent-1-en-3-yl, pent-2-en-3-yl and pent-3-en-3-yl radicals.

The term "alkynyl" denotes a linear or branched alkyl radical comprising at least one unsaturation in the form of a triple bond and containing from 2 to 6 carbon atoms. Examples of alkynyl radicals are ethylynyl, propynyl, propadiynyl, butynyl, butadiynyl, pentynyl, pentadiynyl, hexynyl and hexadiynyl, and also the branched isomers thereof; the absence of indication of the position of the double bond(s) should be understood as not placing any limitation on the double bond(s). For example, the "pentynyl" radical includes, without preference, the pent-1-yn-1-yl, pent-2-yn-1-yl and pent-3-yn-1-yl radicals, but also the pent-1-yn-2-yl, pent-2-yn-2-yl and pent-3-yn-2-yl radicals, and equally the pent-1-yn-3-yl, pent-2-yn-3-yl and pent-3-yn-3-yl radicals.

Unless stated otherwise, the alkyl, alkenyl and alkynyl radicals defined above may be optionally substituted by one or more chemical species, which may be identical or different, chosen from a hydroxyl radical, a linear or branched alkoxy radical containing from 1 to 6 carbon atoms, and a radical —C(=O)—O—$R^7$, $R^7$ being as defined above.

The term "alkoxy" denotes a radical —O-alkyl, "alkyl" having the definition given above.

The term "cycloalkyl" denotes a bridged or unbridged mono-, bi- or tricyclic cycloalkyl radical containing from 3 to 13 carbon atoms, optionally comprising one or more double bonds, also including spirane compounds. Examples of cycloalkyl groups are especially cyclopropyl, cyclobutyl, cyclopentyl, cyclohexyl, cycloheptyl, cyclooctyl and cyclodecyl, adamantyl, diamantyl, nor-bornyl and bornyl groups.

The term "heterocyclyl" denotes a mono-, bi- or tricyclic radical containing a total of from 3 to 13 atoms, among which 1, 2, 3 or 4 are chosen, independently of each other, from nitrogen, oxygen and sulfur, optionally in oxidised form (in the case of nitrogen and sulfur), the other atoms being carbon atoms, the said heterocyclic radical also optionally comprising one or more double bonds, also including spirane compounds.

In particular, saturated or partially unsaturated monocyclic heterocyclyl radicals of 5 to 8 atoms are the saturated derivatives or, respectively, the partially unsaturated derivatives, of the heteroaryl radicals defined later. More particularly, among the heterocyclyl radicals, mention may be made of morpholino, morpholinyl, piperidinyl, thiazolidinyl, oxazolidinyl, tetrahydrothienyl, tetrahydrofuryl, tetrahydropyranyl, pyrrolidinyl, isoxazolidinyl, imidazolidinyl, pyrazolidinyl, quinuclidinyl, indolinyl, isoindolinyl, chromanyl, isochromanyl and benzodioxolanyl radicals, and the like.

The term "aryl" denotes a mono-, bi- or tricyclic aryl radical containing from 6 to 14 carbon atoms. Aryl radicals that may be mentioned in a non-limiting manner include phenyl, naphthyl, anthryl and phenanthryl radicals.

The term "heteroaryl" denotes a mono-, bi- or tricyclic aromatic radical containing a total of from 3 to 13 carbon atoms, among which 1, 2, 3 or 4 are chosen, independently of each other, from nitrogen, oxygen and sulfur, optionally in oxidised form (in the case of nitrogen and sulfur), the other atoms being carbon atoms.

Preferably, at least one of the monocycles constituting the heterocycle contains from 1 to 4 endocyclic hetero atoms, more preferably from 1 to 4 endocyclic hetero atoms. According to the invention, the heterocyclic polycyclic nucleus consists of one or more monocycles each containing from 5 to 8 atoms included in the ring.

Examples of monocyclic heteroaryl radicals are radicals derived from heteroaromatic compounds, such as pyridine, furan, thiophene, pyrrole, imidazole, thiazole, isothiazole, isoxazole, furazane, pyridazine, pyrimidine, pyrazine, thiazines, oxazole, pyrazole, oxadiazole, triazole and thiadiazole. Among the preferred heteroaryl radicals that may be mentioned are pyridyl, furyl, thienyl, pyrazolyl and imidazolyl.

Examples of bicyclic heteroaryl radicals in which each monocycle contains from 5 to 8 endocyclic atoms are derived from aromatic compounds chosen from indolizine, indole, isoindole, benzofuran, benzothiophene, indazole, benzimidazole, benzothiazole, benzoxadiazole, benzofurazane, benzothiofurazane, purine, quinoline, isoquinoline, cinnoline, phthalazine, quinazoline, quinoxaline, naphthyridines, pyrazolotriazines, pyrazolopyrimidine and pteridine.

The cycloalkyl, heterocyclyl, aryl and heteroaryl radicals defined above may be optionally substituted, unless otherwise mentioned, with one or more chemical species, which may be identical or different, chosen from halogen, i.e. fluorine, chlorine, bromine or iodine, alkyl, alkoxy, alkylthio, cyano, nitro, hydroxyl, trifluoromethyl, trifluoromethoxy and —C(=O)—O—$R^7$, $R^7$ being as defined above, and —$NR^9R^{10}$, $R^9$ and $R^{10}$ being as defined above.

The cycloalkylalkyl, heterocyclylalkyl, arylalkyl and heteroarylalkyl radicals should be understood in the present invention as being the cycloalkyl, heterocyclyl, aryl and heteroaryl radicals defined above, which replace a hydrogen of an alkyl radical, also as defined above. The arylalkenyl and arylalkynyl radicals have similar definitions, the replaced hydrogen being derived from an alkenyl or alkynyl radical, respectively.

Examples of cycloalkylalkyl, heterocyclylalkyl, arylalkyl, arylalkenyl, arylalkynyl and heteroarylalkyl radicals include the cyclohexylmethyl, tetrahydrofurylmethyl, benzyl, phenethyl, styryl and pyridylethyl radicals.

For the compounds of the formula (I) presented above, the term "geometrical isomer" means a cis/trans or E/Z isomerism. More particularly, the possible double bond(s) present in the various substituents of the compounds of the general formula (I) may be of E or Z configuration. These pure or impure geometrical isomers, alone or as a mixture, form an integral part of the compounds of the formula (I).

The term "optical isomer" includes all the isomeric forms, alone or as mixtures, resulting from the presence of one or more axes and/or centres of symmetry in the molecule, and resulting in rotation of a beam of polarised light. The term "optical isomer" more particularly includes enantiomers and diastereoisomers, in pure form or as a mixture, including racemic mixtures.

The acids capable of forming pharmaceutically acceptable salts with the compounds of the formula (I) above are organic or mineral acids. Non-limiting examples that may be mentioned include hydrochloric acid, hydrobromic acid, phosphoric acid, sulfuric acid, tartaric acid, citric acid, maleic acid, acetic acid, fumaric acid, alkanesulfonic acid, naphthalenesulfonic acid, para-toluenesulfonic acid, bis-trifluoroacetic acid and camphoric acid.

The bases capable of forming pharmaceutically acceptable salts with the compounds of the formula (I) above are mineral or organic bases. Among these bases, non-limiting examples that may be mentioned include sodium hydroxide, potassium hydroxide, ammonia, diethylamine, triethylamine, ethanolamine, diethanolamine, piperidine, piperazine, morpholine, basic amino acids, such as arginine and lysine, osamines, for example meglumine, and amino alcohols, such as 3-aminobutanol and 2-aminobutanol.

The invention especially covers the pharmaceutically acceptable salts, as indicated above, but also salts allowing a suitable separation or crystallisation of the compounds of the formula (I), such as the salts obtained with chiral amines.

The compounds of the formula (I) above also comprise the prodrugs of these compounds.

The term "prodrugs" means compounds which, once administered to the patient, are chemically and/or biologically converted by the living body, into compounds of the formula (I).

Among the compounds of the formula (I) according to the invention that are preferred are those for which the radical $R^3$ represents hydrogen, the possible geometrical and/or optical isomers, epimers and tautomeric forms, and optional oxidised forms, especially amine oxides, thereof, and the solvates and hydrates of these compounds;

and also the possible pharmaceutically acceptable salts thereof with an acid or a base, or the pharmaceutically acceptable prodrugs of these compounds.

Preference is also given to the compounds of the formula (I) according to the invention for which the radical $R^1$ represents hydrogen or a methyl radical, the possible geometrical and/or optical isomers, epimers and tautomeric forms, and optional oxidised forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the general formula (I) in which the radical $R^2$ represents a trifluoromethoxy radical, a trifluoromethyl radical, a methoxy radical or a methoxyethoxy radical, and $R^2$ more preferably represents a trifluoromethoxy radical or a trifluoromethyl radical, the possible geometrical and/or optical isomers, epimers and tautomeric forms, and optional oxidised forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the general formula (I) in which the radical $R^4$ represents —S(O)$_2$—R$^6$, —C(=O)—O—R$^7$ or —C(=O)—NHR$^{10}$, R$^6$, R$^7$ and R$^{10}$ being as defined above, the possible geometrical and/or optical isomers, epimers and tautomeric forms, and optional oxidised forms, especially amine oxides, thereof, and the solvates and hydrates of these compounds;

and also the possible pharmaceutically acceptable salts thereof with an acid or a base, or the pharmaceutically acceptable prodrugs of these compounds.

A subgroup that is most particularly preferred among the compounds of the general formula (I) consists of the compounds of the general formula (I) in which:

$R^1$ represents hydrogen or a methyl radical; and $R^2$ is chosen from a trifluoromethoxy radical, a trifluoromethyl radical, a methoxy radical and a methoxyethoxy radical, preferably chosen from a trifluoromethoxy radical and a trifluoromethyl radical; and $R^3$ represents hydrogen; and $R^4$ represents —S(O)$_2$—R$^6$, —C(=O)—O—R$^7$ or —C(=O)—NHR$^{10}$, R$^6$, R$^7$ and R$^{10}$ being as defined above, the possible geometrical and/or optical isomers, epimers and tautomeric forms, and possible oxidised forms, especially amine oxides, thereof the solvates and hydrates of these compounds;

and also the possible pharmaceutically acceptable salts thereof with an acid or a base, or alternatively the pharmaceutically acceptable prodrugs of these compounds.

Particularly preferred examples of compounds according to the present invention are chosen from:

6-methyl-N-[3-[[1-(methylsulfonyl)-4-piperidinyl]oxy]phenyl]-4'-(trifluoro-methoxy)[1,1'-biphenyl]-2-carboxamide;

N-[3-[(1-acetyl-4-piperidinyl)oxy]phenyl]-6-methyl-4'-(trifluoromethoxy)[1,1'-biphenyl]-2-carboxamide;

methyl 4-[3-[[[6-methyl-4'-(trifluoromethoxy)[1,1'-biphenyl]-2-yl]carbonyl]-amino]phenoxy]-1-piperidinecarboxylate;

ethyl 4-[3-[[[6-methyl-4'-(trifluoromethoxy)[1,1'-biphenyl]-2-yl]carbonyl]-amino]phenoxy]-1-piperidinecarboxylate;

phenylmethyl 4-[3-[[[6-methyl-4'-(trifluoromethoxy)[1,1'-biphenyl]-2-yl]carbonyl]amino]phenoxy]-1-piperidinecarboxylate;

2-methylpropyl 4-[3-[[[6-methyl-4'-(trifluoromethoxy)[1,1'-biphenyl]-2-yl]carbonyl]amino]phenoxy]-1-piperidinecarboxylate;

4-nitrophenyl 4-[3-[[[6-methyl-4'-(trifluoromethoxy)[1,1'-biphenyl]-2-yl]carbonyl]amino]phenoxy]-1-piperidinecarboxylate;

S-methyl 4-[3-[[[6-methyl-4'-(trifluoromethoxy)[1,1'-biphenyl]-2-yl]carbonyl]-amino]phenoxy]-1-piperidinecarbothioate;

4-[3-[[[6-methyl-4'-(trifluoromethoxy)[1,1'-biphenyl]-2-yl]carbonyl]amino]-phenoxy]-N-phenyl-1-piperidinecarboxamide;

N-ethyl-4-[3-[[[6-methyl-4'-(trifluoromethoxy)[1,1'-biphenyl]-2-yl]carbonyl]-amino]phenoxy]-1-piperidinecarboxamide;

6-methyl-N-[3-[[1-[(1-methylethyl)sulfonyl]-4-piperidinyl]oxy]phenyl]-4'-(trifluoromethoxy)[1,1'-biphenyl]-2-carboxamide;

6-methyl-N-[3-[[1-(phenylsulfonyl)-4-piperidinyl]oxy]phenyl]-4'-(trifluoromethoxy)[1,1'-biphenyl]-2-carboxamide;

6-methyl-N-[3-[[1-[(phenylmethyl)sulfonyl]-4-piperidinyl]oxy]phenyl]-4'-(trifluoromethoxy)[1,1'-biphenyl]-2-carboxamide;

N-[3-[[1-[(5-chloro-1,3-dimethyl-1H-pyrazol-4-yl)sulfonyl]-4-piperidinyl]oxy]-phenyl]-6-methyl-4'-(trifluoromethoxy)[1,1'-biphenyl]-2-carboxamide;

N-[3-[[1-(butylsulfonyl)-4-piperidinyl]oxy]phenyl]-6-methyl-4'-(trifluoromethoxy)[1,1'-biphenyl]-2-carboxamide;

N-(4-methoxyphenyl)-4-[3-[[[6-methyl-4'-(trifluoromethoxy)[1,1'-biphenyl]-2-yl]carbonyl]amino]phenoxy]-1-piperidinecarboxamide;

ethyl N-[[4-[3-[[[6-methyl-4'-(trifluoromethoxy)[1,1'-biphenyl]-2-yl]carbonyl]-amino]phenoxy]-1-piperidinyl]carbonyl]glycinate;

4-[3-[[[6-methyl-4'-(trifluoromethoxy)[1,1'-biphenyl]-2-yl]carbonyl]amino]-phenoxy]-N-2-propenyl-1-piperidinecarboxamide;

N-butyl-4-[3-[[[6-methyl-4'-(trifluoromethoxy)[1,1'-biphenyl]-2-yl]carbonyl]-amino]phenoxy]-1-piperidinecarboxamide;

4-[3-[[[6-methyl-4'-(trifluoromethoxy)[1,1'-biphenyl]-2-yl]carbonyl]amino]-phenoxy]-N-(phenylmethyl)-1-piperidinecarboxamide;

methyl 2-[[[4-[3-[[[6-methyl-4'-(trifluoromethoxy)[1,1'-biphenyl]-2-yl]carbonyl]-amino]phenoxy]-1-piperidinyl]carbonyl]amino]benzoate;

N-(3-cyanophenyl)-4-[3-[[[6-methyl-4'-(trifluoromethoxy)[1,1'-biphenyl]-2-yl]-carbonyl]amino]phenoxy]-1-piperidinecarboxamide;

N-[4-(methylthio)phenyl]-4-[3-[[[6-methyl-4'-(trifluoromethoxy)[1,1'-biphenyl]-2-yl]carbonyl]amino]phenoxy]-1-piperidinecarboxamide;

4-[3-[[[6-methyl-4'-(trifluoromethoxy)[1,1'-biphenyl]-2-yl]carbonyl]amino]-phenoxy]-N-(2-phenylethyl)-1-piperidinecarboxamide;

N-hexyl-4-[3-[[[6-methyl-4'-(trifluoromethoxy)[1,1'-biphenyl]-2-yl]carbonyl]-amino]phenoxy]-1-piperidinecarboxamide;

butyl N-[[4-[3-[[[6-methyl-4'-(trifluoromethoxy)[1,1'-biphenyl]-2-yl]carbonyl]-amino]phenoxy]-1-piperidinyl]carbonyl]glycinate;

4-[3-[[[6-methyl-4'-(trifluoromethoxy)[1,1'-biphenyl]-2-yl]carbonyl]amino]-phenoxy]-N-[2-(trifluoromethoxy)phenyl]-1-piperidinecarboxamide;

N-[4-(dimethylamino)phenyl]-4-[3-[[[6-methyl-4'-(trifluoromethoxy)[1,1'-biphenyl]-2-yl]carbonyl]amino]phenoxy]-1-piperidinecarboxamide;

N-[(4-methoxyphenyl)methyl]-4-[3-[[[6-methyl-4'-(trifluoromethoxy)[1,1'-biphenyl]-2-yl]carbonyl]amino]phenoxy]-1-piperidinecarboxamide;

methyl 4-[[[4-[3-[[[6-methyl-4'-(trifluoromethoxy)[1,1'-biphenyl]-2-yl]carbonyl]-amino]phenoxy]-1-piperidinyl]carbonyl]amino]benzoate;

N-1,3-benzodioxol-5-yl-4-[3-[[[6-methyl-4'-(trifluoromethoxy)[1,1'-biphenyl]-2-yl]carbonyl]amino]phenoxy]-1-piperidinecarboxamide;

[1,1'-biphenyl]-6-methyl-N-[3-[[1-(phenylmethyl)-4-piperidinyl]oxy]phenyl]-4'-(trifluoromethoxy)-2-carboxamide;

[1,1'-biphenyl]-6-methyl-N-[3-[[1-(2-thienylmethyl)-4-piperidinyl]oxy]phenyl]-4'-(trifluoromethoxy)-2-carboxamide;

N-[3-[[1-(2-benzofuranylmethyl)-4-piperidinyl]oxy]phenyl]-6-methyl-4'-(trifluoromethoxy)[1,1'-biphenyl]-2-carboxamide;

methyl 4-[3-[[[4'-(trifluoromethoxy)[1,1'-biphenyl]-2-yl]carbonyl]amino]-phenoxy]-1-piperidinecarboxylate;

methyl 4-[3-[[[4'-(trifluoromethyl)[1,1'-biphenyl]-2-yl]carbonyl]amino]-phenoxy]-1-piperidinecarboxylate;

2-methoxyethyl 4-[3-[[[6-methyl-4'-(trifluoromethoxy)[1,1'-biphenyl]-2-yl]carbonyl]amino]phenoxy]-1-piperidinecarboxylate;

2-methoxyethyl 4-[3-[[[4'-(trifluoromethoxy)[1,1'-biphenyl]-2-yl]carbonyl]-amino]phenoxy]-1-piperidinecarboxylate;

2-methoxyethyl 4-[3-[[[4'-(trifluoromethyl)[1,1'-biphenyl]-2-yl]carbonyl]amino]-phenoxy]-1-piperidinecarboxylate;

ethyl 4-[3-[[[4'-(trifluoromethoxy)[1,1'-biphenyl]-2-yl]carbonyl]amino]-phenoxy]-1-piperidinecarboxylate;

N-[3-[[1-(4-methoxybenzoyl)-4-piperidinyl]oxy]phenyl]-6-methyl-4'-(trifluoromethoxy)[1,1'-biphenyl]-2-carboxamide;

N-[3-[[1-(5-isoxazolylcarbonyl)-4-piperidinyl]oxy]phenyl]-6-methyl-4'-(trifluoromethoxy)[1,1'-biphenyl]-2-carboxamide;

N-[3-[[1-[2-(4-methoxyphenyl)acetyl]-4-piperidinyl]oxy]phenyl]-6-methyl-4'-(trifluoromethoxy)[1,1'-biphenyl]-2-carboxamide;

N-[3-[[1-[2-(acetyloxy)acetyl]-4-piperidinyl]oxy]phenyl]-6-methyl-4'-(trifluoromethoxy)[1,1'-biphenyl]-2-carboxamide;

N-[3-[[1-(3,4-dimethoxybenzoyl)-4-piperidinyl]oxy]phenyl]-6-methyl-4'-(trifluoromethoxy)[1,1'-biphenyl]-2-carboxamide;

N-[3-[[1-(4-nitrobenzoyl)-4'-piperidinyl]oxy]phenyl]-4'-(trifluoromethoxy)[1,1'-biphenyl]-2-carboxamide;

N-[3-[[1-(5-isoxazolylcarbonyl)-4-piperidinyl]oxy]phenyl]-4'-(trifluoromethoxy)[1,1'-biphenyl]-2-carboxamide;

6-methyl-N-[3-[[1-[(2E)-1-oxo-2-butenyl]-4'-piperidinyl]oxy]phenyl]-4'-(trifluoromethoxy)[1,1'-biphenyl]-2-carboxamide;

6-methyl-N-[3-[[1-(2-methyl-1-oxopropyl)-4-piperidinyl]oxy]phenyl]-4'-(trifluoromethoxy)[1,1'-biphenyl]-2-carboxamide;

methyl 4-[3-[[[6-methyl-4'-(trifluoromethyl)[1,1'-biphenyl]-2-yl]carbonyl]-amino]phenoxy]-1-piperidinecarboxylate;

methyl 4-[3-[[(4'-methoxy[1,1'-biphenyl]-2-yl)carbonyl]amino]phenoxy]-1-piperidinecarboxylate;

1,1-dimethylethyl 4-[3-[[[6-methyl-4'-(trifluoromethyl)[1,1'-biphenyl]-2-yl]-carbonyl]amino]phenoxy]-1-piperidinecarboxylate;

1,1-dimethylethyl 4-[3-[[(4'-methoxy[1,1'-biphenyl]-2-yl)carbonyl]amino]-phenoxy]-1-piperidinecarboxylate;

6-methyl-N-[3-(4-piperidinyloxy)phenyl]-4'-(trifluoromethyl)[1,1'-biphenyl]-2-carboxamide;

2-methoxyethyl 4-[3-[[[6-methyl-4'-(trifluoromethyl)[1,1'-biphenyl]-2-yl]-carbonyl]amino]phenoxy]-1-piperidinecarboxylate, the optical isomers and oxidised forms thereof, solvates and hydrates of these compounds;

and also the possible pharmaceutically acceptable salts thereof with an acid, or alternatively the pharmaceutically acceptable prodrugs of these compounds.

The present invention also relates to the process for the preparation of the compounds of the formula (I) as have just been defined.

In general, the compounds of the present invention can be prepared by reacting an acid of the formula (II) and an amine of the formula (III) according to the following reaction scheme:

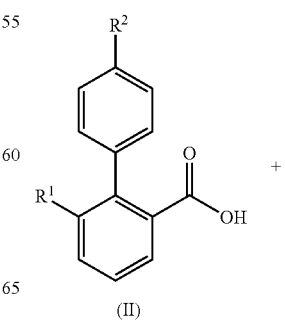

(II)

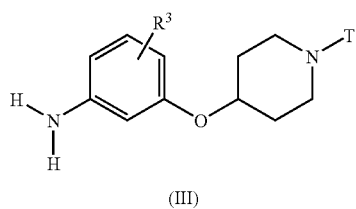

(III)

in which formulae $R^1$, $R^2$ and $R^3$ are as defined above, and T represents a labile protecting group, for example tert-butoxycarbonyl (BOC), according to standard amide synthesis techniques that are well known to those skilled in the art, leading to the compounds of the formula (IV):

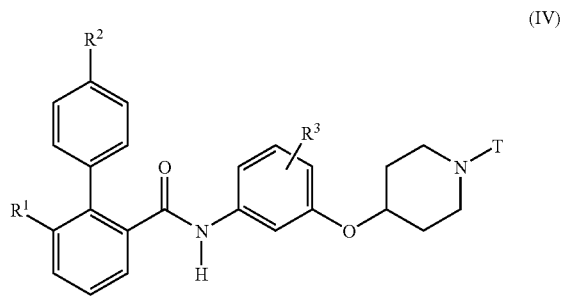

(IV)

in which T, $R^1$, $R^2$ and $R^3$ are as defined above, the labile protecting function T of which is removed to give the compounds of the formula ($I_A$), which is a special case of the compounds of the formula (I) for which $R^4$ represents hydrogen:

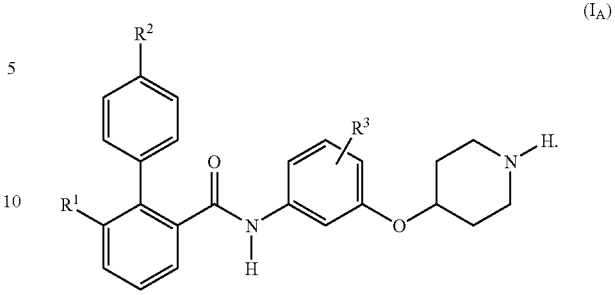

($I_A$)

According to one variant of the process according to the invention, the amide of the formula (IV) can also be prepared from the amine (III) and an acyl halide, preferably the acyl chloride of the acid (II), according to standard techniques known in the field of organic chemistry.

The amine of the formula ($I_A$) described above can then be converted into substituted amine derivatives, amides, carbamates, sulfonamides, ureas, etc., according to the synthetic techniques usually used by those skilled in the art, to give the set of compounds of the formula (I), with $R^4$ possibly taking all the definitions indicated above in the present description, with the exception of hydrogen. Syntheses of substituted amines, amides, carbamates, sulfonamides and ureas will be given by way of illustration in the "Examples" section of the present description.

The compounds of the formula (I) thus obtained can then be purified, where appropriate, the geometrical and/or optical isomers thereof can optionally be separated, converted, if so desired, into the oxidised forms thereof, especially amine oxides, or into the solvated or hydrated forms thereof, or alternatively salified with an acid or a base, to give the corresponding pharmaceutically acceptable salts.

The acids of the formula (II) are either commercially available, or are readily prepared from commercially available products, according to known procedures. By way of example, the acids of the formula (II) can be synthesised according to the following scheme:

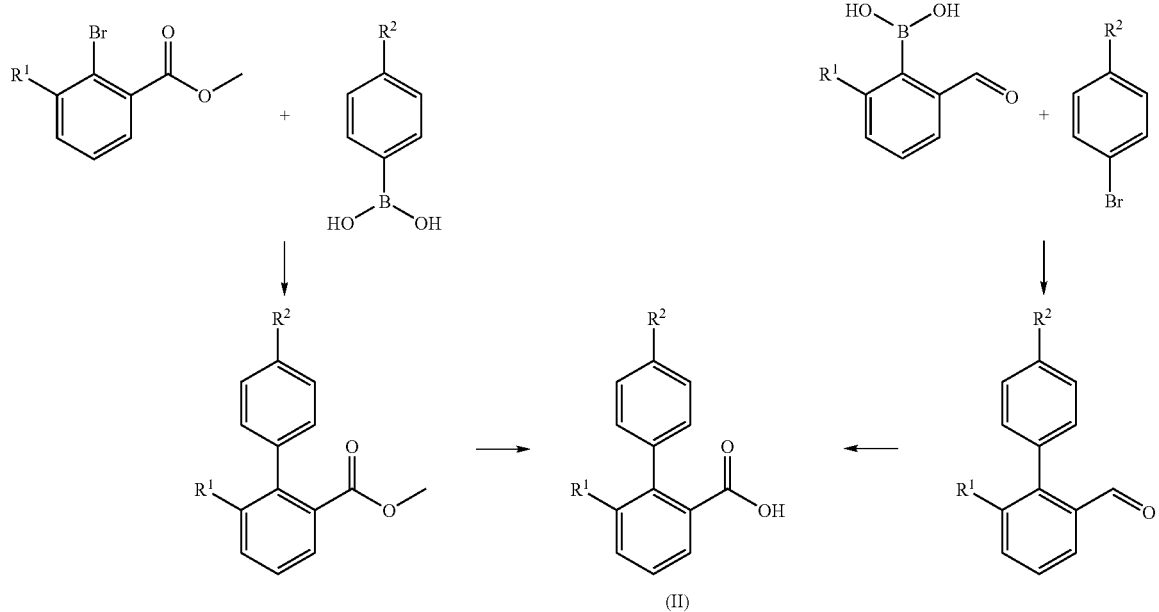

(II)

in which scheme $R^1$ and $R^2$ have the definitions given above, with standard operating conditions that are entirely familiar in the field of the coupling of boronic acid derivatives with halogenated compounds. Examples of such couplings are given, by way of illustration, in the description hereinbelow.

The amines of the formula (III) are also either commercially available or are readily prepared from commercially available products, according to known procedures. By way of example, the amines of the formula (III) can be synthesised from the nitro derivatives thereof prepared as described in patent application WO-A-2003/068760. The examples below give an illustration of the synthesis of an amine of the formula (III).

In the processes described above, it should be understood that the operating conditions may vary substantially depending on the various substituents present in the compounds of the formula (I) that it is desired to prepare. Such variations and adaptations are readily available to a person skilled in the art, for example from scientific reviews, the patent literature, Chemical Abstracts, and computer databases, including the Internet.

The present invention also relates to pharmaceutical compositions comprising an effective pharmaceutical amount of a compound of the formula (I), as defined above, in combination with one or more pharmaceutically acceptable vehicles.

These compositions can be administered orally in the form of immediate-release or controlled-release tablets, gel capsules or granules, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatin, Shellac, hydroxypropylcellulose, hydroxypropylmethylcellulose, calcium citrate, dextrin and pectin.

Examples of lubricants include magnesium stearate, talc, polyethylene glycol, silica and hardened plant oils. The colorant may be any colorant permitted for use in medicaments.

Examples of flavour enhancers include cocoa powder, mint in herb form, aromatic powder, mint in oil form, borneol and cinnamon powder. It should be understood that the tablet or granule can be suitably coated with sugar, gelatin or the like.

An injectable form comprising the compound of the present invention as active principle is prepared, where appropriate, by mixing the said compound with a pH regulator, a buffer agent, a suspension agent, a solubiliser, a stabiliser, a tonicity agent and/or a preserving agent, and by converting the mixture into a form for intravenous, subcutaneous or intramuscular injection, according to a conventional process. Where appropriate, the injectable form obtained can be lyophilised via a conventional process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilisers include castor oil solidified with polyoxyethylene, polysorbate 80, nicotinamide, polyethoxylated sorbitan monolaurate and the ethyl ester of castor oil fatty acid.

In addition, the stabiliser includes sodium sulfite, sodium metasulfite and ether, while the preserving agent includes methyl para-hydroxybenzoate, ethyl para-hydroxybenzoate, sorbic acid, phenol, cresol and chlorocresol.

The present invention also relates to the use of a compound of the formula (I) of the invention for the preparation of a medicament for the treatment of diabetes-related hypertriglyceridaemia, hypercholesterolaemia and dyslipidaemia, but also for the prevention and treatment of obesity.

The effective administration doses and posologies of the compounds of the invention, intended for the prevention or treatment of a disease, disorder or condition caused by or associated with modulation of MTP activity, depends on a large number of factors, for example on the nature of the inhibitor, the size of the patient, the aim of the desired treatment, the nature of the pathology to be treated, the specific pharmaceutical composition used and the observations and the conclusions of the treating physician.

For example, in the case of an oral administration, for example a tablet or a gel capsule, a possible suitable dosage of the compounds of the formula (I) is between about 0.1 mg/kg and about 100 mg/kg of body weight per day, preferably between about 0.5 mg/kg and about 50 mg/kg of body weight per day, more preferably between about 1 mg/kg and about 10 mg/kg of body weight per day and more preferably between about 2 mg/kg and about 5 mg/kg of body weight per day of active material.

If representative body weights of 10 kg and 100 kg are considered in order to illustrate the oral daily dosage range that can be used and as described above, suitable dosages of the compounds of the formula (I) will be between about 1-10 mg and 1000-10 000 mg per day, preferably between about 5-50 mg and 500-5000 mg per day, more preferably between about 10.0-100.0 mg and 100.0-1000.0 mg per day and even more preferably between about 20.0-200.0 mg and about 50.0-500.0 mg per day of active material comprising a preferred compound.

These dosage ranges represent total amounts of active material per day for a given patient. The number of administrations per day at which a dose is administered may vary within wide proportions depending on pharmacokinetic and pharmacological factors, such as the half-life of the active material, which reflects its rate of catabolism and clearance, and also the minimum and optimum levels of the said active material, in blood plasma or in other bodily fluids, which are reached in the patient and which are required for therapeutic efficacy.

Many other factors should also be taken into consideration when determining the number of daily administrations and the amount of active material that should be administered in a single dosage intake. Among these other factors, and not the least of which, is the individual response of the patient to be treated.

The examples that follow illustrate the present invention without limiting it in any way. In these examples, the following abbreviations have been used:

| | |
|---|---|
| TLC: | thin-layer chromatography |
| DCM: | dichloromethane |
| Yld: | Yield |
| NMR: | Nuclear Magnetic Resonance |
| DME: | dimethyl ether |
| EtOAc: | ethyl acetate |
| THF: | tetrahydrofuran |
| DMA: | dimethylacetonide |

A) Preparation of the Acids of the Formula (II)

Example A₁

4'-(2-methoxyethoxy)-1,1'-biphenyl-2-carboxylic acid

Step a: 1-bromo-4-(2-methoxyethoxy)benzene

4-Bromophenol (8.65 g; 0.05 mol), 2-methoxyethanol (1.1 eq.; 0.055 mol; 4.36 ml) and triphenylphosphine (1.1 eq.; 0.055 mol; 14.4 g) are dissolved in 210 ml of toluene. The reaction medium is brought to 54° C. and diisopropyl azodicarboxylate (1.0 eq.; 0.05 mol; 10.1 g) dissolved in 21 ml of toluene is added dropwise. The reaction medium is left at 54° C. for one hour and then overnight at room temperature, and is then evaporated to dryness. The crude product is purified by flash chromatography on silica on a gradient of heptane comprising 0-100% DCM to give 9.6 g of the expected product in the form of an oil.

TLC (1/4 heptane/DCM): Rf=0.46
Yld=83.1%
$^1$H NMR (300 MHz, chloroform-D) δ ppm: 3.4 (s, 3H); 3.7 (m, 2H); 4.1 (m, 2H); 6.8 (d, J=9.0 Hz, 2H); 7.4 (m, 2H).

Step b: 4'-(2-methoxyethoxy)-1,1'-biphenyl-2-carbaldehyde

The 1-bromo-4-(2-methoxyethoxy)benzene obtained in the preceding step (2.30 g; 10.0 mmol), 2-formylphenylboronic acid (1.4 eq.; 14 mmol; 2.10 g) and caesium fluoride (3.0 eq.; 30.0 mmol; 4.56 g) are dissolved in 38 ml of DME, and tetrakis(triphenylphosphine)palladium (0.3 mmol; 0.347 g) is then added and the reaction medium is heated at 65° C. for 16 hours, and then at 80° C. for 4 hours. The mixture is allowed to cool to room temperature and 15 ml of ethyl ether are then added; the reaction medium is washed twice with 45 ml of water, and then dried over sodium sulfate and evaporated to dryness. The crude product is purified by flash chromatography on silica (eluting with heptane 0-100% DCM) to give 1.36 g of the expected product in the form of an oil.

TLC (1/1 heptane/EtOAc): Rf=0.54
Yld=53.1%
$^1$H NMR (300 MHz, chloroform-D) δ ppm: 3.5 (s, 3H); 3.8 (m, 2H); 4.2 (m, 2H); 7.0 (m, 2H); 7.3 (m, 2H); 7.5 (m, 2H); 7.6 (m, J=7.5; 1.5 Hz, 1H); 8.0 (dd, J=7.5; 1.2 Hz, 1H); 10.0 (d, J=0.8 Hz, 1H).

Step c: 4'-(2-methoxyethoxy)-1,1'-biphenyl-2-carboxylic acid

The 4'-(2-methoxyethoxy)-1,1'-biphenyl-2-carbaldehyde from step b (3.691 g; 14.4 mmol) is dissolved in 45 ml of acetone, the mixture is cooled to 0° C. and 10.85 ml of Jones' reagent (solution of 3.5 g of chromium trioxide in a solution of 3.16 ml of sulfuric acid in 10 ml of water) are then added dropwise. After 1 hour at 0° C., the reaction medium is allowed to cool to room temperature over 8 hours. The reaction medium is evaporated to dryness, taken up in ether and filtered through silica. The organic phase is extracted with aqueous 1N sodium hydroxide solution, and the aqueous phase is then acidified with 1N hydrochloric acid and extracted with DCM. The organic phase is dried over sodium sulfate and evaporated to dryness to give 2.75 g of the expected product in the form of an oil.

TLC (1/2 heptane/EtOAc): Rf=0.47
Yld=70.1%
$^1$H NMR (300 MHz, chloroform-D) δ ppm: 3.5 (s, 3H); 3.8 (m, 2H); 4.2 (m, 2H); 7.0 (m, J=8.7 Hz, 2H); 7.3 (m, 2H); 7.4 (m, 2H); 7.5 (m, J=7.2 Hz, 1H); 7.9 (m, J=7.6 Hz, 1H).

B) Preparation of the Amines of the Formula (III)

Example B₁ tert-butyl 4-(3-aminophenoxy)piperidine-1-carboxylate tert-Butyl 4-(3-nitrophenoxy)piperidine-1-carboxylate (prepared as described in WO-A-2003/068760) (10.764 g; 33.39 mmol) is dissolved in 430 ml of ethanol, Raney nickel (7.2 g) is then added and the reaction medium is placed under hydrogen (pressure: 50 bar) at room temperature overnight. The reaction medium is filtered through Celite and evaporated to dryness to give quantitatively (9.76 g) the expected product in the form of a beige-coloured oil.

TLC (97/3 dichloromethane/methanol): Rf=0.53
Yld: quantitative
$^1$H NMR (300 MHz, chloroform-D) δ ppm: 1.5 (s, 9H); 1.7 (m, 2H); 1.9 (m, 2H); 3.3 (m, 2H); 3.7 (m, 2H); 4.4 (m, 1H); 6.3 (m, 3H); 7.1 (t, J=8.0 Hz, 1H); 7.3 (s, 2H).

C) Coupling of Acid (II) and Amine (III)

Example C₁

1,1-dimethylethyl 4-[3-[[[6-methyl-4'-(trifluoromethoxy)[1,1'-biphenyl]-2-yl]carbonyl]amino]phenoxy]-1-piperidinecarboxylate Example 1 of the Table of Compounds 6-Methyl-4'-trifluoromethoxybiphenyl-2-carbonyl chloride (4.72 g; 15.0 mmol), obtained from 6-methyl-4'-trifluoromethoxybiphenyl-2-carboxylic acid, according to a procedure similar to that in Example A₁, is dissolved in 50 ml of dichloromethane, and triethylamine (1.5 eq.; 22.5 mmol; 3.14 ml) is then added. tert-Butyl 4-(3-aminophenoxy)piperidine-1-carboxylate (Example B₁; 1.0 eq.; 15.0 mmol; 4.39 g) dissolved in 50 ml of dichloromethane is added dropwise. The reaction medium is stirred at room temperature overnight and then washed three times with saturated aqueous sodium hydrogen carbonate solution, dried over sodium sulfate and evaporated to dryness. The crude product is purified by flash chromatography on silica with a heptane/EtOAc gradient, to give 8.06 g of the expected product.

Yld=94%

The examples that follow illustrate a number of examples of conversion of the amine function of the piperidine ring of the compound obtained in Example C₁, or of similar compounds.

Example T₁

Deprotection of the Amine Function 6-methyl-N-[3-(4-piperidinyloxy)phenyl]-4'-(trifluoromethoxy)-[1,1'-biphenyl]-2-carboxamide Example 2 of the Table of Compounds The tert-butyl 4-{3-[(6-methyl-4'-trifluoromethoxybiphenyl-2-carbonyl)-amino]phenoxy}piperidine-1-carboxylate of Example C₁ (8.53 g; 14.95 g) is dissolved in 140 ml of dichloromethane, and trifluoroacetic acid (16 ml) is then added slowly. The reaction medium is left at room temperature for 1 hour 30 minutes, and is evaporated to dryness. The crude product is taken up in dichloromethane and washed with saturated aqueous sodium hydrogen carbonate solution, dried over sodium sulfate and evaporated to dryness to give 7.0 g of the expected product in the form of a cream-coloured foam.
Yld=quantitative Example T$_2$ Formation of the Amides N-[3-[(1-acetyl-4-piperidinyl)oxy]phenyl]-6-methyl-4'-(trifluoromethoxy)-[1,1'-biphenyl]-2-carboxamide Example 4 of the Table of Compounds N-[3-(Piperidin-4-yloxy)phenyl]-6-methyl-4'-trifluoromethoxybiphenyl-2-carboxamide (70.6 mg; 0.15 mmol) and N-methylmorpholine polystyrene resin (3.6 eq.; 0.54 mmol) are dissolved in 3.5 ml of THF. The resin is left to swell for 3 hours at room temperature. Acetoxyacetyl chloride (1.2 eq.; 0.18 mmol; 24.6 mg) is then added. The reaction medium is stirred at room temperature overnight, 3.0 eq. of Trisamine polystyrene resin (0.45 mmol) are then added and the reaction medium is stirred for a further 3 hours at room temperature. After filtration, the filtrate is evaporated and the crude product is purified by flash chromatography on silica (elution: gradient of heptane to 100% ethyl acetate) to give 82.1 mg of the expected product.
Yld=96%
Mass: ES+=513.3.

Example T$_3$

Formation of the Carbamates methyl 4-[3-[[[6-methyl-4'-(trifluoromethoxy)[1,1'-biphenyl]-2-yl]-carbonyl]amino]phenoxy]-1-piperidinecarboxylate Example 5 of the Table of Compounds N-[3-(Piperidin-4-yloxy)phenyl]-6-methyl-4'-trifluoromethoxybiphenyl-2-carboxamide (612 mg; 1.3 mmol), 2-methoxyethyl chloroformate (1.4 eq.; 1.8 mmol; 252 mg), triethylamine (1.9 eq.; 2.5 mmol; 0.34 ml) and 4-dimethylaminopyridine (0.1 eq.; 0.13 mmol; 16 mg) are dissolved in 33 ml of chloroform. The reaction medium is refluxed for 6 hours and is then washed with saturated aqueous sodium hydrogen carbonate solution, dried over sodium sulfate and evaporated to dryness. The crude product is purified by flash chromatography on silica with a heptane/EtOAc gradient to give 540 mg of the expected product in the form of a white foam.
TLC (1/2 heptane/EtOAc): Rf=0.4
Yld=73%

Example T$_4$

Formation of the Sulfonamides

N-[3-[[1-[(4-methoxyphenyl)sulfonyl]-4-piperidinyl]oxy]phenyl]-6-methyl-4'-(trifluoromethoxy)[1,1'-biphenyl]-2-carboxamide Example 18 of the Table of Compounds N-[3-(Piperidin-4-yloxy)phenyl]-6-methyl-4'-trifluoromethoxybiphenyl-2-carboxamide (94.1 mg; 0.2 mmol) and 3.6 eq. of N-methylmorpholine polystyrene resin (0.72 mmol) are dissolved in 3.5 ml of THF and the resin is left to swell for 3 hours at room temperature. para-Methoxybenzenesulfonyl chloride (1.2 eq.; 0.18 mmol; 24.6 mg) dissolved in 2.5 ml of THF is added, the reaction medium is stirred at room temperature overnight, 3.0 eq. of Trisamine polystyrene resin (0.45 mmol) are then added and the reaction medium is stirred for a further 3 hours at room temperature. After filtration, the filtrate is evaporated and the crude product is purified by flash chromatography on silica (elution: gradient of heptane to 100% EtOAc) to give 113 mg of the expected product.
Yld=88%
Mass: ES−=639.3.

Example T$_5$

Formation of the Ureas

N-[(4-methoxyphenyl)methyl]-4-[3-[[[6-methyl-4'-(trifluoromethoxy)[1,1'-biphenyl]-2-yl]carbonyl]amino]phenoxy]-1-piperidinecarboxamide Example 52 of the Table of Compounds N-[3-(Piperidin-4-yloxy)phenyl]-6-methyl-4'-trifluoromethoxybiphenyl-2-carboxamide (94.1 mg; 0.2 mmol) is dissolved in 5 ml of dichloromethane, and 4-methoxybenzyl isocyanate (1.1 eq.; 31.4 ml) is added. The reaction medium is stirred for 8 hours and Trisamine polystyrene resin (0.3 eq.; 0.6 mmol) is then added. Stirring is continued at room temperature overnight. After filtration, the filtrate is evaporated and the crude product is purified by flash chromatography on silica (elution: gradient of heptane to 100% EtOAc) to give 103.5 mg of the expected product.
Yld=82%
Mass: ES−=632.4.

Example T$_6$

Formation of the Amines 6-methyl-N-[3-[[1-(phenylmethyl)-4-piperidinyl]oxy]phenyl]-4'-(trifluoromethoxy)[1,1'-biphenyl]-2-carboxamide Example 58 of the Table of Compounds N-[3-(Piperidin-4-yloxy)phenyl]-6-methyl-4'-trifluoromethoxybiphenyl-2-carboxamide (94.1 mg; 0.2 mmol) is dissolved in 1 ml of a 4/1 THF/BMA mixture, and 4.5 ml of DMA are then added. Benzaldehyde (1.3 eq.; 0.26 mmol; 26.5 ml) and acetic acid (1.0 eq.; 0.2 mmol; 63.6 mg) are added. After stirring for 30 minutes at room temperature, sodium triacetoxyborohydride (1.5 eq.; 0.3 mmol; 63.6 mg) is added and the reaction medium is stirred overnight. The reaction medium is evaporated to dryness, taken up in dichloromethane and washed successively with saturated sodium bicarbonate solution and with water (twice), and then evaporated to dryness. The crude product is purified by flash chromatography on silica (elution: gradient of heptane to 100% EtOAc) to give 75 mg of the expected product.
Yld=67%
Mass: ES+=561.4.

The compounds of Examples T$_1$ to T$_6$ above, and also other compounds corresponding to the general formula (I) according to the invention and prepared according to similar procedures, are collated in the following table:

TABLE 1

| No. | STRUCTURES | NMR | MASS | NOMENCLATURE |
|---|---|---|---|---|
| 1 | 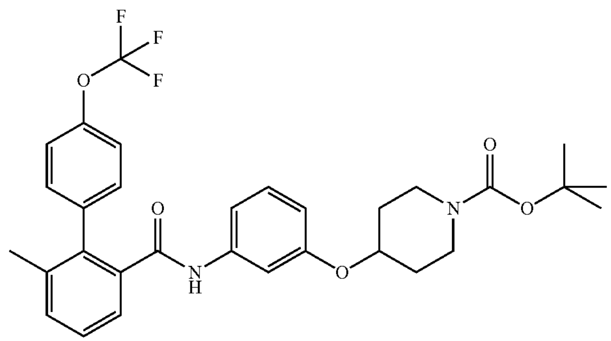 | | | 1,1-dimethylethyl 4-[3-[[[6-methyl-4'-(trifluoromethoxy)][1,1'-biphenyl]-2-yl]carbonyl]amino]phenoxy]-1-piperidine-carboxylate |
| 2 | 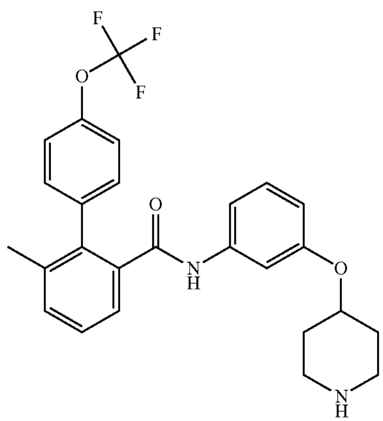 | ¹H NMR(300 MHz; Chloroform-D); δ ppm: 1.8(dd; J=13.4; 3.6 Hz; 2H); 2.0(m; 2H); 2.9(m; 2H); 3.2(m; 2H); 4.4(s; 1H); 5.2(m; 2H); 6.4(d; J=7.8 Hz; 1H); 6.5(dd; J=8.0; 2.1 Hz; 1H); 6.8(s; 1H); 6.9(s; 1H); 7.0(t; J=8.1 Hz; 1H); 7.3(m; 1H); 7.6(dd; J=6.8; 1.8 Hz; 1H) | ES+ 1471.3 | 6-methyl-N-[3-(4-piperidinyloxy)phenyl]-4'-trifluoromethoxy)[1,1'-biphenyl]-2-carboxamide |

TABLE 1-continued

| No. | STRUCTURES | MASS | NMR | NOMENCLATURE |
|---|---|---|---|---|
| 3 | 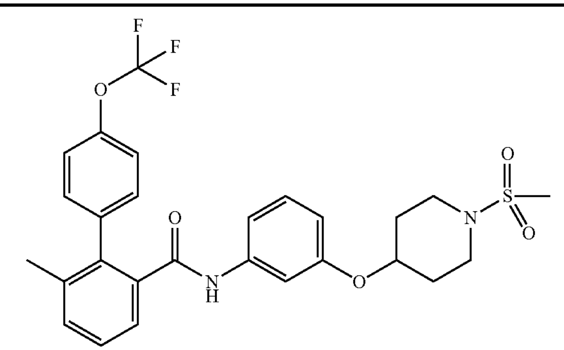 | ES− 547.2 | | 6-methyl-N-[3-[[1-(methylsulfonyl)-4-piperidinyl]oxy]phenyl]-4'-(trifluoromethoxy)[1,1'-biphenyl]-2-carboxamide |
| 4 | 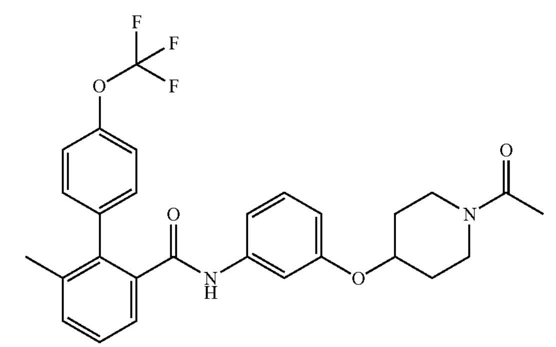 | ES+ 513.3 | | N-[3-[(1-acetyl-4-piperidinyl)oxy]phenyl]-6-methyl-4'-(trifluoromethoxy)[1,1'-biphenyl]-2-carboxamide |
| 5 | 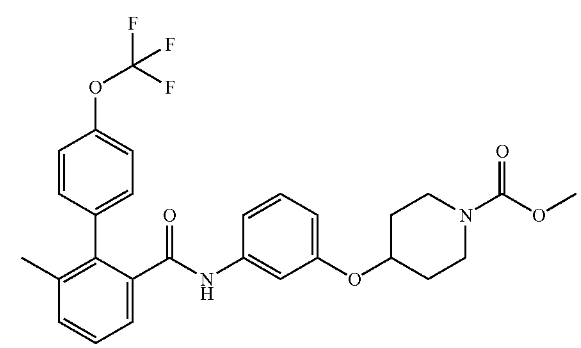 | | $^1$H NMR(300 MHz; Chloroform-D); δ ppm: 1.8(m; 4H); 2.2(s; 3H) 3.4(m; 2H); 3.7(m; 2H) 3.7(m; 3H); 4.4(m; 1H); 6.4(d; J=7.6 Hz; 1H); 6.6(dd; J=8.0; 2.1 Hz; 1H); 6.9(s; 1H); 7.1(m; 2H); 7.3(m; 6H); 7.6(dd; J=6.7; 2.1 Hz; 1H) | methyl 4-[3-[[[6-methyl-4'-(trifluoromethoxy)[1,1'-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 6 | 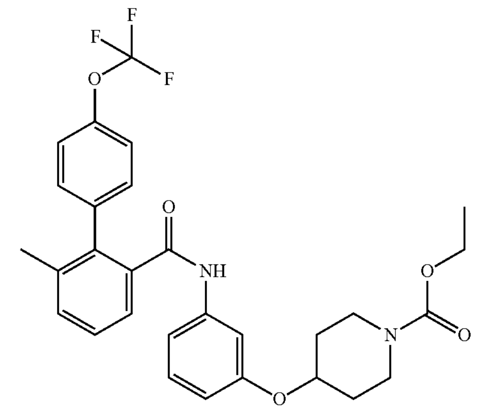 | ¹H NMR(300 MHz; DMSO-D6); δ ppm: 1.2(t; J=7.1 Hz; 3H); 1.5(m; 2H); 1.8(m; 2H); 2.1(s; 3H); 3.3(m; 2H); 3.6(m; 2H); 4.0(q; J=7.1 Hz; 2H); 4.4(m; 1H); 6.6(dd; J=8.0; 2.3 Hz; 1H); 6.9(d; J=8.0 Hz; 1H); 7.1(m; 2H); 7.4(m; 7H); 10.0(s; 1H) | ES+ 543.4 | ethyl 4-[3-[[[6-methyl-4'-(trifluoromethoxy)-[1,1'-biphenyl]-2-yl]carbonyl]amino]-phenoxy]-1-piperidinecarboxylate |
| 7 | 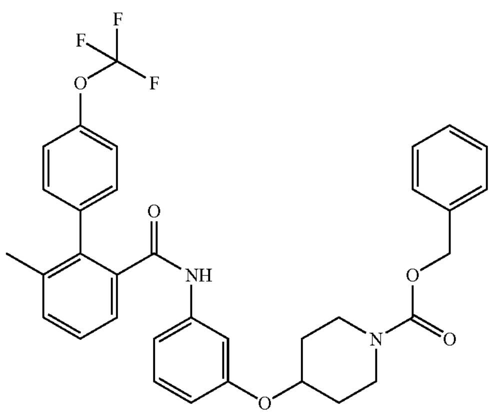 | ¹NMR(300 MHz; DMSO-D6); δ ppm: 1.5(m; 2H); 1.8(m; 2H); 2.1(s; 3H); 3.3(m; 2H); 3.7(m; 2H); 4.4(m; 1H); 5.1(s; 2H); 6.6(m; 1H); 6.9(d; J=7.6 Hz; 1H); 7.1(m; 2H); 7.4(m; 12H); 10.0(s; 1H) | ES+ 605.4 | phenylmethyl 4-[3-[[[6-methyl-4'-(trifluoromethoxy)[1,1'-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 8 | 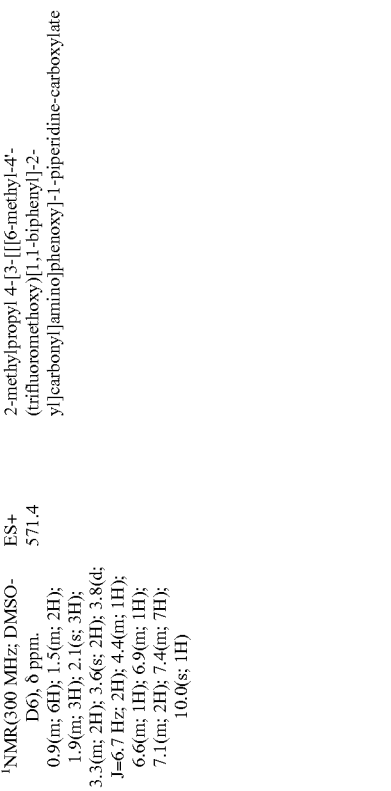 | $^1$NMR(300 MHz; DMSO-D6), δ ppm: 0.9(m; 6H); 1.5(m; 2H); 1.9(m; 3H); 2.1(s; 3H); 3.3(m; 2H); 3.6(s; 2H); 3.8(d; J=6.7 Hz; 2H); 4.4(m; 1H); 6.6(m; 1H); 6.9(m; 1H); 7.1(m; 2H); 7.4(m; 7H); 10.0(s; 1H) | ES+ 571.4 | 2-methylpropyl 4-[3-[[[6-methyl-4'-(trifluoromethoxy)][1,1'-biphenyl]-2-yl]carbonyl]amino]phenoxy]-1-piperidine-carboxylate |
| 9 | 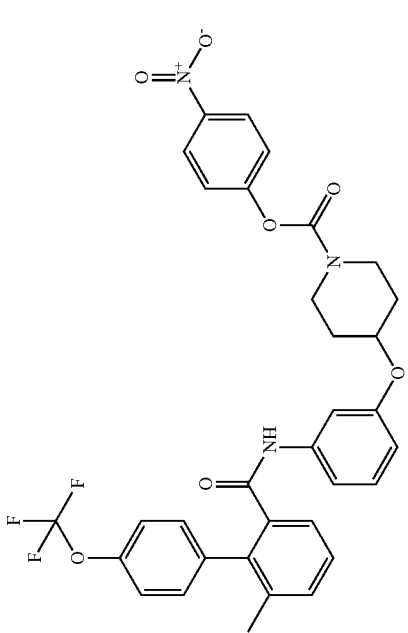 | $^1$H NMR(300 MHz; DMSO-D6); δ ppm: 1.7(m, 2H), 2.0(m, 2H); 2.1(s; 3H); 3.3(m; 2H); 3.8(m; J=45.2 Hz; 2H); 4.5(m; 1H); 6.7(m; 1H); 6.9(m; 1H); 7.1(m; 2H); 7.4(m; 9H); 8.3(m; 2H); 10.0(s; 1H) | ES− 634.4 | 4-nitrophenyl 4-[3-[[[6-methyl-4'-(trifluoromethoxy)[1,1'-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 10 | 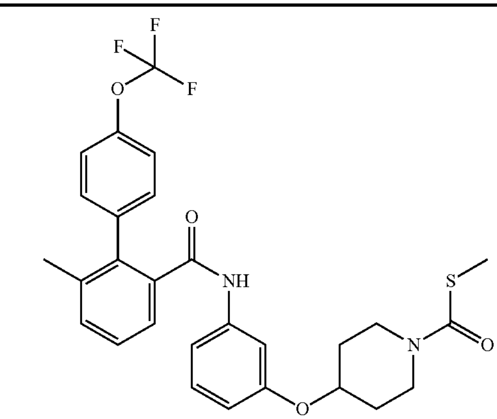 | | ES+ 545.3 | S-methyl 4-[3-[[[6-methyl-4'-(trifluoromethoxy)][1,1'-biphenyl]-2-yl]carbonyl]amino]phenoxy]-1-piperidinecarbothioate |
| 11 | 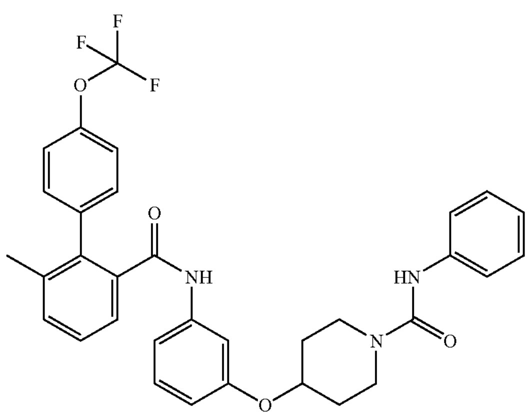 | $^1$H NMR(300 MHz; DMSO-D6); δ ppm: 1.6(m; 2H); 1.9(m; 2H); 2.1(s; 3H); 3.3(m; J=3.6 Hz; 2H); 3.7(m; 2H); 4.4(m; 1H); 6.7(m; 1H); 6.9(m; 2H); 7.2(m; 4H); 7.4(m; 9H); 8.5(s; 1H); 10.0(s; 1H) | AP+ 590.4 | 4-[3-[[[6-methyl-4'-(trifluoromethoxy)[1,1'-biphenyl]-2-yl]carbonyl]amino]phenoxy]-N-phenyl-1-piperidinecarboxamide |

TABLE 1-continued

| No. | STRUCTURES | NMR | MASS | NOMENCLATURE |
|---|---|---|---|---|
| 12 | 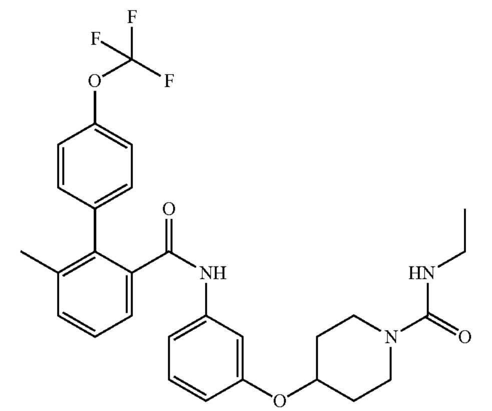 | ¹H NMR(300 MHz; DMSO-D6); δ ppm: 1.0(t; J=7.1 Hz; 3H); 1.4(m; 2H), 1.8(m, 2H) 2.1(s; 3H); 3.0(m; 4H); 3.6(m; 2H); 4.4(m; 1H); 6.5(m; 1H); 6.6(d; J=8.4 Hz; 2H); 7.1(m; 3H); 7.4(m; 7H); 10.0(s; 1H) | AP+ 542.4 | N-ethyl-4-[3-[[[6-methyl-4'-(trifluoromethoxy)[1,1'-biphenyl]-2-yl]carbonyl]amino]phenoxy]-1-piperidinecarboxamide |
| 13 | 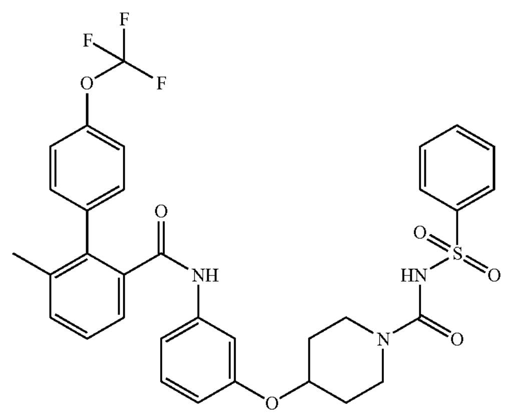 | ¹H NMR(300 MHz; DMSO-D6); δ ppm: 1.4(m; 2H); 1.8(m; 2H); 2.1(s; 3H); 3.1(m; 2H); 3.6(m; 2H); 4.4(m; 1H); 6.6(m; 1H); 7.00(m; 3H); 7.4(m; 10H); 7.8(m; 2H); 10.0(s; 1H); 11.1(m; 1H) | ES+ 654.2 | 4-[3-[[[6-methyl-4'-(trifluoromethoxy)[1,1'-biphenyl]-2-yl]carbonyl]amino]phenoxy]-N-(phenylsulfonyl)-1-piperidinecarbox-amide |

TABLE 1-continued

| No. | STRUCTURES | NMR | MASS | NOMENCLATURE |
|---|---|---|---|---|
| 14 | 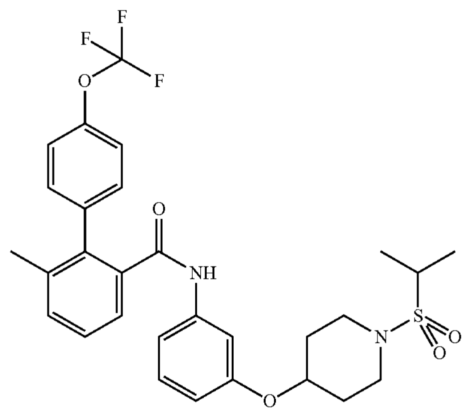 | | ES− 575.3 | 6-methyl-N-[3-[[1-[(1-methylethyl)sulfonyl]-4-piperidinyl]oxy]phenyl]-4'-(trifluoromethoxy)[1,1'-biphenyl]-2-carboxamide |
| 15 | 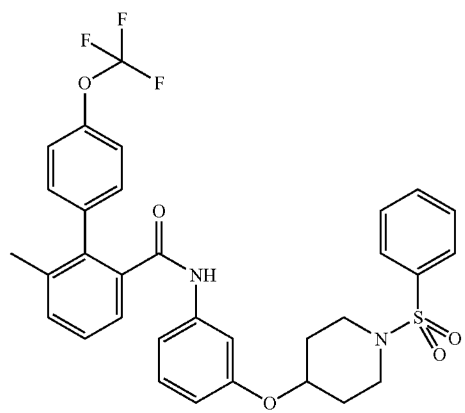 | | ES+ 611.3 | 6-methyl-N-[3-[[1-(phenylsulfonyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 16 | 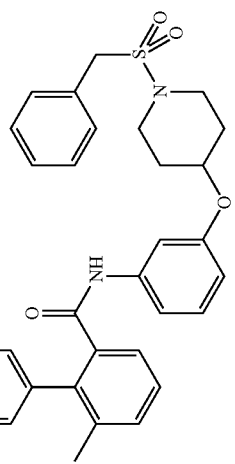 | | ES+ 625.3 | 6-methyl-N-[3-[[1-(phenylmethyl)sulfonyl]-4-piperidinyl]oxy]phenyl]-4'-(trifluoromethoxy)[1,1'-biphenyl]-2-carboxamide |
| 17 | 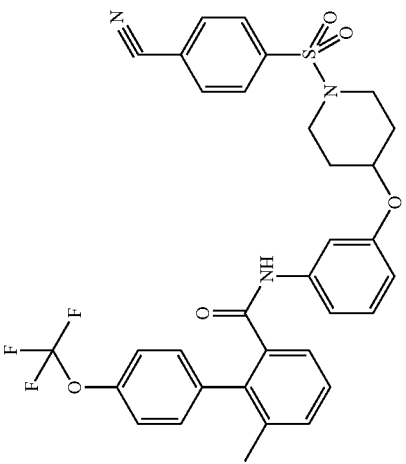 | | ES- 634.3 | N-[3-[[1-[(4-cyanophenyl)sulfonyl]-4-piperidinyl]oxy]phenyl]-6-methyl-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 18 | 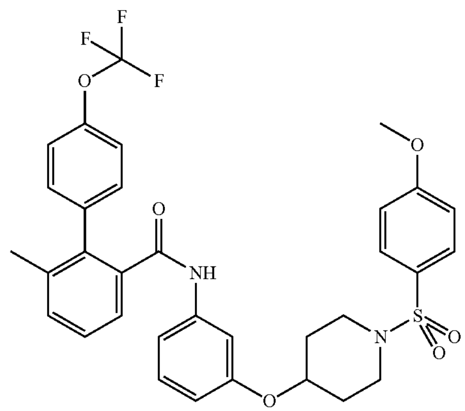 | | ES-639.3 | N-[3-[[1-[(4-methoxyphenyl)sulfonyl]-4-piperidinyl]oxy]phenyl]-6-methyl-4'-(trifluoromethoxy)[1,1'-biphenyl]-2-carboxamide |
| 19 | 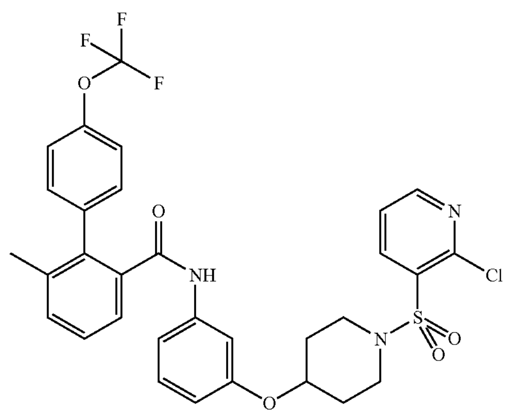 | | ES-644.3/646.3 1 Cl | N-[3-[[1-[(2-chloro-3-pyridinyl)sulfonyl]-4-piperidinyl]oxy]phenyl]-6-methyl-4'-(trifluoromethoxy)[1,1'-biphenyl]-2-carboxamide |

TABLE 1-continued

| No. | STRUCTURES | NMR | MASS | NOMENCLATURE |
|-----|------------|-----|------|--------------|
| 20 | 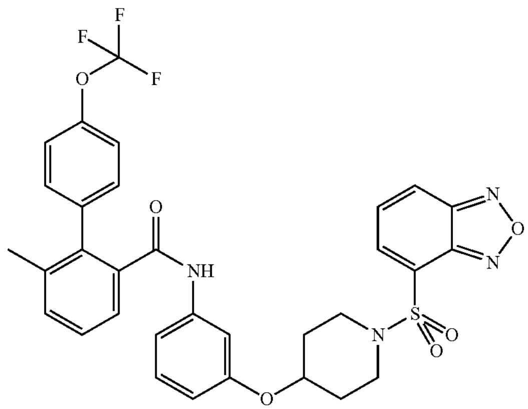 | | ES-651.2 | N-[3-[[1-(2,1,3-benzoxadiazol-4-yl-sulfonyl)-4-piperidinyl]oxy]phenyl]-6-methyl-4'-(trifluoromethoxy)[1,1'-biphenyl]-2-carboxamide |
| 21 | 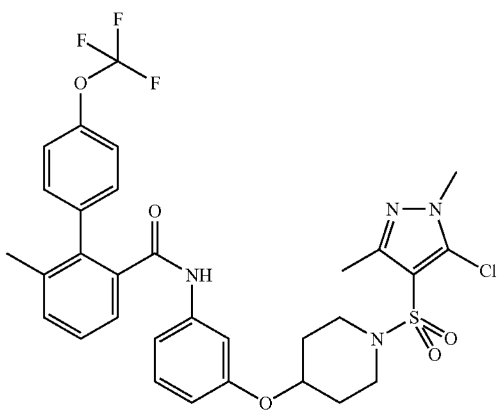 | | ES-663.3/665.3 1 Cl | N-[3-[[1-[(5-chloro-1,3-dimethyl-1H-pyrazol-4-yl)sulfonyl]-4-piperidinyl]oxy]phenyl]-6-methyl-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 22 | 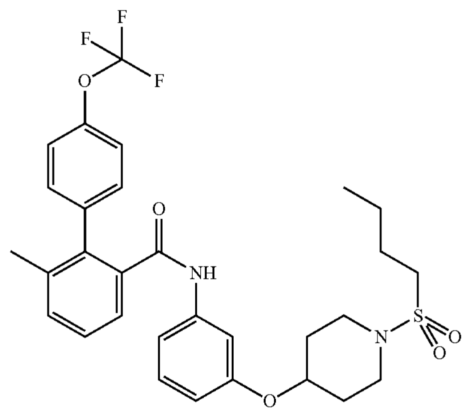 | | ES+ 591.4 | N-[3-[[1-(butylsulfonyl)-4-piperidinyl]oxy]-phenyl]-6-methyl-4-(trifluoromethoxy)-[1,1'-biphenyl]-2-carboxamide |
| 23 | 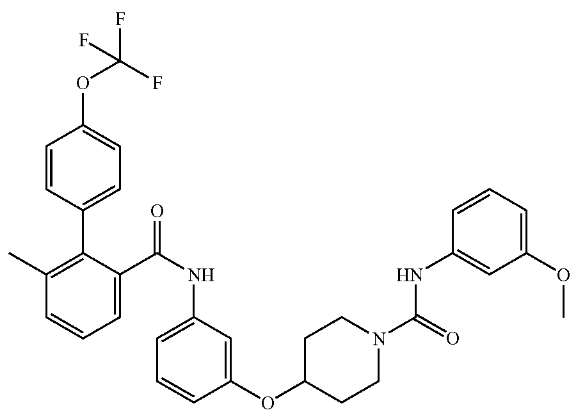 | | ES+ 620.3 | N-(3-methoxyphenyl)-4-[3-[[[6-methyl-4-(trifluoromethoxy)[1,1'-biphenyl]-2-yl]-carbonyl]amino]phenoxy]-1-piperidine-carboxamide |

TABLE 1-continued

| No. | STRUCTURES | NMR | MASS | NOMENCLATURE |
|---|---|---|---|---|
| 24 | 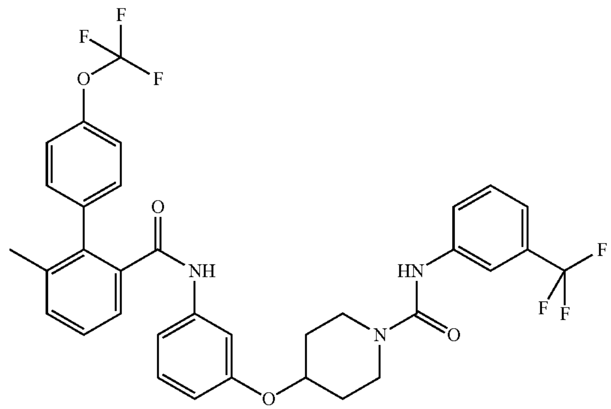 | | ES+ 658.3 | 4-[[[6-methyl-4-(trifluoromethoxy)[1,1'-4-biphenyl]-2-yl]carbonyl]amino]phenoxy]-N-[3-(trifluoromethyl)phenyl]-1-piperidinecarboxamide |
| 25 | 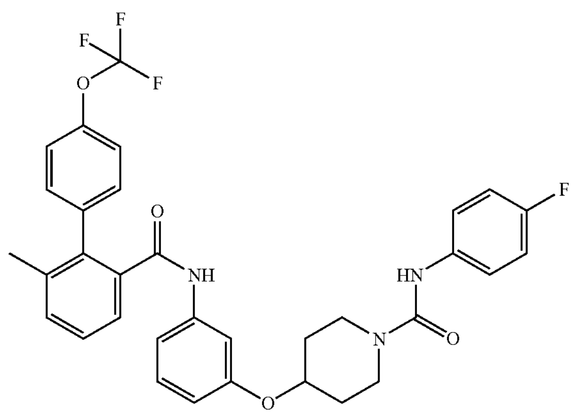 | | ES+ 606.3 | N-(4-fluorophenyl)-4-[3-[[[6-methyl-4-(trifluoromethoxy)[1,1'-biphenyl]-2-yl]carbonyl]amino]phenoxy]-1-piperidinecarboxamide |

TABLE 1-continued
| No. | STRUCTURES | NMR | MASS | NOMENCLATURE |
|---|---|---|---|---|
| 26 | 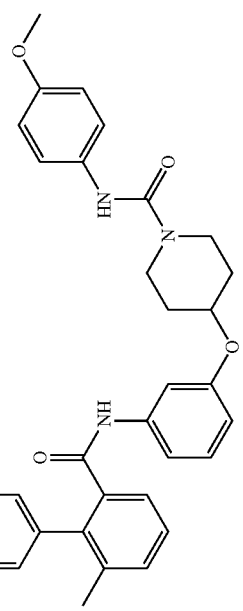 | | ES− 618.3 | N-(4-methoxyphenyl)-4-[3-[[[6-methyl-4'-(trifluoromethoxy)][1,1'-biphenyl]-2-yl]-carbonyl]amino]phenoxyl]-1-piperidine-carboxamide |
| 27 | 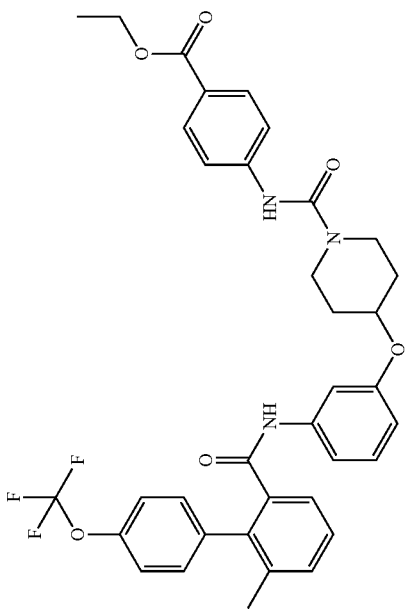 | | ES− 660.3 | ethyl 4-[[[4-[3-[[[6-methyl-4'-(trifluoromethoxy)][1,1'-biphenyl]-2-yl]carbonyl]amino]-phenoxy]-1-piperidinyl]carbonyl]amino]-benzoate |

TABLE 1-continued

| No. | STRUCTURES | NMR | MASS | NOMENCLATURE |
|---|---|---|---|---|
| 28 | 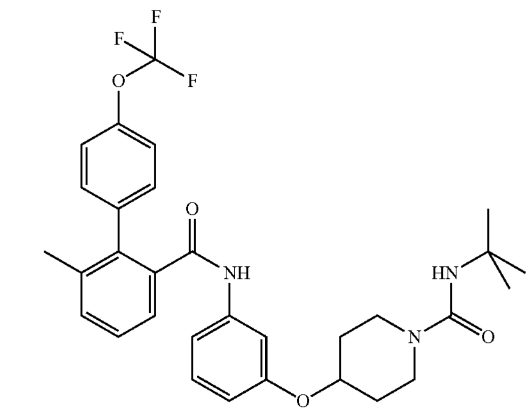 | | ES+ 570.3 | N-(1,1-dimethylethyl)-4-[3-[[[6-methyl-4'-(trifluoromethoxy)[1,1'-biphenyl]-2-yl]-carbonyl]amino]phenoxy]-1-piperidine-carboxamide |
| 29 | 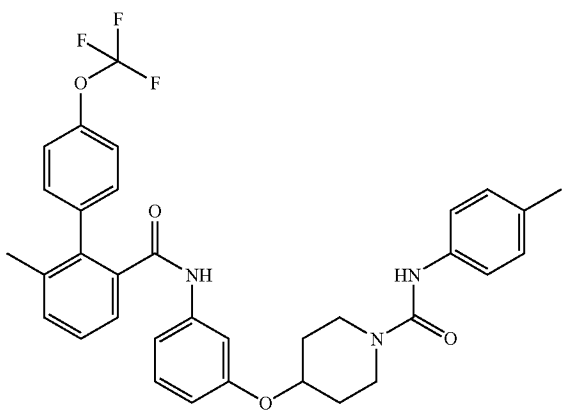 | | ES- 602.3 | N-(4-methylphenyl)-4-(3-[[[6-methyl-4'-(trifluoromethoxy)[1,1'-biphenyl]-2-yl]-carbonyl]amino]phenoxy]-1-piperidine-carboxamide |

TABLE 1-continued
| No. | STRUCTURES | NMR | MASS | NOMENCLATURE |
|---|---|---|---|---|
| 30 | 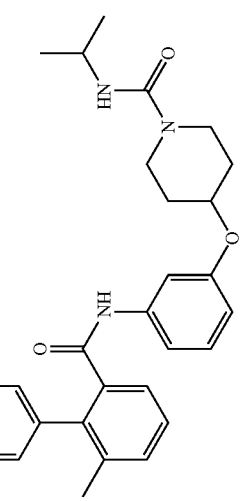 | | ES-554.3 | N-(1-methylethyl)-4-[3-[[[6-methyl-4'-(trifluoromethoxy)[1,1'-biphenyl]-2-yl]carbonyl]amino]phenoxy]-1-piperidinecarboxamide |
| 31 | 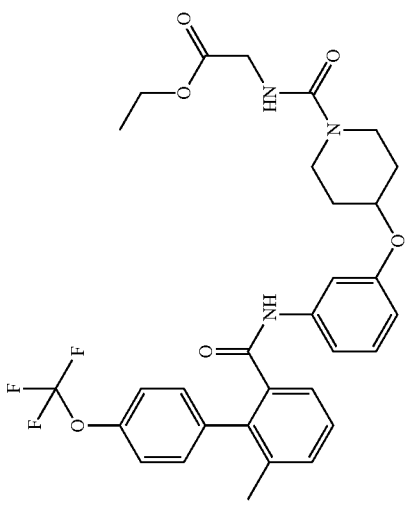 | | ES-598.3 | ethyl N-[[4-[3-[[[6-methyl-4'-(trifluoromethoxy)[1,1'-biphenyl]-2-yl]carbonyl]amino]phenoxy]-1-piperidinyl]carbonyl]glycinate |

TABLE 1-continued
| No. | STRUCTURES | NMR | MASS | NOMENCLATURE |
|---|---|---|---|---|
| 32 | 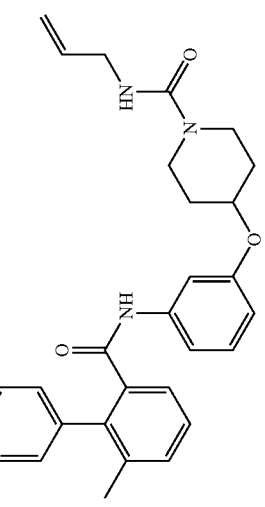 | | ES–552.3 | 4-[3-[[[6-methyl-4'-(trifluoromethoxy)[1,1'-biphenyl]-2-yl]carbonyl]amino]phenoxy]-N-2-propenyl-1-piperidinecarboxamide |
| 33 | 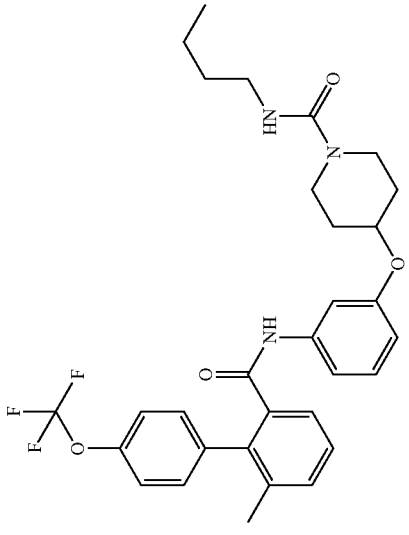 | | ES–568.3 | N-butyl-4-[3-[[[6-methyl-4'-(trifluoromethoxy)[1,1'-biphenyl]-2-yl]carbonyl]amino]phenoxy]-1-piperidinecarboxamide |

TABLE 1-continued

| No. | STRUCTURES | NMR | MASS | NOMENCLATURE |
|---|---|---|---|---|
| 34 | 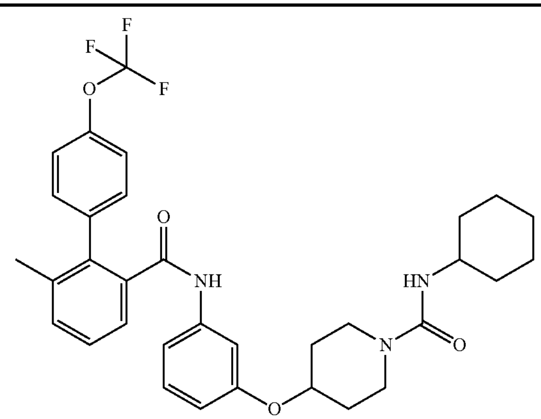 | | ES-594.3 | N-cyclohexyl-4-[3-[[[6-methyl-4'-(trifluoromethoxy)[1,1'-biphenyl]-2-yl]carbonyl]amino]phenoxy]-1-piperidinecarboxamide |
| 35 | 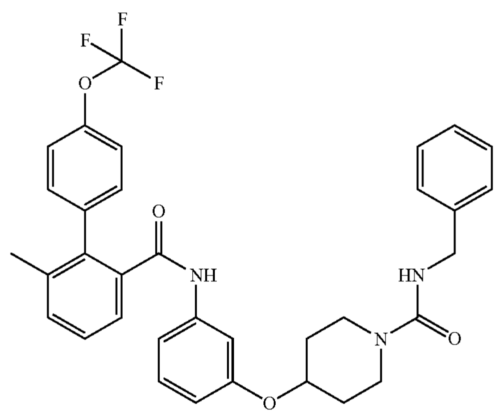 | | ES-602.3 | 4-[3-[[[6-methyl-4'-(trifluoromethoxy)[1,1'-biphenyl]-2-yl]carbonyl]amino]phenoxy]-N-(phenylmethyl)-1-piperidinecarboxamide |

TABLE 1-continued
| No. | STRUCTURES | NMR | MASS | NOMENCLATURE |
|---|---|---|---|---|
| 36 | 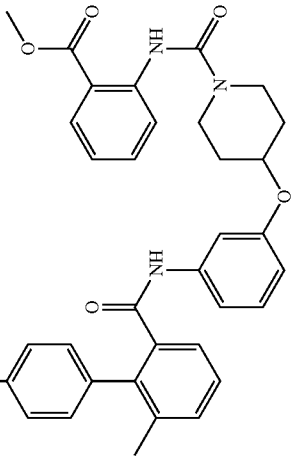 | | ES– 646.3 | methyl 2-[[[4-[3-[[[6-methyl-4'-(trifluoromethoxy)[1,1'-biphenyl]-2-yl]carbonyl]-amino]phenoxy]-1-piperidinyl]carbonyl]-amino]benzoate |
| 37 | 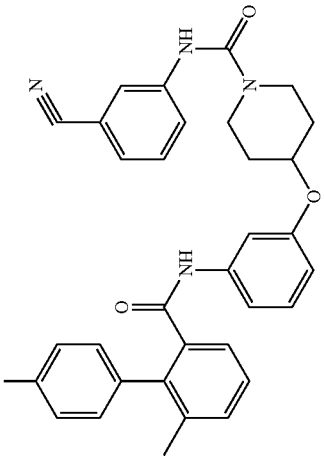 | | ES– 613.3 | N-(3-cyanophenyl)-4-[3-[[[6-methyl-4'-(trifluoromethoxy)[1,1'-biphenyl]-2-yl]carbonyl]amino]phenoxy]-1-piperidine-carboxamide |

TABLE 1-continued
| No. | STRUCTURES | NMR | MASS | NOMENCLATURE |
|---|---|---|---|---|
| 38 | 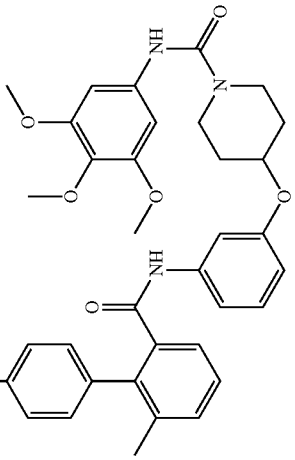 | | ES−678.4 | 4-[3-[[[6-methyl-4'-(trifluoromethoxy)[1,1'-biphenyl]-2-yl]carbonyl]amino]phenoxy]-N-(3,4,5-trimethoxyphenyl)-1-piperidine-carboxamide |
| 39 | 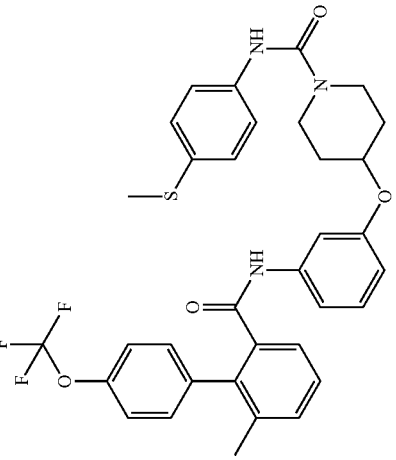 | | ES−634.3 | N-[4-(methylthio)phenyl]-4-[3-[[[6-methyl-4'-(trifluoromethoxy)[1,1'-biphenyl]-2-yl]carbonyl]amino]phenoxy]-1-piperidine-carboxamide |

TABLE 1-continued
| No. | STRUCTURES | NMR | MASS | NOMENCLATURE |
|---|---|---|---|---|
| 40 | 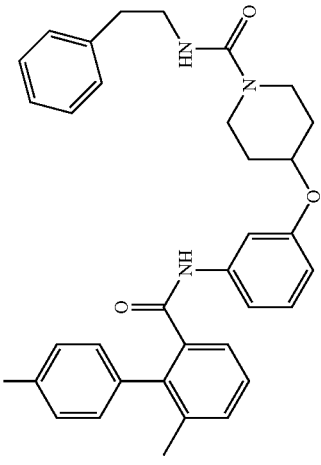 | | ES-616.3 | 4-[[[6-methyl-4'-(trifluoromethoxy)[1,1'-biphenyl]-2-yl]carbonyl]amino]phenoxy]-N-(2-phenylethyl)-1-piperidinecarboxamide |
| 41 | 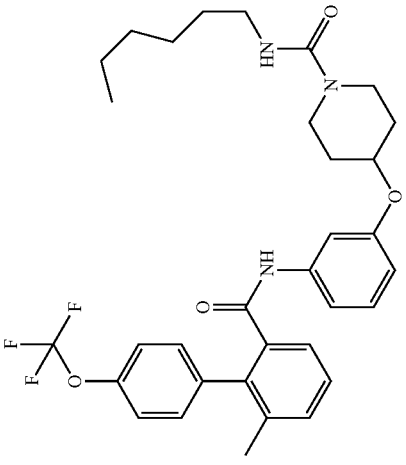 | | ES-596.4 | N-hexyl-4-[3-[[[6-methyl-4'-(trifluoromethoxy)[1,1'-biphenyl]-2-yl]carbonyl]amino]-phenoxy]-1-piperidinecarboxamide |

TABLE 1-continued
| No. | STRUCTURES | NMR | MASS | NOMENCLATURE |
|---|---|---|---|---|
| 42 | 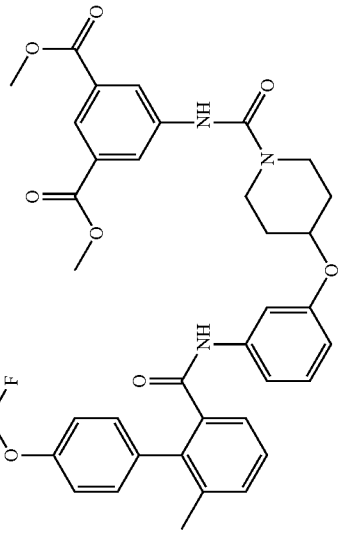 | | ES- 704.3 | dimethyl 5-[[[4-[3-[[[6-methyl-4'-(trifluoromethoxy)[1,1'-biphenyl]-2-yl]carbonyl]amino]phenoxy]-1-piperidinyl]carbonyl]amino]-1,3-benzenedicarboxylate |
| 43 | 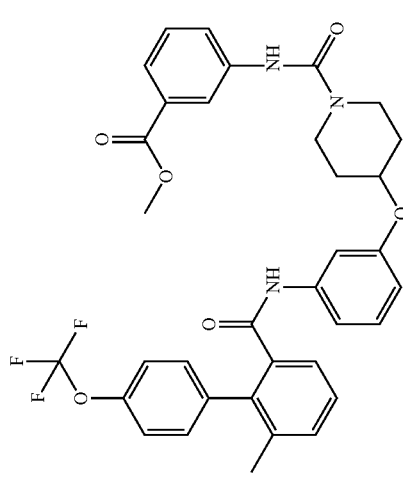 | | ES- 646.3 | methyl 3-[[[4-[3-[[[6-methyl-4'-(trifluoromethoxy)[1,1'-biphenyl]-2-yl]carbonyl]amino]phenoxy]-1-piperidinyl]carbonyl]amino]benzoate |

TABLE 1-continued

| No. | STRUCTURES | NMR | MASS | NOMENCLATURE |
|---|---|---|---|---|
| 44 | 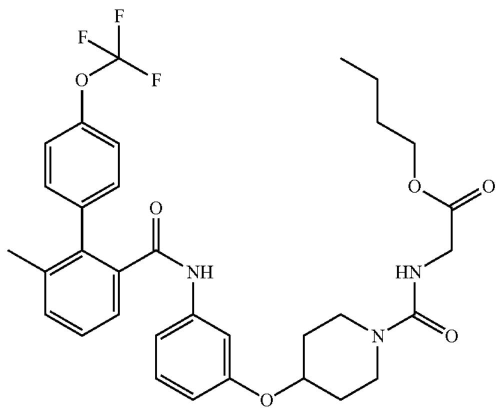 | | ES− 626.3 | butyl N-[[4-[3-[[[6-methyl-4'-(trifluoromethoxy)[1,1'-biphenyl]-2-yl]carbonyl]amino]phenoxy]-1-piperidinyl]carbonyl]glycinate |
| 45 | 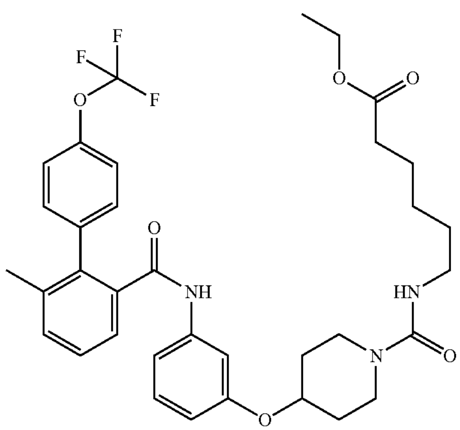 | | ES− 654.4 | ethyl 6-[[[4-[3-[[[6-methyl-4'-(trifluoromethoxy)[1,1'-biphenyl]-2-yl]carbonyl]amino]phenoxy]-1-piperidinyl]carbonyl]amino]hexanoate |

TABLE 1-continued
| No. | STRUCTURES | NMR | MASS | NOMENCLATURE |
|---|---|---|---|---|
| 46 | 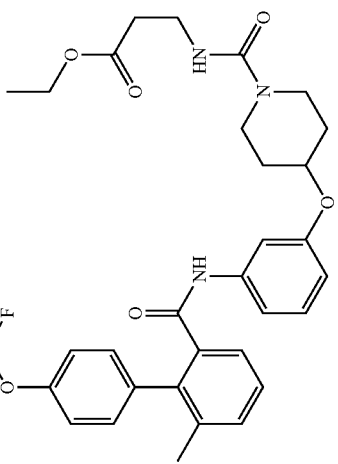 | | ES-612.3 | ethyl N-[[4-[3-[[[6-methyl-4'-(trifluoromethoxy)[1,1'-biphenyl]-2-yl]carbonyl]amino]phenoxy]-1-piperidinyl]carbonyl]-β-alaninate |
| 47 | 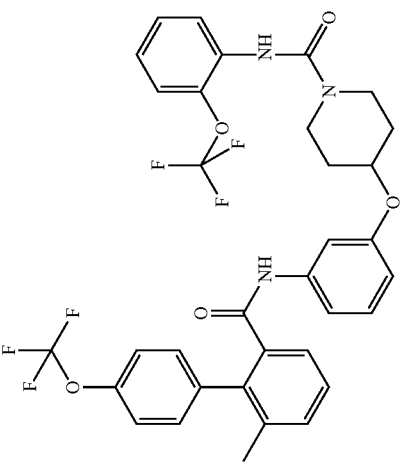 | | ES-672.3 | 4-[3-[[[6-methyl-4'-(trifluoromethoxy)[1,1'-biphenyl]-2-yl]carbonyl]amino]phenoxy]-N-(2-(trifluoromethoxy)phenyl]-1-piperidinecarboxamide |

TABLE 1-continued
| No. | STRUCTURES | MASS | NMR | NOMENCLATURE |
|---|---|---|---|---|
| 48 | 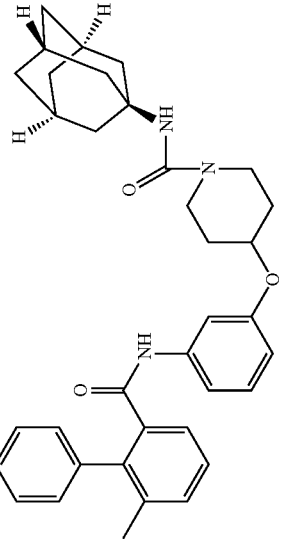 | ES-646.4 | | 4-[3-[[[6-methyl-4'-(trifluoromethoxy)[1,1'-biphenyl]-2-yl]carbonyl]amino]phenoxy]-N-tricyclo[3.3.1.1~3,7~]dec-1-yl-1-piperidinecarboxamide |
| 49 | 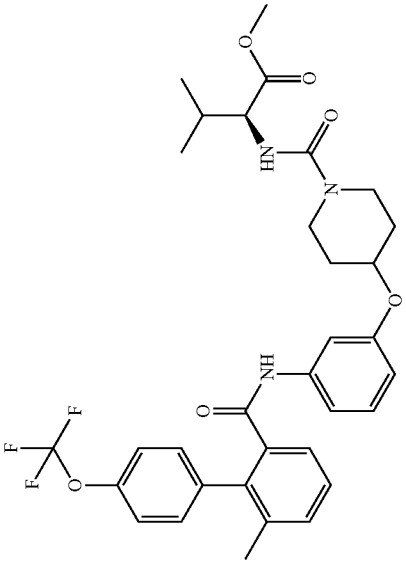 | ES-626.3 | | methyl N-[[4-[3-[[[6-methyl-4'-(trifluoromethoxy)[1,1'-biphenyl]-2-yl]carbonyl]amino]phenoxy]-1-piperidinyl]carbonyl]-L-valinate |

TABLE 1-continued
| No. | STRUCTURES | NMR | MASS | NOMENCLATURE |
|---|---|---|---|---|
| 50 | 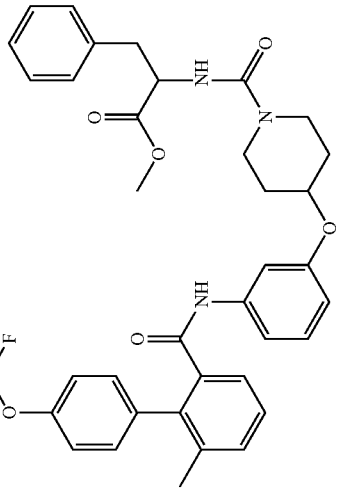 | | ES− 674.3 | methyl N-[4-[[6-methyl-4'-(trifluoromethoxy)[1,1'-biphenyl]-2-yl][carbonyl]amino]phenoxy]-1-piperidinyl]carbonyl]-phenylalaninate |
| 51 | 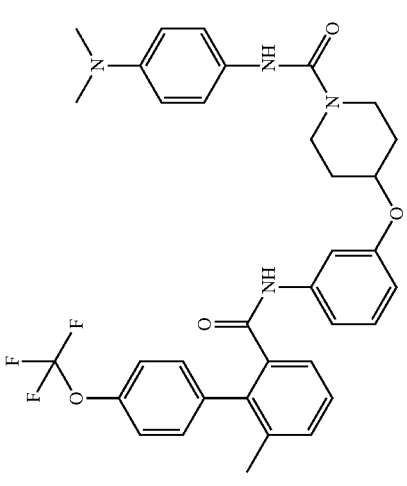 | | ES+ 633.4 | N-[4-(dimethylamino)phenyl]-4-[3-[[[6-methyl-4'-(trifluoromethoxy)[1,1'-biphenyl]-2-yl]carbonyl]amino]phenoxy]-1-piperidinecarboxamide |

TABLE 1-continued

| No. | STRUCTURES | NMR | MASS | NOMENCLATURE |
|---|---|---|---|---|
| 52 | 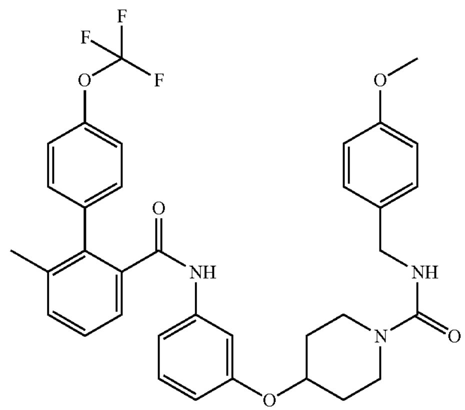 | | ES-632.4 | N-[(4-methoxyphenyl)methyl]-4-[3-[[[6-methyl-4'-(trifluoromethoxy)[1,1'-biphenyl]-2-yl]carbonyl]amino]phenoxy]-1-piperidinecarboxamide |
| 53 | 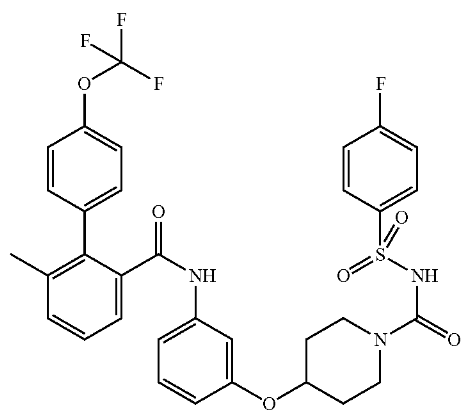 | | ES-670.3 | N-[(4-fluorophenyl)sulfonyl]-4-[3-[[[6-methyl-4'-(trifluoromethoxy)[1,1'-biphenyl]-2-yl]carbonyl]amino]phenoxy]-1-piperidinecarboxamide |

| No. | STRUCTURES | NMR | MASS | NOMENCLATURE |
| --- | --- | --- | --- | --- |
| 54 | 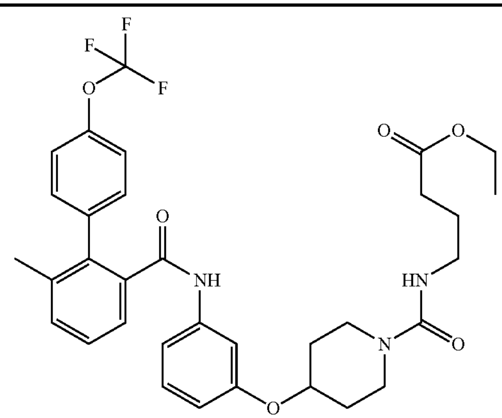 | | ES-626.3 | ethyl 4-[[[4-[3-[[[6-methyl-4'-(trifluoro-methoxy)[1,1'-biphenyl]-2-yl]carbonyl]-amino]phenoxy]-1-piperidinyl]carbonyl]-amino]butanoate |
| 55 | 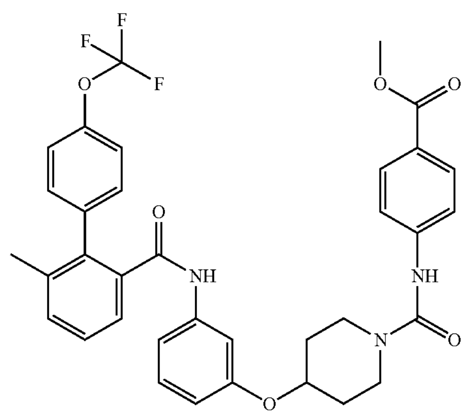 | | ES-646.3 | methyl 4-[[[4-[3-[[[6-methyl-4'-(trifluoro-methoxy)[1,1'-biphenyl]-2-yl]carbonyl]-amino]phenoxy]-1-piperidinyl]carbonyl]-amino]benzoate |

TABLE 1-continued
| No. | STRUCTURES | NMR | MASS | NOMENCLATURE |
|---|---|---|---|---|
| 56 | 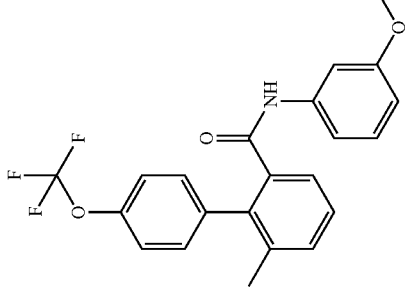 | | ES-632.3 | N-1,3-benzodioxol-5-yl-4-[3-[[[6-methyl-4'-(trifluoromethoxy)[1,1'-biphenyl]-2-yl]-carbonyl]amino]phenoxy]-1-piperidine-carboxamide |
| 57 | 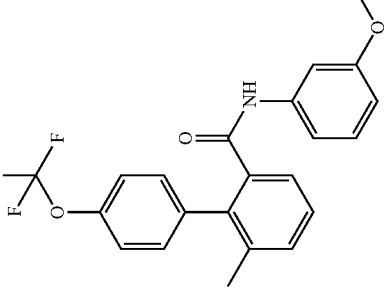 | | ES-580.3 | N-cyclopentyl-4-[3-[[[6-methyl-4'-(trifluoromethoxy)[1,1'-biphenyl]-2-yl]carbonyl]amino]phenoxy]-1-piperidinecarboxamide |

TABLE 1-continued

| No. | STRUCTURES | NMR | MASS | NOMENCLATURE |
|---|---|---|---|---|
| 58 | 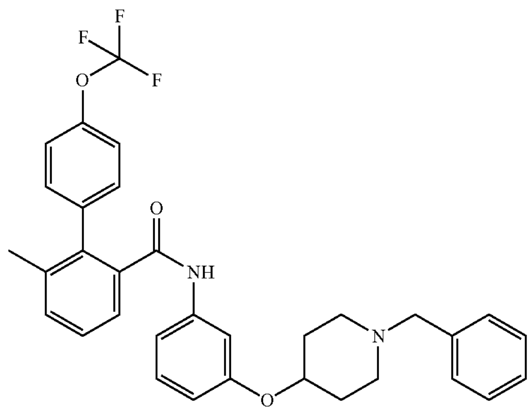 | | ES+ 561.4 | [1,1'-biphenyl]-6-methyl-N-[3-[[1-(phenyl-methyl)-4-piperidinyl]oxy]phenyl]-4'-(trifluoromethoxy)-2-carboxamide |
| 59 | 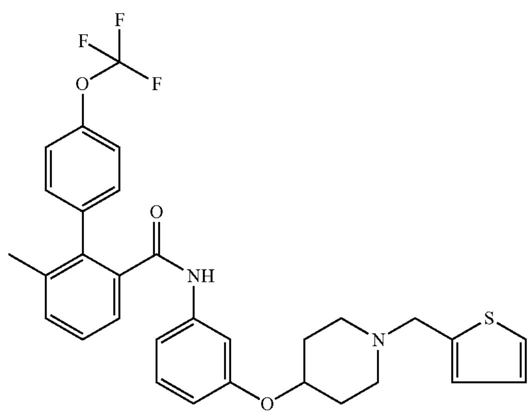 | | ES+ 567.4 | [1,1'-biphenyl]-6-methyl-N-[3-[[1-(2-thienylmethyl)-4-piperidinyl]oxy]phenyl]-4'-(trifluoromethoxy)-2-carboxamide |

TABLE 1-continued

| No. | STRUCTURES | NMR | MASS | NOMENCLATURE |
|---|---|---|---|---|
| 60 | 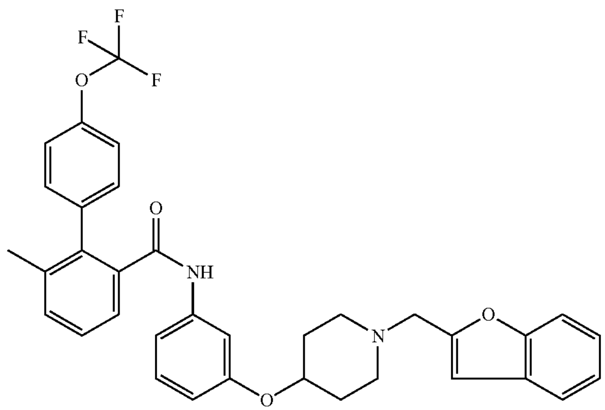 | | ES+ 601.4 | N-[3-[[1-(2-benzofuranylmethyl)-4-piperidinyl]oxy]phenyl]-6-methyl-4'-(trifluoromethoxy)-[1,1'-biphenyl]-2-carboxamide |
| 61 | 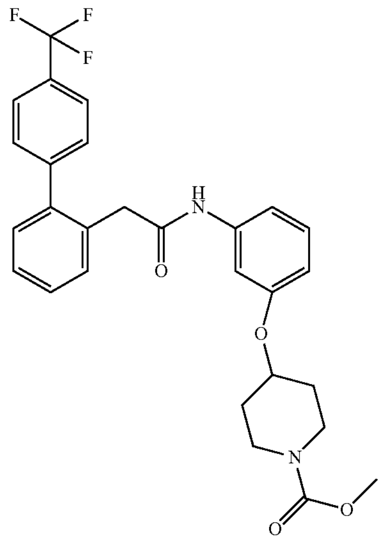 | ¹H NMR(300 MHz; Chloroform-D); δ ppm: 1.3(m; 6 H); 3.5(m; 7 H); 4.4(m; 1 H) 6.7(m; 3 H); 7.4(m; 10 H) | ES− 511.2 | methyl 4-[3-[[[4'-(trifluoromethyl)[1,1'-biphenyl]-2-yl]acetyl]amino]phenoxy]-1-piperidinecarboxylate |

TABLE 1-continued

| No. | STRUCTURES | NMR | MASS | NOMENCLATURE |
|---|---|---|---|---|
| 62 | 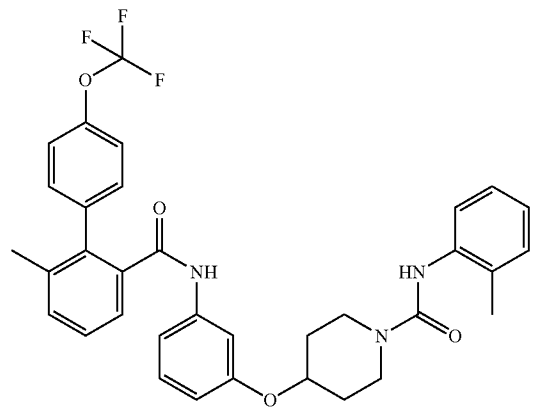 | | ES− 602.3 | N-(2-methylphenyl)-4-[3-[[[(6-methyl-4'-(trifluoromethoxy)][1,1'-biphenyl]-2-yl]carbonyl]amino]phenoxy]-1-piperidinecarboxamide |
| 63 | 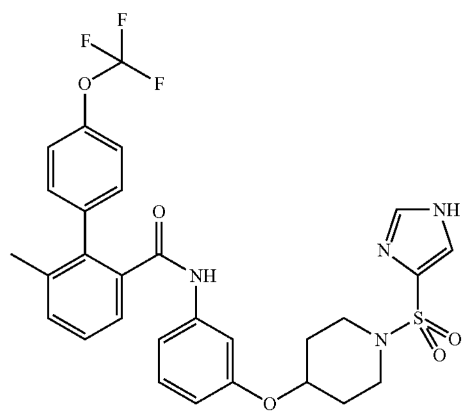 | | ES+ 601.2 | N-[3-[[1-(1H-imidazol-4-ylsulfonyl)-4-piperidinyl]oxy]phenyl]-6-methyl-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 64 | 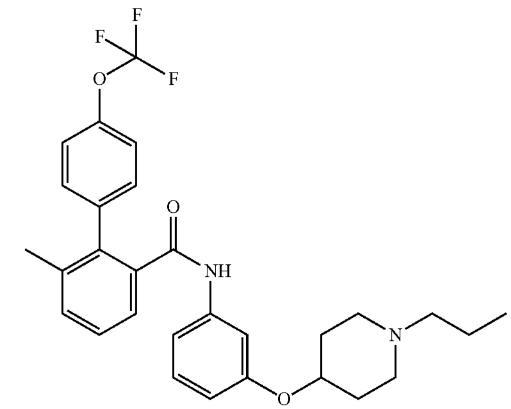 | | ES+ 513.3 | 6-methyl-N-[3-[(1-propyl-4-piperidinyl)-oxy]phenyl]-4'-(trifluoromethoxy)[1,1'-biphenyl]-2-carboxamide |
| 65 | 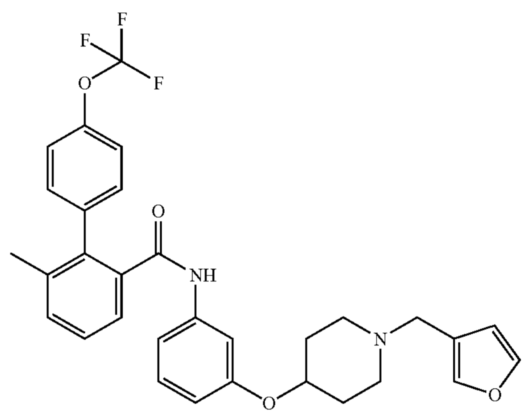 | | ES+ 551.3 | N-[3-[[1-(3-furanylmethyl)-4-piperidinyl]-oxy]phenyl]-6-methyl-4'-(trifluorometh-oxy)[1,1'-biphenyl]-2-carboxamide |

TABLE 1-continued

| No. | STRUCTURES | NMR | MASS | NOMENCLATURE |
|---|---|---|---|---|
| 66 | 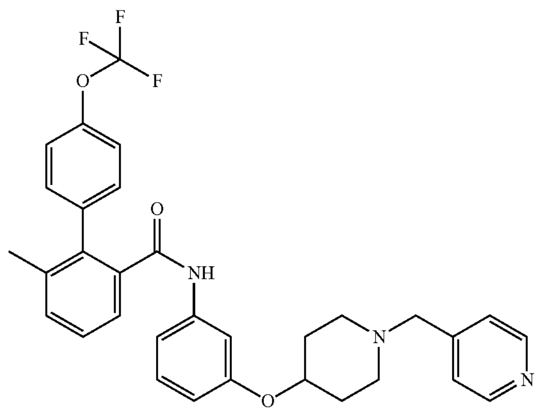 | | ES+ 562.3 | 6-methyl-N-[3-[[1-(4-pyridinylmethyl)-4-piperidinyl]oxy]phenyl]-4'-(trifluoromethoxy)[1,1'-biphenyl]-2-carboxamide |
| 67 | 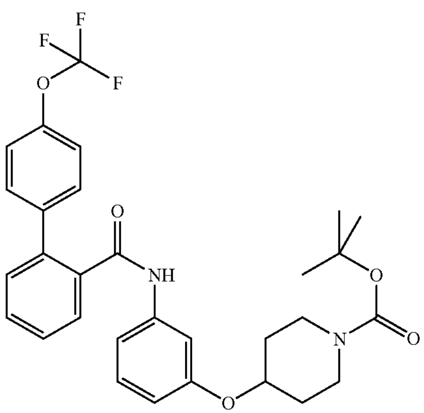 | | ES+ 557.3 | 1,1-dimethylethyl 4-[3-[[[[4'-(trifluoromethoxy)[1,1'-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 68 | 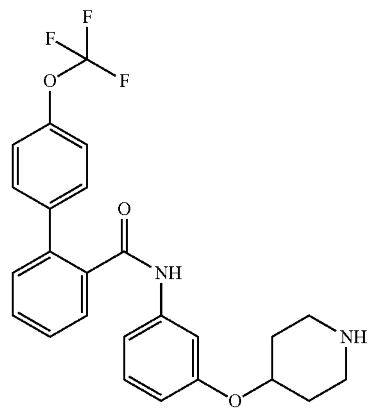 | | ES+ 457.2 | N-[3-(4-piperidinyloxy)phenyl]-4'-(trifluoromethoxy)[1,1'-biphenyl]-2-carboxamide |
| 69 | 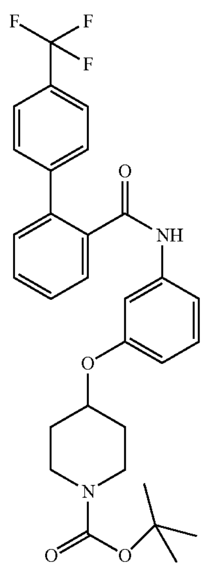 | | ES− 539.3 | 1,1-dimethylethyl 4-[3-[[[4-(trifluoromethyl)[1,1'-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 70 | 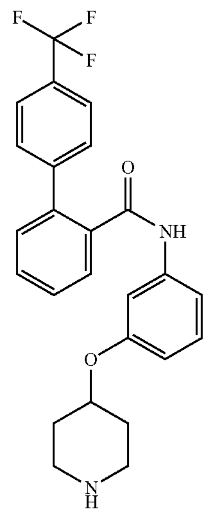 | | ES+ 441.3 | N-[3-(4-piperidinyloxy)phenyl]-4'-(trifluoromethyl)[1,1'-biphenyl]-2-carboxamide |
| 71 | 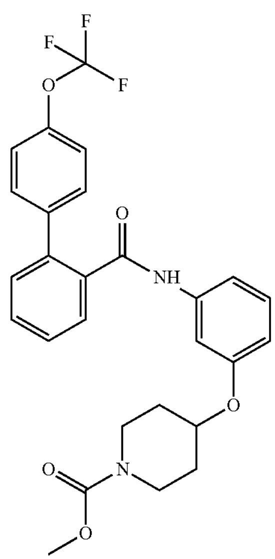 | | ES+ 515.2 | methyl 4-[3-[[[4'-(trifluoromethoxy)[1,1'-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 72 | 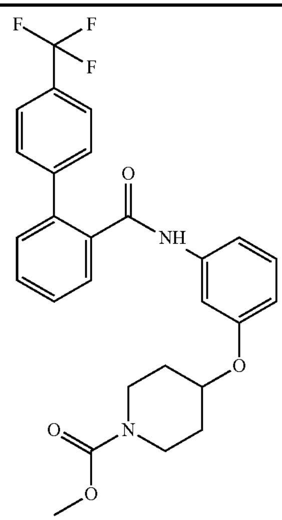 | | ES+ 499.2 | methyl 4-[[[4'-(trifluoromethyl)[1,1'-biphenyl]-2-yl]carbonyl]amino]phenoxy]-1-piperidinecarboxylate |
| 73 | 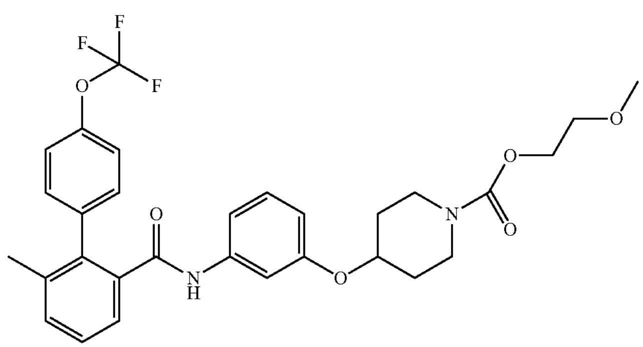 | | ES+ 573.2 | 2-methoxyethyl 4-[3-[[[6-methyl-4'-(trifluoromethoxy)[1,1'-biphenyl]-2-yl]carbonyl]amino]phenoxy]-1-piperidine-carboxylate |

TABLE 1-continued
| No. | STRUCTURES | NMR | MASS | NOMENCLATURE |
|---|---|---|---|---|
| 74 | 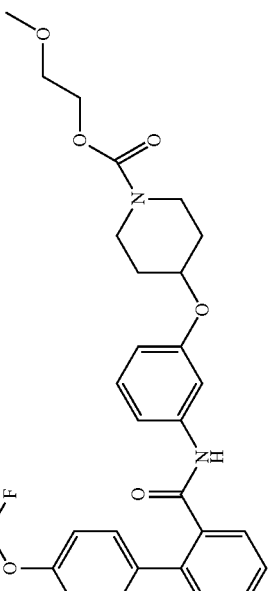 | | ES+ 559.2 | 2-methoxyethyl 4-[3-[[[4'-(trifluoromethoxy)[1,1'-biphenyl]-2-carbonyl]amino]phenoxy]-1-piperidinecarboxylate |
| 75 | 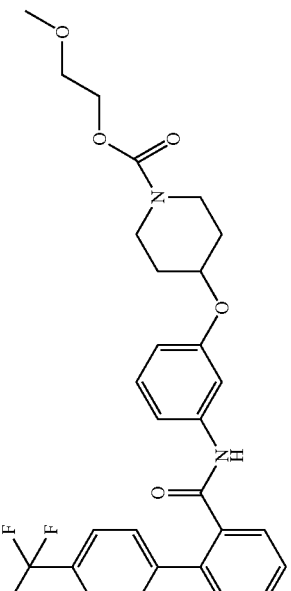 | | ES+ 543.2 | 2-methoxyethyl 4-[3-[[[4'-(trifluoromethyl)-[1,1'-biphenyl]-2-yl]carbonyl]amino]phenoxy]-1 piperidinecarboxylate |

TABLE 1-continued

| No. | STRUCTURES | NMR | MASS | NOMENCLATURE |
|---|---|---|---|---|
| 76 | 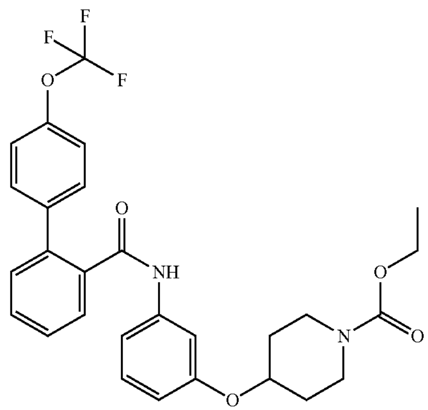 | | ES+ 529.2 | ethyl 4-[3-[[[4'-(trifluoromethoxy)[1,1'-biphenyl]-2-yl]carbonyl]amino]phenoxy]-1-piperidinecarboxylate |
| 77 | 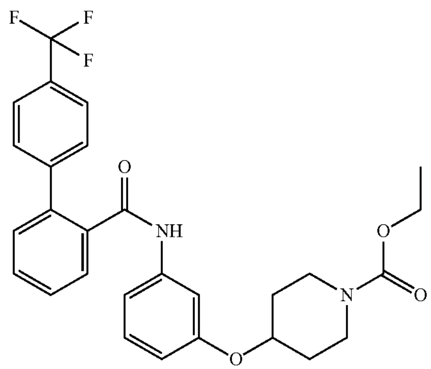 | | ES+ 513.2 | ethyl 4-[3-[[[4'-(trifluoromethyl)[1,1'-biphenyl]-2-yl]carbonyl]amino]phenoxy]-1-piperidinecarboxylate |

TABLE 1-continued
| No. | STRUCTURES | NMR | MASS | NOMENCLATURE |
|---|---|---|---|---|
| 78 | 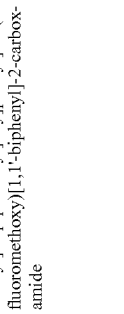 | | ES+ 555.3 | 6-methyl-N-[3-[[1-[(tetrahydro-3-furanyl)-methyl]-4-piperidinyl]oxy]phenyl]-4'-(tri-fluoromethoxy)[1,1'-biphenyl]-2-carbox-amide |
| 79 | 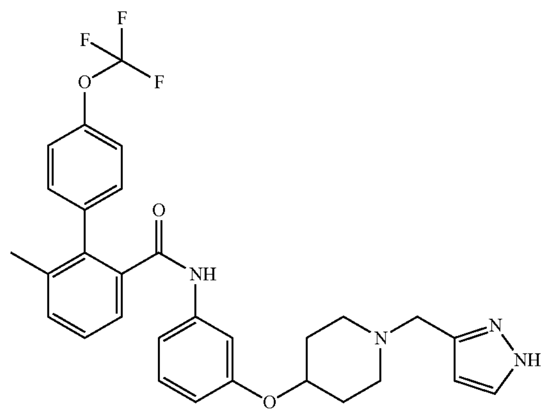 | | ES+ 551.3 | 6-methyl-N-[3-[[1-(1H-pyrazol-3-ylmethyl)-4-piperidinyl]oxy]phenyl]-4'-(trifluoro-methoxy)[1,1'-biphenyl]-2-carboxamide |

TABLE 1-continued
| No. | STRUCTURES | NMR | MASS | NOMENCLATURE |
|---|---|---|---|---|
| 80 | 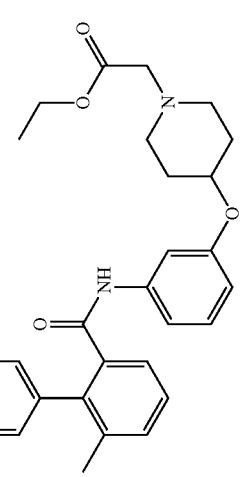 | | ES+ 557.3 | ethyl 4-[3-[[[6-methyl-4'-(trifluoromethoxy)-[1,1'-biphenyl]-2-yl]carbonyl]amino]-phenoxy]-1-piperidineacetate |
| 81 | 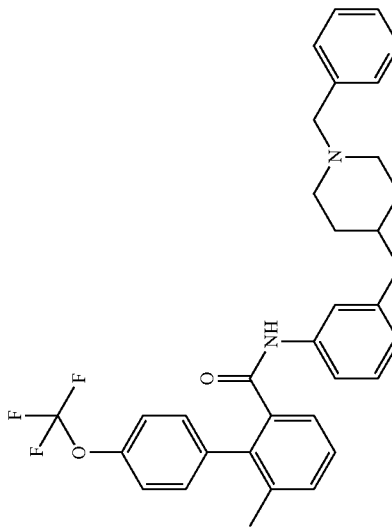 | | ES+ 562.3 | 6-methyl-N-[3-[[1-(3-pyridinylmethyl)-4-piperidinyl]oxy]phenyl]-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 82 | 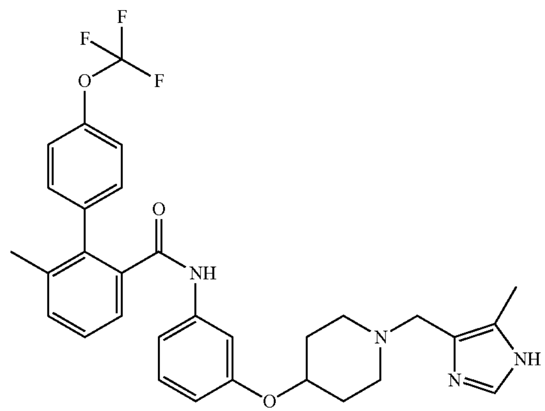 | | ES+ 565.3 | 6-methyl-N-[3-[[1-[(5-methyl-1H-imidazol-4-yl)methyl]-4-piperidinyl]oxy]phenyl]-4'-(trifluoromethoxy)[1,1'-biphenyl]-2-carboxamide |
| 83 | 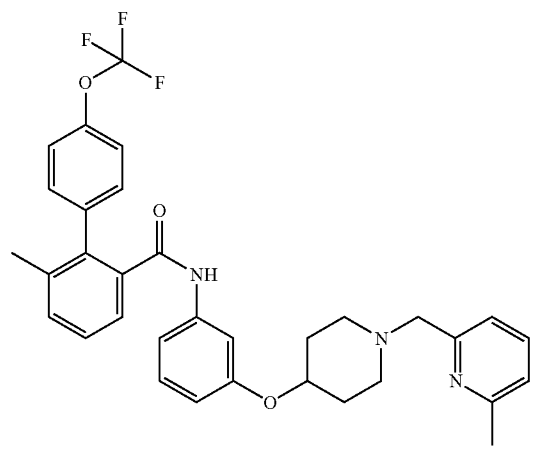 | | ES+ 576.3 | 6-methyl-N-[3-[[1-[(6-methyl-2-pyridinyl)methyl]-4-piperidinyl]oxy]phenyl]-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 84 | 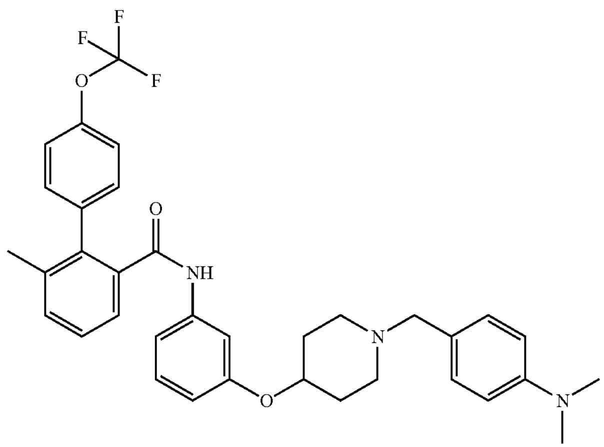 | | ES+ 604.4 | N-[3-[[1-[[4-(dimethylamino)phenyl]-methyl]-4-piperidinyl]oxy]phenyl]-6-methyl-4'-(trifluoromethoxy)[1,1'-biphenyl]-2-carboxamide |
| 85 | 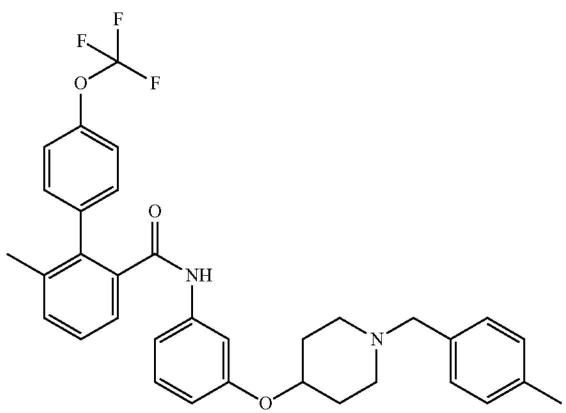 | | ES+ 575.4 | 6-methyl-N-[3-[[1-[(4-methylphenyl)-methyl]-4-piperidinyl]oxy]phenyl]-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 86 | 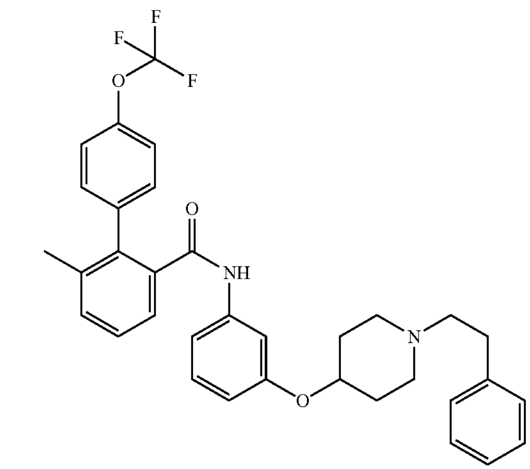 | | ES+ 575.3 | 6-methyl-N-[3-[[1-(2-phenylethyl)-4-piperidinyl]oxy]phenyl]-4'-(trifluoromethoxy)[1,1'-biphenyl]-2-carboxamide |
| 87 | 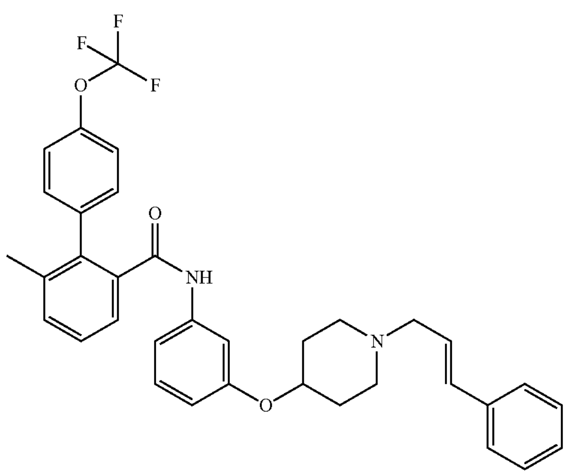 | | ES+ 587.3 | 6-methyl-N-[3-[[1-[(2E)-3-phenyl-2-propenyl]-4-piperidinyl]oxy]phenyl]-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 88 | 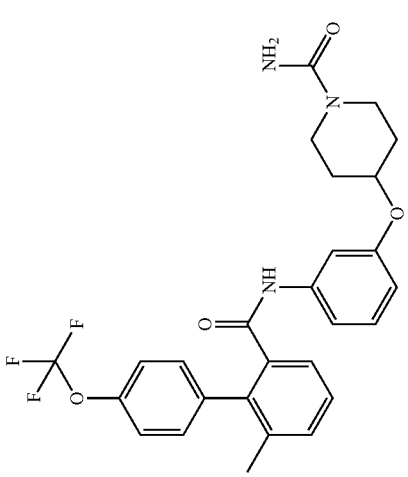 | $^1$H NMR(300 MHz; DMSO-D6); δ ppm: 1.4(m; 2H); 1.8(m; 2H); 2.1(s; 3H); 3.1(m; 2H); 36(m; 2H);4.4(m; 1H); 5.9(s; 2H); 6.6(m; J=8.0 Hz; 1H); 6.9(m; 1H); 7.1(m; 2H); 7.4(m; 7H); 10.0(s; 1H) | ES− 512.3 | 4-[3-[[[6-methyl-4′-(trifluoromethoxy)[1,1′-biphenyl]-2-yl]carbonyl]amino]phenoxy]-1-piperidinecarboxamide |
| 89 | 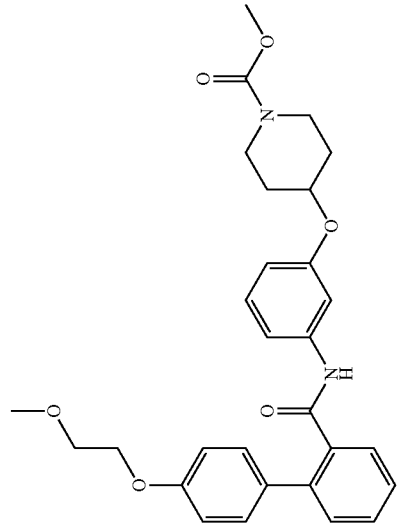 | $^1$H NMR(300 MHz; Chloroform-D) δ ppm: 1.8(m; 2H); 1.9(m; 2H); 3.4(s; 5H); 3.7(m; 7H); 4.1(m; 2H); 4.4(m; 1H); 6.5(m; J=9.2 Hz; 1H); 6.6(m; J=7.8 Hz; 1H); 7.1(m; 5H); 7.5(m; 5H); 7.8(m; J=1.3 Hz; 1H) | ES+ 505.3 | methyl 4-[3-[[[4′-(2-methoxyethoxy)[1,1′-biphenyl]-2-yl]carbonyl]amino]phenoxy]-1-piperidinecarboxylate |

TABLE 1-continued

| No. | STRUCTURES | NMR | MASS | NOMENCLATURE |
|---|---|---|---|---|
| 90 | 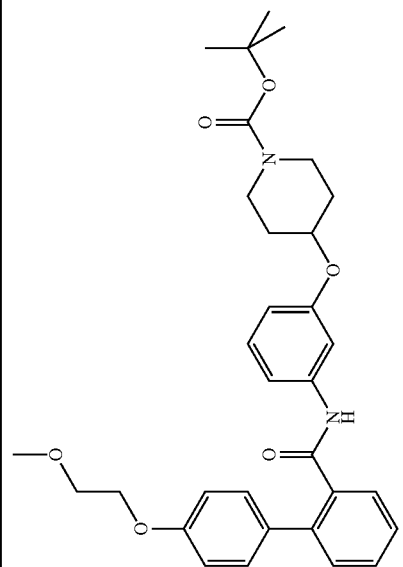 | ¹H NMR(300 MHz; Chloroform-D) δ ppm: 1.5(s; 9H); 1.7(m; 2H); 1.9(m; 2H) 3.4(m, J=3.6 Hz; 2H); 3.4(s; 3H) 3.7(m; 4H); 4.1(m; 2H); 4.4(m; 1H); 6.5(m; 1H); 6.6(m; 1H); 7.0(m; 5H); 7.5(m; 5H); 7.8(m; 1H) | ES+ 547.3 | 1,1-dimethylethyl 4-[3-[[[4'-(2-methoxyethoxy)[1,1'-biphenyl]-2-yl]carbonyl]-amino]phenoxy]-1-piperidinecarboxylate |
| 91 | 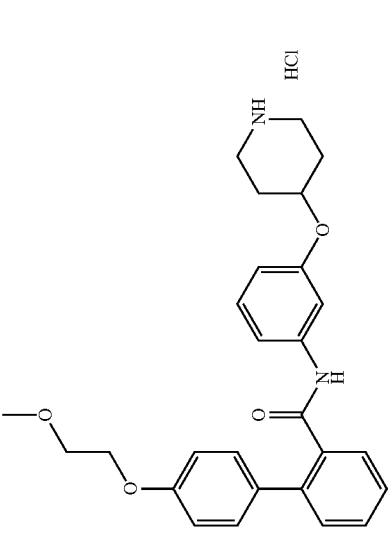 | ¹H NMR(300 MHz; Chloroform-D) δ ppm: 2.2(d; J=39.3 Hz; 4H); 3.3(m; 4H); 3.5(m; 3H); 3.8(m; 2H); 4.1(m; 2H); 4.6(s; 1H); 6.6(m; 2H); 7.0(m; 4H); 7.1(t; J=8.3 Hz; 1H); 7.4(m; 5H); 7.8(d; J=7.4 Hz; 1H); 9.5(s; 1H); 9.7(s; 1H) | Base ES+ 447.3 | 4'-(2-methoxyethoxy)-N-[3-(4-piperidinyloxy)phenyl]-[1,1'-biphenyl]-2-carboxamide monohydrochloride |

TABLE 1-continued

| No. | STRUCTURES | NMR | MASS | NOMENCLATURE |
|---|---|---|---|---|
| 92 | 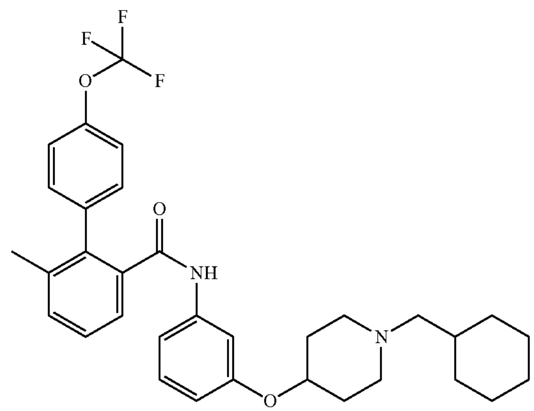 | | ES+ 567.3 | N-[3-[[1-(cyclohexylmethyl)-4-piperidinyl]oxy]phenyl]-6-methyl-4'-(trifluoromethoxy)[1,1'-biphenyl]-2-carboxamide |
| 93 | 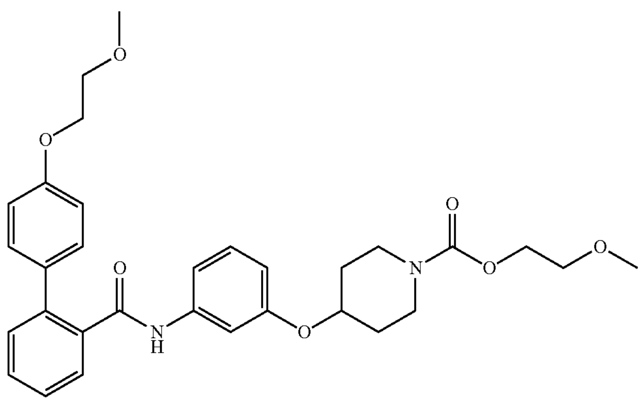 | ¹H NMR(300 MHz; Chloroform-D); δ ppm: 1.8(m; 2H); 1.9(m; 2H); 3.4(m; 8H); 3.7(m; 6H); 4.1(m; 2H); 4.2(m; 2H); 4.4(m; 1H); 6.5(d; J=7.2 Hz; 1H); 6.6(d; J=8.4 Hz; 1H); 7.0(m; 5H); 7.4(m; 5H); 7.8(d; J=7.4 Hz; 1H) | ES+ 549.3 | 2-methoxyethyl 4-[3-[[[4'-(2-methoxyethoxy)[1,1'-biphenyl]-2-yl]carbonyl]amino]phenoxy]-1-piperidinecarboxylate |

TABLE 1-continued
| No. | STRUCTURES | NMR | MASS | NOMENCLATURE |
|---|---|---|---|---|
| 94 | 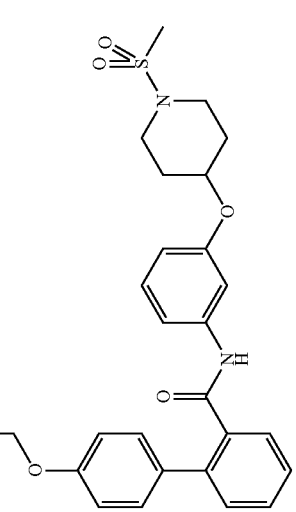 | ¹H NMR(300 MHz; Chloroform-D); δ ppm: 2.0(s; 4H); 2.8(s; 3H); 3.4(m; 4H); 3.4(s; 3H); 3.8(m; 2H); 4.1(m; 2H); 4.5(m; 1H); 6.4(m; 1H); 6.6(m; 1H); 7.0(m; J=8.6 Hz; 3H); 7.1(m; 1H); 7.2(m; 1H); 7.4(m; 5H); 7.9(d; J=8.0 Hz; 1H) | ES+ 525.3 | 4'-(2-methoxyethoxy)-N-[3-[[1-(methylsulfonyl)-4-piperidinyl]oxy]phenyl]-[1,1'-biphenyl]-2-carboxamide |
| 95 | 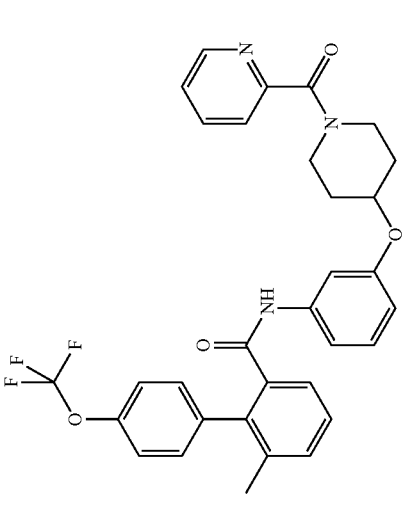 | | ES+ 576.2 | 6-methyl-N-[3-[[1-(2-pyridinylcarbonyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 96 | 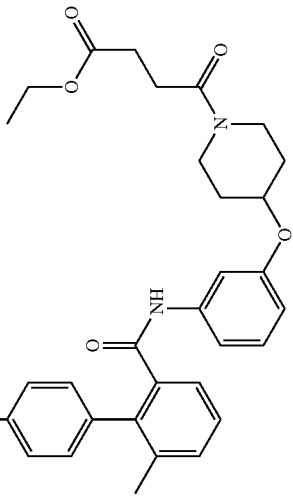 | | ES+ 599.3 | ethyl 4-[3-[[[6-methyl-4'-(trifluoromethoxy)-[1,1'-biphenyl]-2-yl]carbonyl]amino]-phenoxy]-γ-oxo-1-piperidinebutanoate |
| 97 | 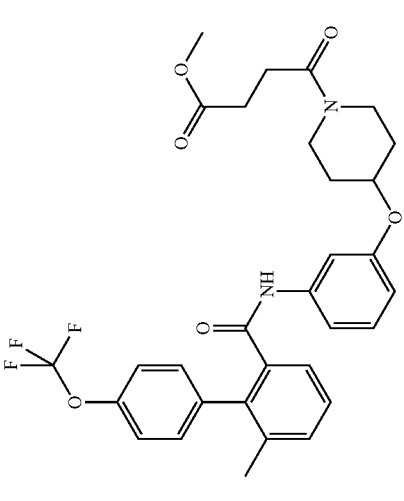 | | ES+ 585.3 | methyl 4-[3-[[[6-methyl-4'-(trifluoromethoxy)[1,1'-biphenyl]-2-yl]carbonyl]amino]-phenoxy]-γ-oxo-1-piperidinebutanoate |

TABLE 1-continued
| No. | STRUCTURES | NMR | MASS | NOMENCLATURE |
|---|---|---|---|---|
| 98 | 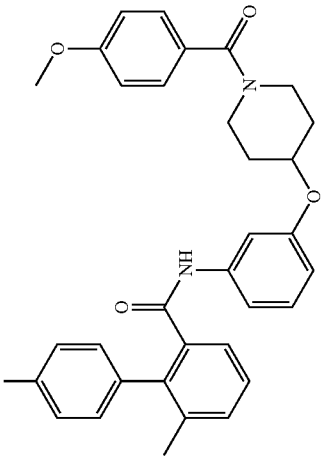 | | ES+ 605.3 | N-[3-[[1-(4-methoxybenzoyl)-4-piperidinyl]oxy]phenyl]-6-methyl-4'-(trifluoromethoxy)[1,1'-biphenyl]-2-carboxamide |
| 99 | 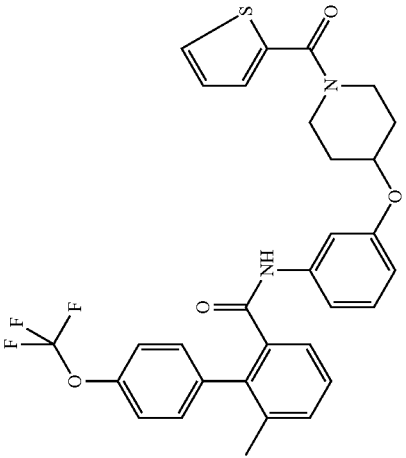 | | ES+ 581.3 | 6-methyl-N-[3-[[1-(2-thienylcarbonyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 100 | 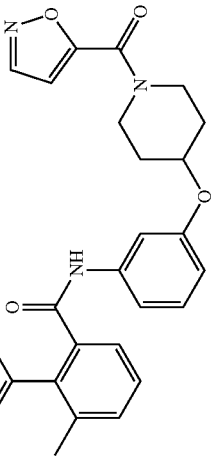 | | ES+ 566.3 | N-[3-[[1-(5-isoxazolylcarbonyl)-4-piperidinyl]oxy]phenyl]-6-methyl-4'-(trifluoromethoxy)[1,1'-biphenyl]-2-carboxamide |
| 101 | 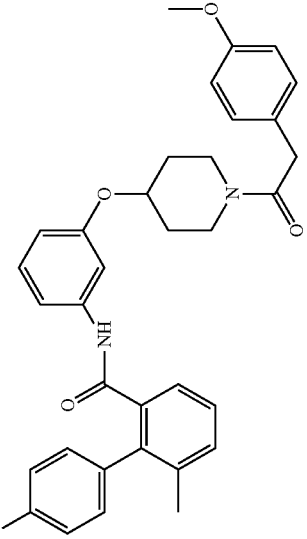 | | ES+ 619.3 | N-[3-[[1-[2-(4-methoxyphenyl)acetyl]-4-piperidinyl]oxy]phenyl]-6-methyl-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 102 | 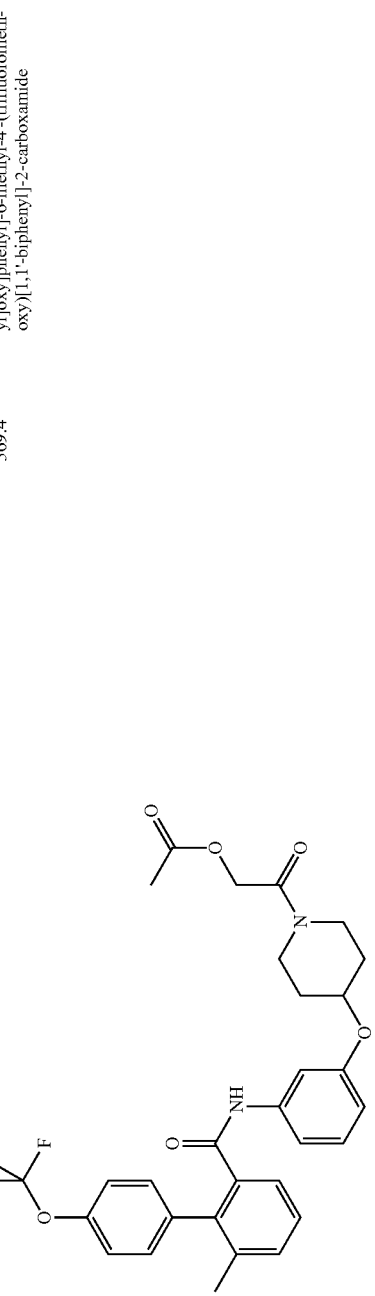 | | ES−569.4 | N-[3-[[1-[2-(acetyloxy)acetyl]-4-piperidinyl]oxy]phenyl]-6-methyl-4'-(trifluoromethoxy)[1,1'-biphenyl]-2-carboxamide |
| 103 | 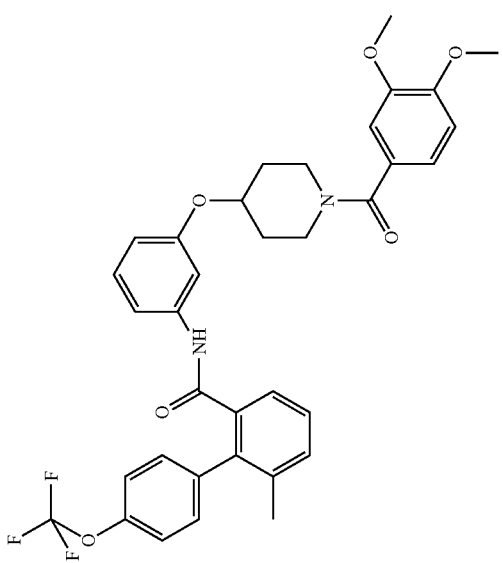 | | ES+ 635.3 | N-[3-[[1-(3,4-dimethoxybenzoyl)-4-piperidinyl]oxy]phenyl]-6-methyl-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 104 | 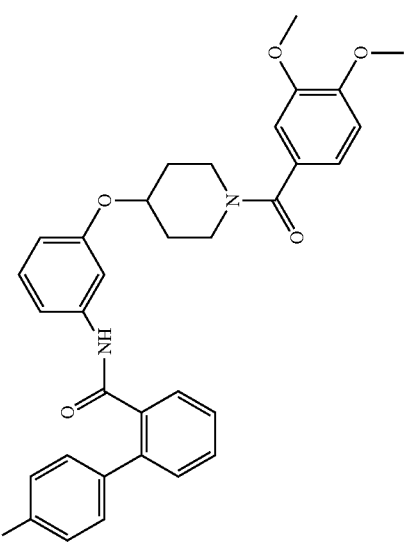 | | ES+ 621.3 | N-[3-[[1-(3,4-dimethoxybenzoyl)-4-piperidinyl]oxy]phenyl]-4'-(trifluoromethoxy)-[1,1'-biphenyl]-2-carboxamide |
| 105 | 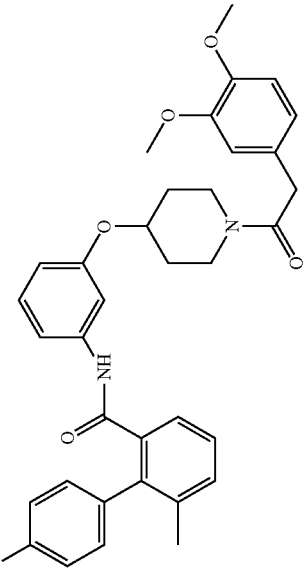 | | ES+ 649.3 | N-[3-[[1-[2-(3,4-dimethoxyphenyl)-acetyl]-4-piperidinyl]oxy]phenyl]-6-methyl-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 106 | 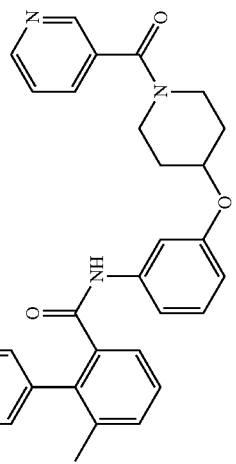 | | ES+ 576.7 | 6-methyl-N-[3-[[1-(3-pyridinylcarbonyl)-4-piperidinyl]oxy]phenyl]-4'-(trifluoromethoxy)[1,1'-biphenyl]-2-carboxamide |
| 107 | 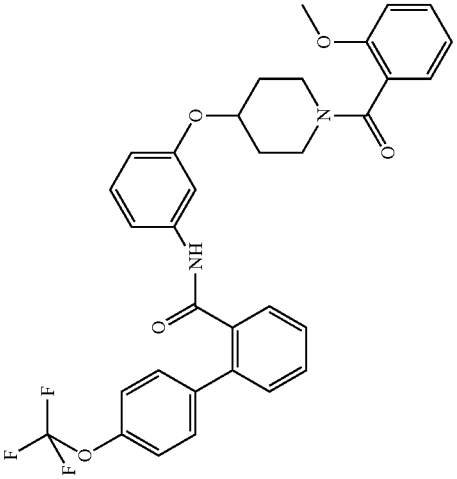 | | ES+ 591.3 | N-[3-[[1-(2-methoxybenzoyl)-4-piperidinyl]oxy]phenyl]-4'-(trifluoromethoxy)[1,1'-biphenyl]-2-carboxamide |

| No. | STRUCTURES | NMR | MASS | NOMENCLATURE |
|---|---|---|---|---|
| 108 | 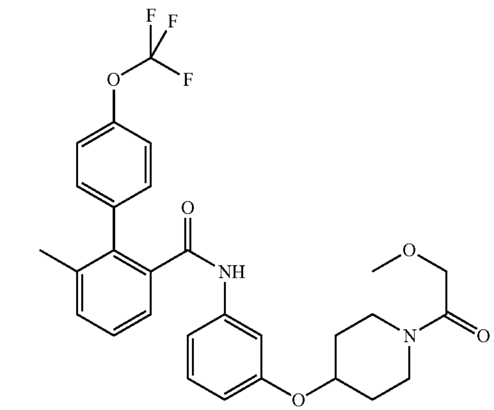 | | ES+ 543.3 | N-[3-[[1-(2-methoxyacetyl)-4-piperidinyl]-oxy]phenyl]-6-methyl-4'-(trifluorometh-oxy)[1,1'-biphenyl]-2-carboxamide |
| 109 | 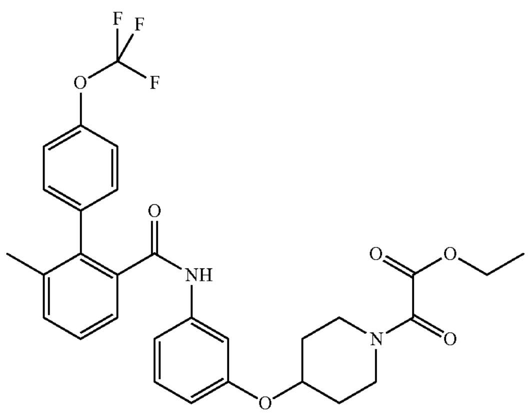 | | ES+ 571.3 | ethyl 4-[3-[[[6-methyl-4'-(trifluoromethoxy)-[1,1'-biphenyl]-2-yl]carbonyl]amino]-phenoxy]-α-oxo-1-piperidineacetate |

| No. | STRUCTURES | NMR | MASS | NOMENCLATURE |
|---|---|---|---|---|
| 110 | 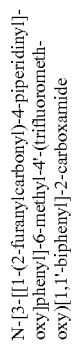 | | ES+ 635.3 | N-[3-[[1-[2-(3,4-dimethoxyphenyl)acetyl]-4-piperidinyl]oxy]phenyl]-4'-(trifluoromethoxy)[1,1'-biphenyl]-2-carboxamide |
| 111 | 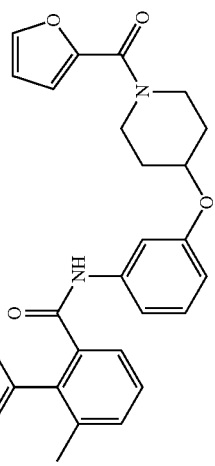 | | ES+ 565.3 | N-[3-[[1-(2-furanylcarbonyl)-4-piperidinyl]-oxy]phenyl]-6-methyl-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 112 | 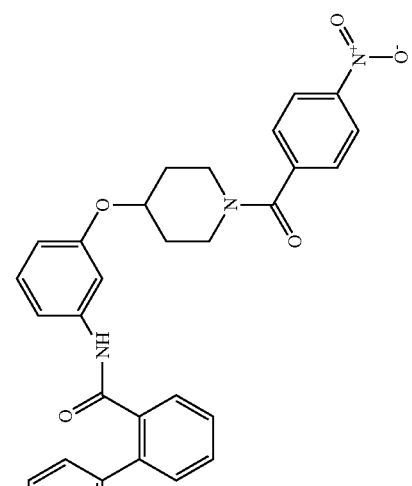 | | ES+ 606.3 | N-[3-[[1-(4-nitrobenzoyl)-4-piperidinyl]-oxy]phenyl]-4'-(trifluaromethoxy)[1,1'-biphenyl]-2-carboxamide |
| 113 | 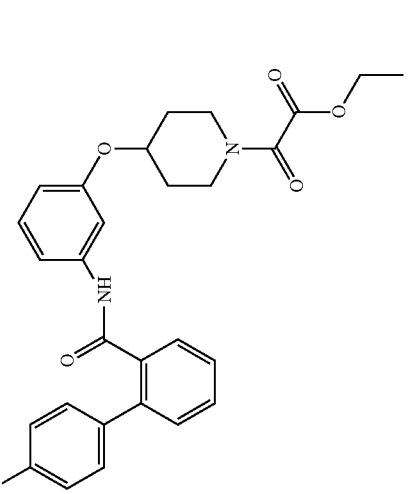 | | ES+ 557.3 | ethyl α-oxo-4-[3-[[[4'-(trifluoromethoxy)-[1,1'-biphenyl]-2-yl]carbonyl]amino]-phenoxy]-1-piperidineacetate |

TABLE 1-continued

| No. | STRUCTURES | NMR | MASS | NOMENCLATURE |
|---|---|---|---|---|
| 114 | 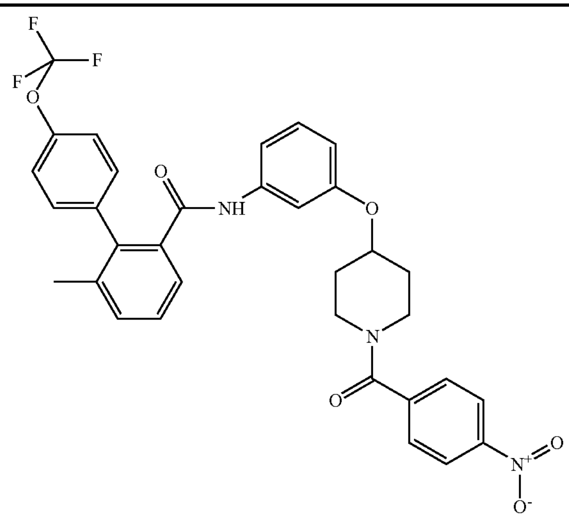 | | ES+ 620.3 | 6-methyl-N-[3-[[1-(4-nitrobenzoyl)-4-piperidinyl]oxy]phenyl]-4'-(trifluoromethoxy)[1,1'-biphenyl]-2-carboxamide |
| 115 | 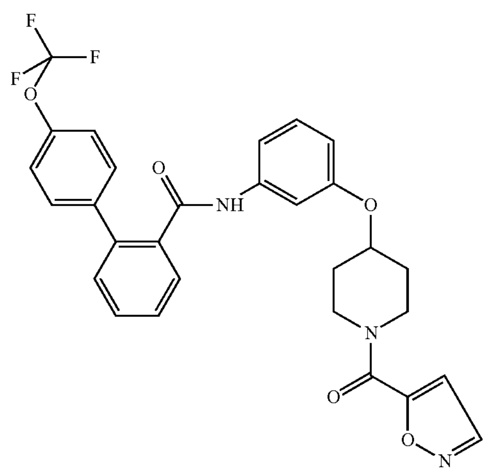 | | ES+ 552.3 | N-[3-[[1-(5-isoxazolylcarbonyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 116 | 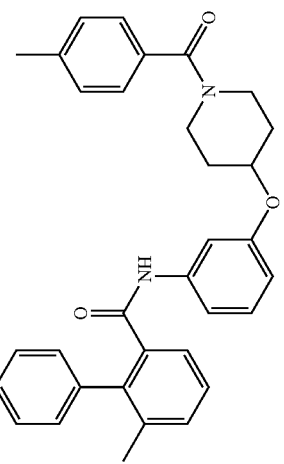 | | ES+ 589.3 | 6-methyl-N-[3-[[1-(4-methylbenzoyl)-4-piperidinyl]oxy]phenyl]-4'-(trifluoromethoxy)[1,1'-biphenyl]-2-carboxamide |
| 117 | 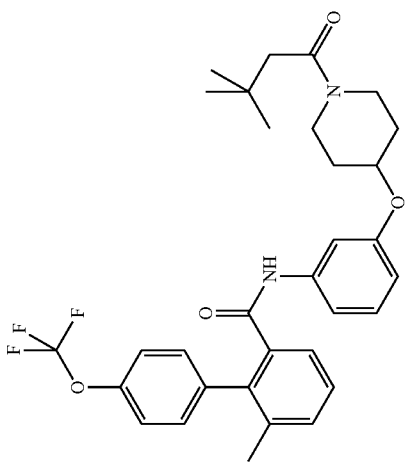 | | ES+ 569.4 | N-[3-[[1-(3,3-dimethyl-1-oxobutyl)-4-piperidinyl]oxy]phenyl]-6-methyl-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 118 | 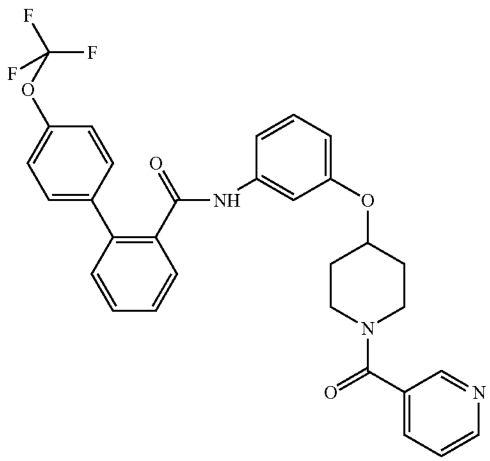 | | ES+ 562.3 | N-[3-[[1-(3-pyridinylcarbonyl)-4-piperidinyl]oxy]phenyl]-4'-(trifluoromethoxy)[1,1'-biphenyl]-2-carboxamide |
| 119 | 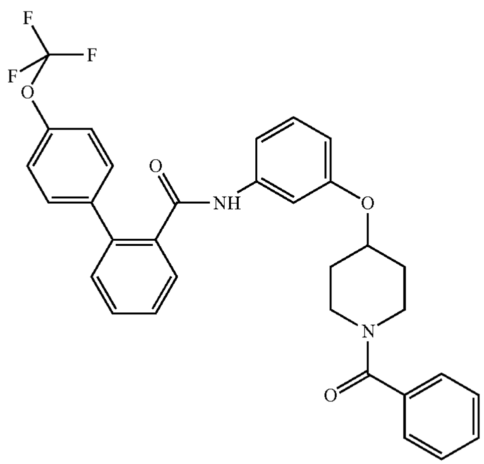 | | ES+ 561.3 | N-[3-[(1-benzoyl-4-piperidinyl)oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 120 | 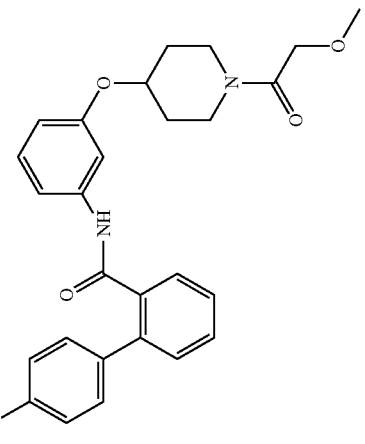 | | ES+ 529.3 | N-[3-[[1-(2-methoxyacetyl)-4-piperidinyl]-oxy]phenyl]-4'-(trifluoromethoxy)[1,1'-biphenyl]-2-carboxamide |
| 121 | 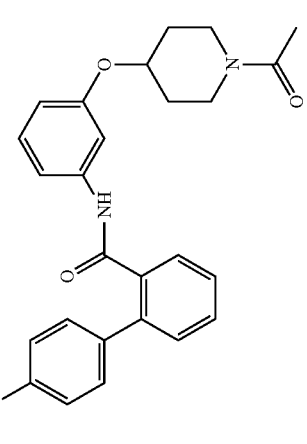 | | ES+ 499.2 | N-[3-[(1-acetyl-4-piperidinyl)oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 122 | 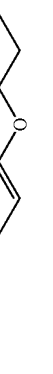 | | ES+ 605.3 | N-[3-[[1-(2-methoxybenzoyl)-4-piperidinyl]oxy]phenyl]-6-methyl-4'-(trifluoromethoxy)[1,1'-biphenyl]-2-carboxamide |
| 123 | 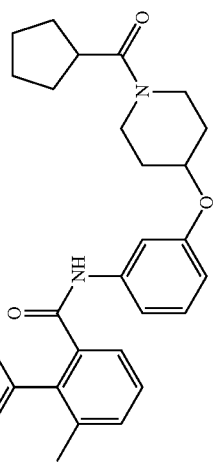 | | ES+ 567.3 | N-[3-[[1-(cyclopentylcarbonyl)-4-piperidinyl]oxy]phenyl]-6-methyl-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 124 | 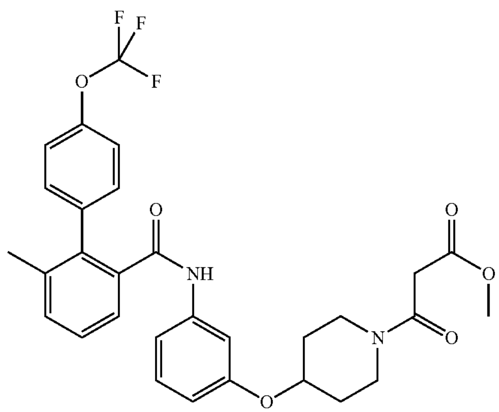 | | ES+ 571.3 | methyl 4-[3-[[[6-methyl-4'-(trifluoromethoxy)[1,1'-biphenyl]-2-yl]carbonyl]amino]-phenoxy]-β-oxo-1-piperidinepropanoate |
| 125 | 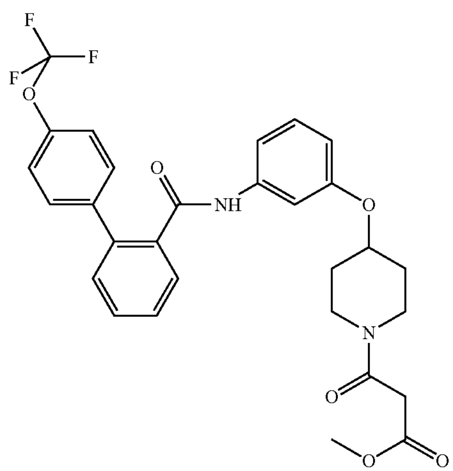 | | ES+ 557.3 | methyl β-oxo-4-[3-[[[4'-(trifluoromethoxy)[1,1'-biphenyl]-2-yl]carbonyl]amino]-phenoxy]-1-piperidinepropanoate |

TABLE 1-continued
| No. | STRUCTURES | NMR | MASS | NOMENCLATURE |
|---|---|---|---|---|
| 126 | 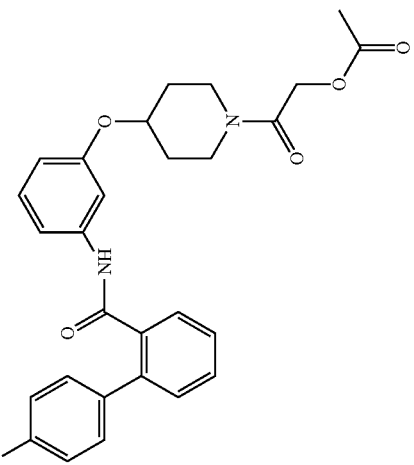 | | ES+ 557.3 | N-[3-[[1-[2-(acetyloxy)acetyl]-4-piperidinyl]oxy]phenyl]-4'-(trifluoromethoxy)[1,1'-biphenyl]-2-carboxamide |
| 127 | 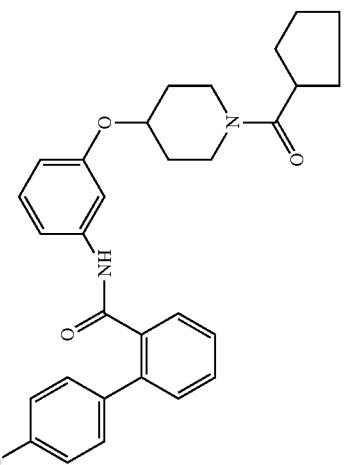 | | ES+ 553.3 | N-[3-[[1-(cyctopentylcarbonyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 128 | 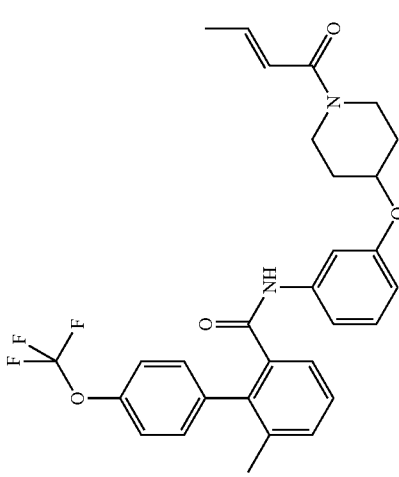 | | ES+ 539.3 | 6-methyl-N-[3-[[1-[(2E)-1-oxo-2-butenyl]-4-piperidinyl]oxy]phenyl]-4'-(trifluoromethoxy)[1,1'-biphenyl]-2-carboxamide |
| 129 | 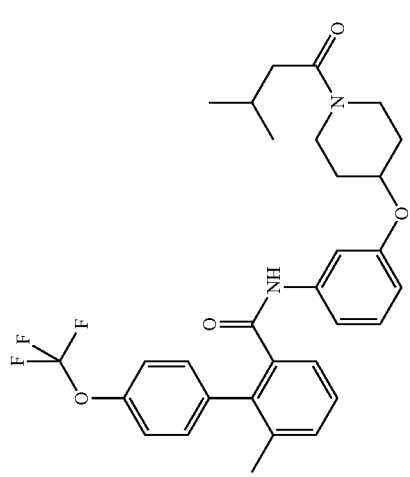 | | ES+ 555.3 | 6-methyl-N-[3-[[1-(3-methyl-1-oxobutyl)-4-piperidinyl]oxy]phenyl]-4'-(trifluoromethoxy)[1,1'-biphenyl]-2-carboxamide |

| No. | STRUCTURES | NMR | MASS | NOMENCLATURE |
|---|---|---|---|---|
| 130 | 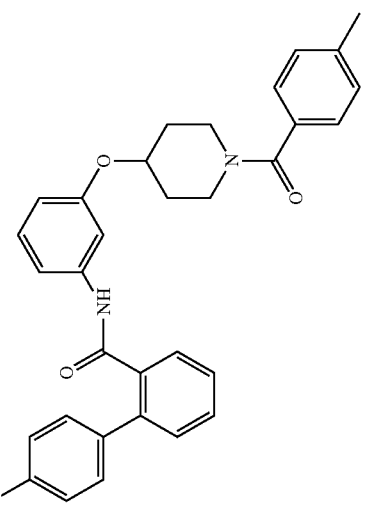 | | ES+ 575.3 | N-[3-[[1-(4-methylbenzoyl)-4-piperidinyl]-oxy]phenyl]-4'-(trifluoromethoxy)[1,1'-biphenyl]-2-carboxamide |
| 131 | 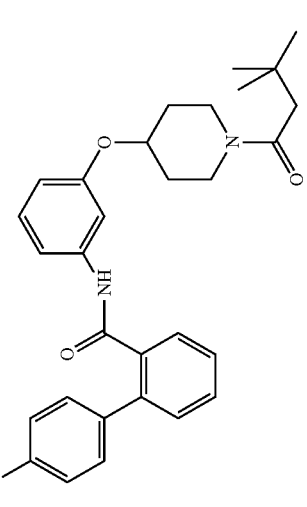 | | ES+ 555.3 | N-[3-[[1-(3,3-dimethyl-1-oxobutyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 132 | 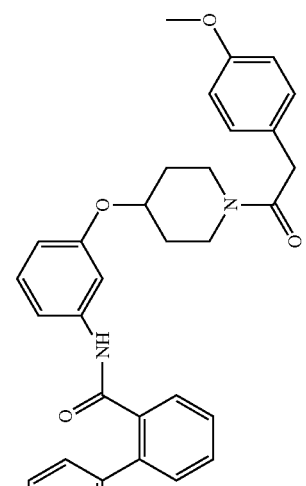 | | ES+ 605.3 | N-[3-[[1-[2-(4-methoxyphenyl)acetyl]-4-piperidinyl]oxy]phenyl]-4'-(trifluoromethoxy)[1,1'-biphenyl]-2-carboxamide |
| 133 | 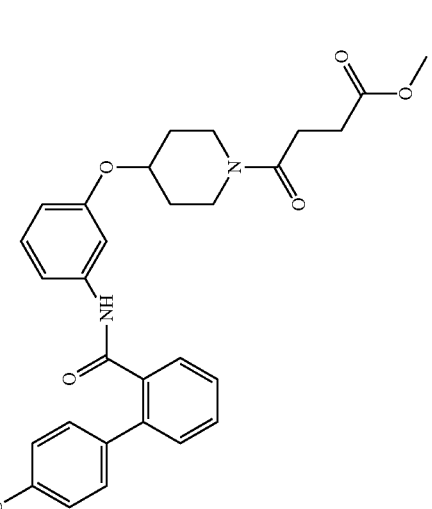 | | ES+ 571.3 | methyl γ-oxo-4-[3-[[[4'-(trifluoromethoxy)[1,1'-biphenyl]-2-yl]carbonyl]amino]phenoxy]-1-piperidinebutanoate |

TABLE 1-continued
| No. | STRUCTURES | NMR | MASS | NOMENCLATURE |
|---|---|---|---|---|
| 134 | 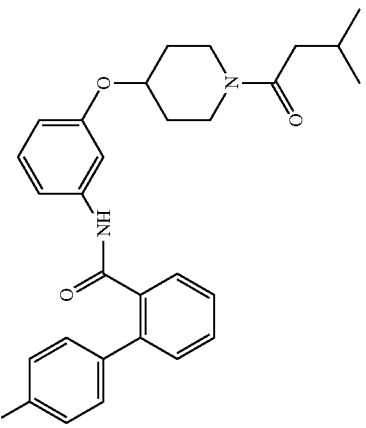 | | ES+ 541.3 | N-[3-[[1-(3-methyl-1-oxobutyl)-4-piperidinyl]oxy]phenyl]-4'-(trifluoromethoxy)-[1,1'-biphenyl]-2-carboxamide |
| 135 | 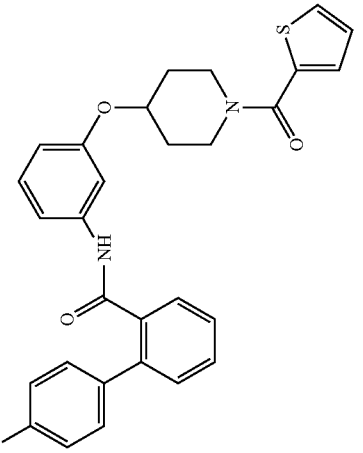 | | ES+ 567.2 | N[3-[[1-(2-thienylcarbonyl)-4-piperidinyl]oxy]phenyl]-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 136 | 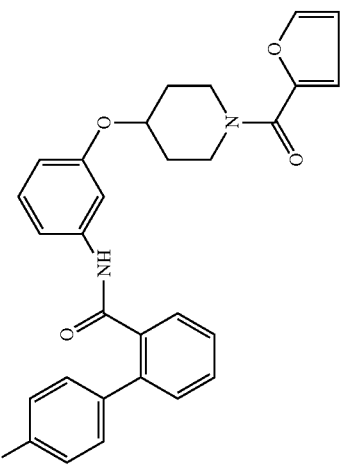 | | ES+ 551.3 | N-[3-[[1-(2-furanylcarbonyl)-4-piperidinyl]-oxy]phenyl]-4'-(trifluoromethoxy)[1,1'-biphenyl]-2-carboxamide |
| 137 | 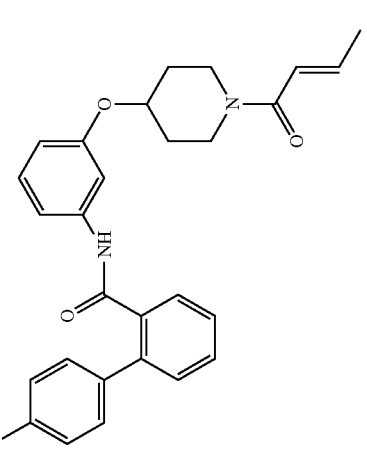 | | ES+ 525.3 | N-[3-[[1-[(2E)-1-oxo-2-butenyl]-4-piperidinyl]oxy]phenyl]-4'-(trifluoromethoxy)-[1,1'-biphenyl]-2-carboxamide |

TABLE 1-continued
| No. | STRUCTURES | NMR | MASS | NOMENCLATURE |
|---|---|---|---|---|
| 138 | 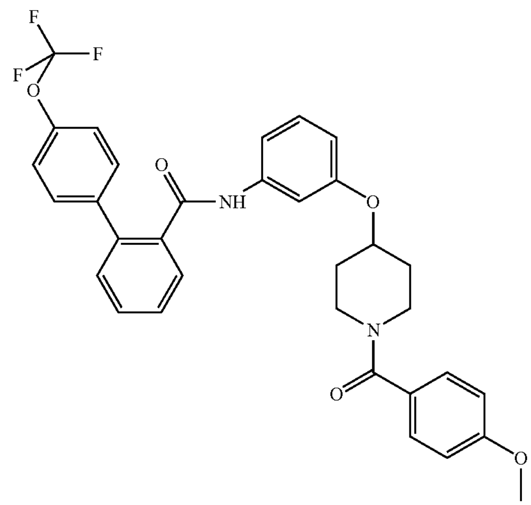 | | ES+ 591.3 | N-[3-[[1-(4-methoxybenzoyl)-4-piperidinyl]oxy]phenyl]-4'-(trifluoromethoxy)[1,1'-biphenyl]-2-carboxamide |
| 139 | 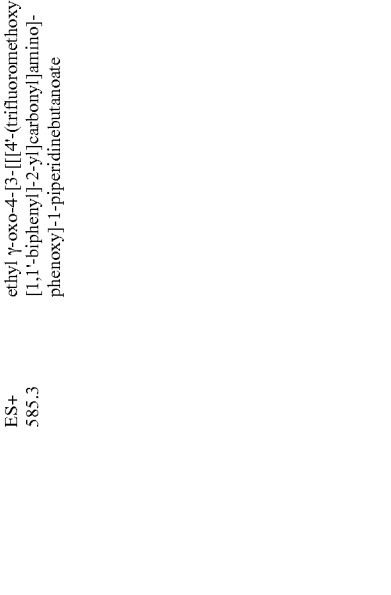 | | ES+ 585.3 | ethyl γ-oxo-4-[3-[[[4'-(trifluoromethoxy)-[1,1'-biphenyl]-2-yl]carbonyl][amino]-phenoxy]-1-piperidinebutanoate |

TABLE 1-continued
| No. | STRUCTURES | NMR | MASS | NOMENCLATURE |
|---|---|---|---|---|
| 140 | 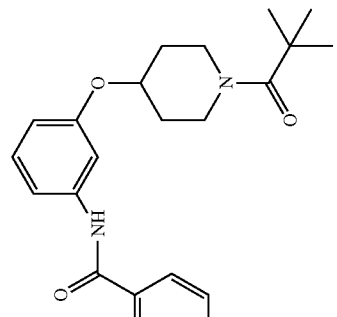 | | ES+ 541.3 | N-[3-[[1-(2,2-dimethyl-1-oxopropyl)-4-piperidinyl]oxy]phenyl]-4'-(trifluoromethoxy)[1,1'-biphenyl]-2-carboxamide |
| 141 | 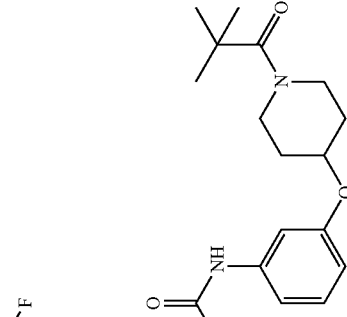 | | ES+ 555.3 | N-[3-[[1-(2,2-dimethyl-1-oxopropyl)-4-piperidinyl]oxy]phenyl]-6-methyl-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 142 | 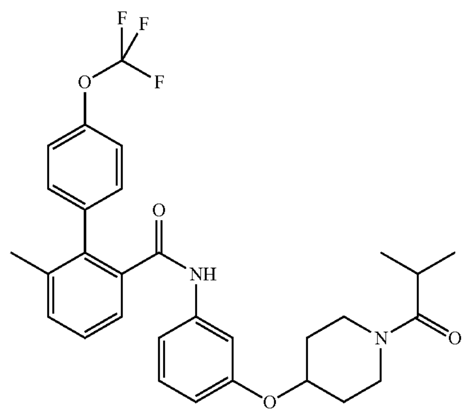 | | ES+ 541.3 | 6-methyl-N-[3-[[1-(2-methyl-1-oxopropyl)-4-piperidinyl]oxy]phenyl]-4'-(trifluoromethoxy)[1,1'-biphenyl]-2-carboxamide |
| 143 | 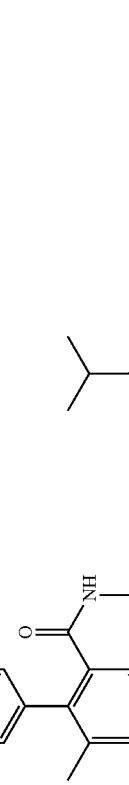 | | ES+ 575.3 | N-[3-[(1-benzoyl-4-piperidinyl)oxy]phenyl]-6-methyl-4'-(trifluoromethoxy)[1,1'-biphenyl]-2-carboxamide |

TABLE 1-continued
| No. | STRUCTURES | NMR | MASS | NOMENCLATURE |
|---|---|---|---|---|
| 144 | 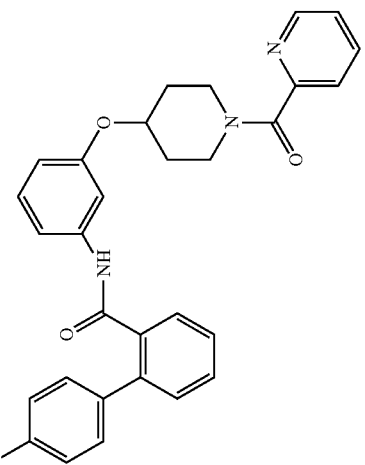 | | ES+ 562.3 | N-[3-[[1-(2-pyridinylcarbonyl)-4-piperidinyl]oxy]phenyl]-4'-(trifluoromethoxy)[1,1'-biphenyl]-2-carboxamide |
| 145 | 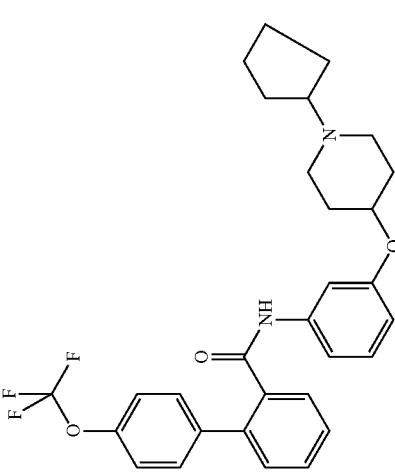 | | ES+ 525.3 | N-[3-[(1-cyclopentyl-4-piperidinyl)oxy]phenyl]-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 146 | 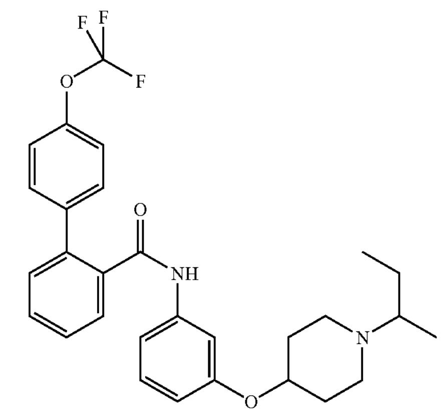 | | ES+ 513.3 | N-[3-[[1-(1-methylpropyl)-4-piperidinyl]-oxy]phenyl]-4'-(trifluoromethoxy)[1,1'-biphenyl]-2-carboxamide |
| 147 | 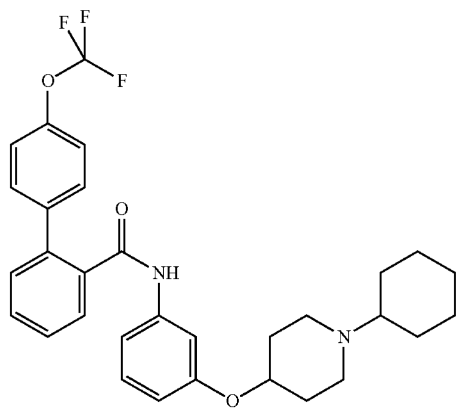 | | ES+ 539.3 | N-[3-[(1-cyclohexyl-4-piperidinyl)oxy]-phenyl]-4'-(trifluoromethoxy)[1,1'-biphenyl]-2-carboxamide |

TABLE 1-continued

| No. | STRUCTURES | NMR | MASS | NOMENCLATURE |
|---|---|---|---|---|
| 148 | 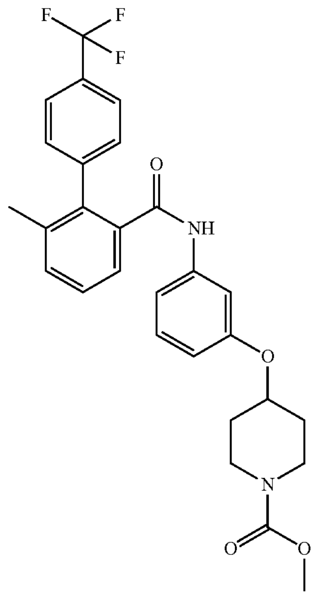 | | ES+ 513.5 | methyl 4-[[3-[[[6-methyl-4'-(trifluoromethyl)-[1,1'-biphenyl]-2-yl]carbonyl]amino]-phenoxy]-1-piperidinecarboxylate |
| 149 | 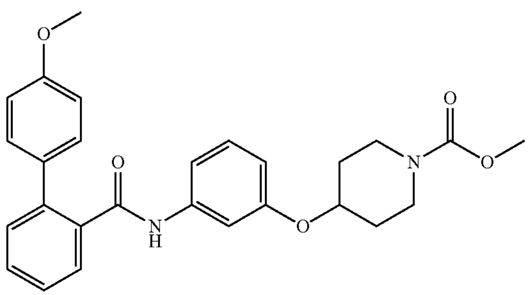 | | ES+ 461.3/ES– 459.4 | methyl 4-[3-[[(4'-methoxy[1,1'-biphenyl]-2-yl)carbonyl]amino]phenoxy]-1-piperidine-carboxylate |

TABLE 1-continued
| No. | STRUCTURES | NMR | MASS | NOMENCLATURE |
|---|---|---|---|---|
| 150 | 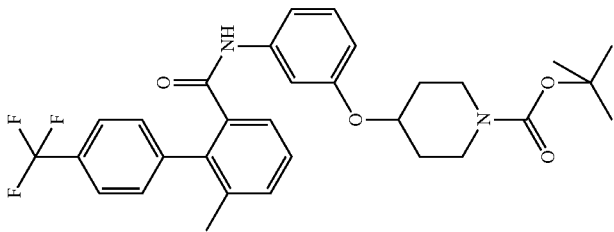 | ¹H NMR(300 MHz; Chloroform-D); δ ppm: 1.5(s; 9H); 1.7(m; 4H); 2.2(s; 3H); 3.3(m; 2H); 3.6(m; 2H); 4.4(m; 1H); 6.5(d; J=7.8 Hz; 1H); 6.6(dd; J=8.2; 1.7 Hz; 1H); 6.9(s; 1H); 7.0(s; 1H); 7.1(t; J=8.1 Hz; 1H); 7.4(m; 4H); 7.6(dd; J=6.4; 2.4 Hz; 1H); 7.7(d; J=8.0 Hz; 2H) | ES+ 455.4 499.3 555.4 577.4 ES− 553.5 599.5 | 1,1-dimethylethyl 4-[3-[[[6-methyl-4'-(trifluoromethyl)[1,1'-biphenyl]-2-yl]-carbonyl]amino]phenoxy]-1-piperidine-carboxylate |

TABLE 1-continued

| No. | STRUCTURES | NMR | MASS | NOMENCLATURE |
|---|---|---|---|---|
| 151 | 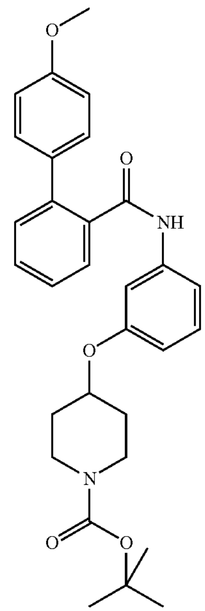 | ¹H NMR(300 MHz; Chloroform-D); δ ppm: 1.5(d; J=1.9 Hz; 9H); 1.8(m; 4H); 3.3(m; 2H); 3.7(m; 2H); 3.8(s; 3H); 4.4(m; 1H); 6.6(m; 2H); 7.0(m; 4H); 7.1(m; 1H); 7.5(m; 5H); 7.9(dd; J=7.5; 1.2 Hz; 1H | ES+ 403.3 447.3 503.3 525.3 ES− 501.4 547.4 | 1,1-dimethylethyl 4-[3-[[(4'-methoxy[1,1'-biphenyl]-2-yl)carbonyl]amino]phenoxy]-1-piperidinecarboxylate |

TABLE 1-continued
| No. | STRUCTURES | NMR | MASS | NOMENCLATURE |
|---|---|---|---|---|
| 152 | 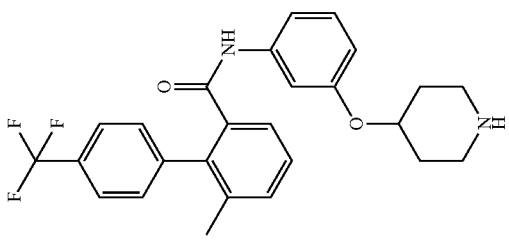 | ¹H NMR(300MHz; Chloroform-D); δ ppm: 1.6(m; 2H); 2.0(s; 2H); 2.2(s; 3H); 2.7(m; 3H); 3.1(d; J=4.6 Hz; 2H); 4.3(m; 1H); 6.5(d; J=7.6 Hz; 1H); 6.6(dd; J=8.2; 2.1 Hz; 1H); 6.9(s; 1H); 7.1(m; 2H); 7.4(m; 4H); 7.6(d; J=6.5 Hz; 1H); 7.7(d; J=7.8 Hz; 2H) | ES+ 455.3 ES− 453.4 499.4 | 6-methyl-N-[3-(4-piperidinyloxyphenyl]-4'-(trifluoromethyl)[1,1'-biphenyl]-2-carboxamide |

TABLE 1-continued
| No. | STRUCTURES | NMR | MASS | NOMENCLATURE |
|---|---|---|---|---|
| 153 | 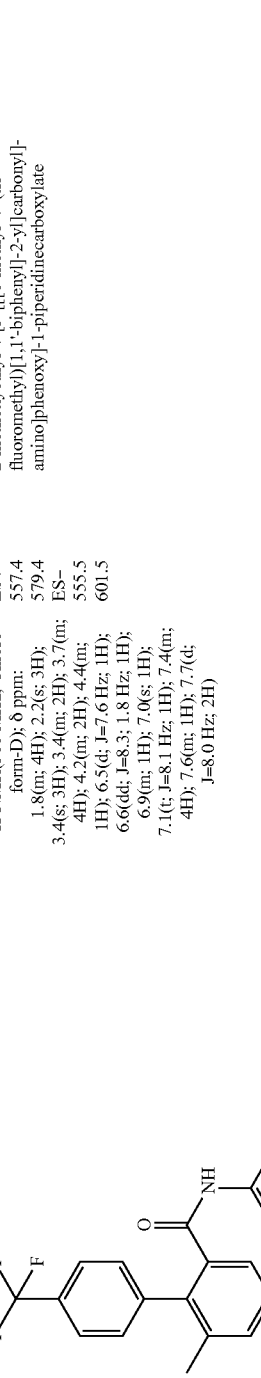 | ¹H NMR(300 MHz; Chloroform-D); δ ppm: 1.8(m; 4H); 2.2(s; 3H); 3.4(s; 3H); 3.4(m; 2H); 3.7(m; 4H); 4.2(m; 2H); 4.4(m; 1H); 6.5(d; J=7.6 Hz; 1H); 6.6(dd; J=8.3; 1.8 Hz; 1H); 6.9(m; 1H); 7.0(s; 1H); 7.1(t; J=8.1 Hz; 1H); 7.4(m; 4H); 7.6(m; 1H); 7.7(d; J=8.0 Hz; 2H) | ES+ 557.4 579.4 ES− 555.5 601.5 | 2-methoxyethyl 4-[3-[[[6-methyl-4′-(trifluoromethyl)[1,1′-biphenyl]-2-yl]carbonyl]-amino]phenoxy]-1-piperidinecarboxylate |

BIOLOGICAL EXPERIMENTAL SECTION

Biological Activity Tests

Analysis of the Inhibition of MTP Activity

The inhibition of the activity of microsomal triglyceride transfer protein (MTP) was tested by using the following operating protocol.

The inhibition of MTP activity with a compound can be quantified by observing the inhibition of the transfer of a labelled triglyceride, from a donor particle to an acceptor particle, in the presence of MTP. The procedure for the preparation of MTP is based on the method by Wetterau and Zilversmit (*Biochem. Biophys. Acta* (1986) 875, 610). A few grams of golden hamster liver are taken and then rinsed several times in a 250 mM sucrose solution at 0° C. All the following steps proceed at +4° C. A homogenate at a concentration of 50% in 250 mM sucrose is prepared using a Teflon mill and then centrifuged for 10 minutes at 10 000×g at +4° C. The supernatant is then centrifuged at 105 000×g for 75 minutes at +4° C. The supernatant is discarded and the microsomal pellet is taken up in 3 ml (per g of starting liver) of Tris/HCl 150 mM pH 8.0. 1-ml aliquot fractions are stored at −80° C. until the time of use.

After thawing a fraction of microsomes (1 ml), 12 ml of refrigerated Tris/HCl 50 mM, KCl 50 mM, $MgCl_2$ 5 mM pH 7.4 buffers and 1.2 ml of deoxycholate (0.54% in water) are added. After incubation for 30 minutes at +4° C. with gentle agitation, the suspension is centrifuged at 105 000×g for 75 minutes. The supernatant comprising the soluble MTP is dialysed against Tris/HCl 150 mM, NaCl 40 mM, EDTA 1 mM, 0.02% sodium azide pH 7.4 buffer (5 times one litre over 2-3 days). The MTP is stored at +4° C., is stable for at least 30 days and is used in unmodified form in the test.

The donor particles (liposomes) are prepared from 208 μl of L-phosphatidylcholine at a concentration of 10 mg/ml in chloroform, and 480 μl of [3H]-triolein at a concentration of 0.5 mCi/ml in toluene. After stirring, the solution is evaporated under nitrogen, taken up in 6 ml of Tris/HCl 50 mM, KCl 50 mM, $MgCl_2$ 5 mM pH 7.4 buffer and incubated in an ultrasound bath for 30 minutes at room temperature. The liposomes are stored at +4° C. and sonicated again for 10 minutes before each use.

The acceptor particles are biotinylated low density lipoproteins (LDL-biot). These particles are supplied by the company Amersham.

The reaction mixture is prepared in untreated ½ well white plates (Corning Costar) by addition, in the following order, of: 5 μl of HEPES 50 mM, NaCl 150 mM, BSA 0.1% (w/v), 0.05% sodium azide (w/v), pH 7.4 buffer; 5 μl of liposome; 5 μl of LDL-biot; 5 μl of test products in DMSO; 5 μl of MTP. After incubation for 18-24 hours at 37° C., the reaction is stopped by adding 100 μl of Amersham SPA (Scintillation Proximity Assay) beads coupled to streptavidin, and the radioactivity is counted using a Top Count (Packard) machine at least one hour later. The inhibition of the transfer of the triglycerides with a compound is reflected by a reduction in the transferred radioactivity. The percentage of inhibition for a given compound is determined relative to controls that do not comprise compounds in the reaction mixture.

The results are expressed in terms of the $IC_{50}$, i.e. the concentration that allows a 50% inhibition of MTP. These results are summarised in Table A below for a number of representative compounds of the invention.

TABLE A

| Example | $IC_{50}$ (nM) | Example | $IC_{50}$ (nM) | Example | $IC_{50}$ (nM) |
|---|---|---|---|---|---|
| 1 | 420.6 | 19 | 289.8 | 33 | 113.6 |
| 3 | 49.2 | 20 | 391.8 | 34 | 296.5 |
| 4 | 344.0 | 21 | 126.8 | 35 | 120.5 |
| 5 | 45.1 | 22 | 45.0 | 36 | 51.3 |
| 6 | 47.6 | 23 | 261.3 | 37 | 65.2 |
| 7 | 45.2 | 24 | 459.1 | 38 | 422.5 |
| 8 | 55.5 | 25 | 367.0 | 39 | 85.7 |
| 9 | 51.8 | 26 | 72.8 | 40 | 69.1 |
| 10 | 39.2 | 27 | 295.1 | 41 | 45.5 |
| 11 | 347.2 | 28 | 232.2 | 43 | 200.9 |
| 12 | 86.9 | 29 | 267.9 | 44 | 171.3 |
| 14 | 113.9 | 30 | 368.7 | 45 | 779.1 |
| 15 | 55.6 | 31 | 82.7 | 47 | 158.3 |
| 16 | 42.5 | 32 | 161.3 | 49 | 550.5 |
| 51 | 111.0 | 78 | 446.9 | 111 | 408.6 |
| 52 | 195.0 | 81 | 314.7 | 112 | 241.4 |
| 55 | 208.4 | 83 | 632.8 | 114 | 202.4 |
| 56 | 145.9 | 84 | 382.2 | 115 | 433.0 |
| 57 | 187.2 | 85 | 391.5 | 116 | 49.4 |
| 58 | 74.1 | 89 | 455.8 | 118 | 201.7 |
| 59 | 185.6 | 90 | 391.7 | 119 | 660.8 |
| 60 | 240.0 | 96 | 127.9 | 125 | 252.4 |
| 62 | 118.8 | 97 | 130.5 | 126 | 91.2 |
| 66 | 189.1 | 98 | 100.7 | 128 | 100.3 |
| 67 | 234.0 | 99 | 415.8 | 129 | 136.5 |
| 69 | 182.8 | 100 | 138.9 | 130 | 218.9 |
| 71 | 55.8 | 101 | 160.3 | 133 | 296.1 |
| 72 | 42.2 | 102 | 213.4 | 137 | 208.8 |
| 73 | 33.3 | 103 | 129.8 | 138 | 221.4 |
| 74 | 110.2 | 104 | 294.0 | 139 | 309.3 |
| 75 | 130.4 | 105 | 207.2 | 140 | 176.3 |
| 76 | 67.4 | 106 | 181.8 | 142 | 165.9 |
| 77 | 82.5 | 110 | 468.7 | 143 | 118.1 |

Analysis of the Secretion of apo B in the HepG2 Human Cell Line:

The activity of a compound according to the invention can be evaluated by measuring the inhibition of apo B secretion in HepG2 cells.

The HepG2 cells (ECACC—No. 85011430) are used as model in the study of the in vitro hepatic secretion of lipoproteins (Dixon J. and Ginsberg H., J., *Lipid. Res.*, 1993, 34, 167-179).

The HepG2 cells are cultured in Dulbecco's modified Eagle's medium comprising 10% foetal calf serum (DMEM and FBS—Gibco) in 96-well plates under an atmosphere of 5% carbon dioxide for 24 hours (about 70% confluence).

The test compounds are dissolved at a concentration of 2 or 10 mM in dimethyl sulfoxide (DMSO). Serial dilutions (1:3.16) are made in DMSO and are added (1:200—Robot Multimek Beckman) to the growth medium (200 μL) and then finally incubated for 24 hours in the various wells containing the HepG2 cells.

The 24-hour culture supernatant diluted to 1:5 (phosphate-buffered saline:PBS comprising 1% bovine serum albumin) is tested according to a sandwich-ELISA method specific for human apo B.

The results are expressed in terms of $IC_{50}$, i.e. the concentration that produces a 50% inhibition of apo B secretion in the HepG2 cells.

These results are collated in Table B below for a number of representative compounds of the invention.

TABLE B

| Example | $IC_{50}$ (nM) |
|---|---|
| 3 | 10.6 |
| 5 | 0.8 |
| 6 | 4.0 |

TABLE B-continued

| Example | IC$_{50}$ (nM) |
| --- | --- |
| 7 | 17.0 |
| 8 | 25.2 |
| 9 | 7.9 |
| 10 | 12.2 |
| 12 | 53.0 |
| 14 | 62.7 |
| 15 | 28.2 |
| 16 | 15.9 |
| 21 | 52.0 |
| 22 | 12.7 |
| 26 | 75.8 |
| 36 | 67.8 |
| 40 | 13.7 |
| 41 | 33.1 |
| 44 | 7.4 |
| 52 | 66.3 |
| 55 | 46.6 |
| 56 | 37.6 |
| 71 | 3.4 |
| 72 | 4.6 |
| 73 | 1.6 |
| 74 | 83.0 |
| 75 | 39.8 |
| 89 | 85.8 |
| 98 | 67.1 |
| 100 | 54.1 |
| 101 | 92.6 |
| 102 | 25.7 |
| 103 | 68.4 |
| 128 | 22.2 |
| 142 | 72.8 |

The invention claimed is:

1. An aroyl-O-piperidine compound of formula (I):

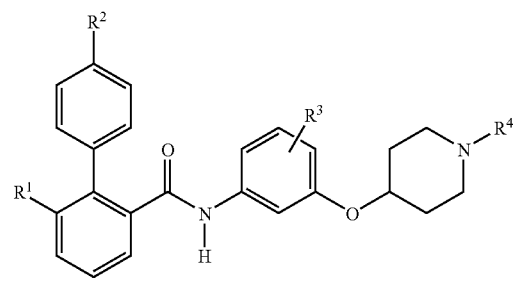

in which:
- $R^1$ is hydrogen, alkyl, or alkoxy;
- $R^2$ is alkyl, alkoxy, methoxyethoxy, trifluoromethyl, or trifluoromethoxy;
- $R^3$ is hydrogen or alkyl;
- $R^4$ is hydrogen, alkyl, alkenyl, alkynyl, aryl, arylalkyl, arylalkenyl, arylalkynyl, cycloalkyl, cycloalkylalkyl, heterocyclyl, heterocyclylalkyl, heteroaryl, heteroarylalkyl, —C(=Z)—$R^5$, in which Z is sulfur or oxygen, or is —S(O)$_2$—$R^6$, in which n is −1 or 2;
- $R^5$ is hydrogen, alkyl, alkenyl, alkynyl, cycloalkyl, cycloalkylalkyl, heterocyclyl, heterocyclylalkyl, aryl, aryl-alkyl, heteroaryl, heteroaryl, heteroarylalkyl, —O—$R^7$, —C(=O)—O—$R^7$, —S—$R^8$, or —NR$^9$R$^{10}$;
- $R^6$ is alkyl, alkenyl, alkynyl, cycloalkyl, heterocycloalkyl, aryl, heteroaryl, cycloalkylalkyl, heterocycloalkylalkyl, aryl-alkyl, or heteroarylalkyl;
- $R^7$ is hydrogen, alkyl, alkenyl, alkynyl, alkoxyalkyl, cycloalkyl, heterocycloalkyl, aryl, heteroaryl, cycloalkylalkyl, heterocycloalkylalkyl, arylalkyl, or heteroarylalkyl;
- $R^8$ is hydrogen, alkyl, alkenyl, or alkynyl;
- $R^9$ hydrogen or alkyl; and
- $R^{10}$ is hydrogen, alkyl which is optionally substituted by —C(=O)—O—$R^7$, alkenyl, alkynyl, —S(O)$_2$—$R^6$ in which n represents 1 or 2, cycloalkyl, heterocycloalkyl, aryl, heteroaryl, cycloalkylalkyl, heterocycloalkylalkyl, arylalkyl, or heteroarylalkyl;

wherein in each case the alkyl, alkenyl and alkynyl groups are optionally substituted by hydroxyl, linear or branched alkoxy having 1 to 6 carbon atoms, or —C(=O)—O—$R^7$, and in each case the cycloalkyl, heterocyclyl, aryl and heteroaryl groups are optionally substituted by halogen, alkyl, alkoxy, alkylthio, cyano, nitro, hydroxyl, trifluoromethyl, trifluoromethoxy, —C(=O)—O—$R^7$, or —NR$^9$R$^{10}$;

or a geometrical isomer, optical isomer, epimer, tautomeric form, oxidized form, or pharmaceutically acceptable salt thereof.

2. A compound according to claim 1, wherein $R^3$ is hydrogen.

3. A compound according to claim 1, wherein $R^1$ is hydrogen or methyl.

4. A compound according to claim 1, wherein $R^2$ is trifluoromethoxy, trifluoromethyl, methoxy or methoxyethoxy.

5. A compound according to claim 1, wherein $R^4$ is —S(O)$_2$—$R^6$, —C(=O)—O—$R^7$ or —C(=O)—NHR$^{10}$.

6. A compound according to claim 1, wherein
- $R^1$ hydrogen or methyl; and
- $R^2$ is trifluoromethoxy, trifluoromethyl, methoxy, or methoxyethoxy; and
- $R^3$ hydrogen; and
- $R^4$ is —S(O)$_2$—$R^6$, —C(=O)—O—$R^7$ or —C(=O)—NHR$^{10}$.

7. A compound according to claim 1, wherein said compound is:
- 6-methyl-N-[3-[[1-(methylsulfonyl)-4-piperidinyl]oxy]phenyl]-4'-(trifluoro-methoxy) [1,1'-biphenyl]-2-carboxamide;
- N-[3-[(1-acetyl-4-piperidinyl)oxy]phenyl]-6-methyl-4'-(trifluoromethoxy) [1,1'-biphenyl]-2-carboxamide;
- methyl 4-[3-[[[6-methyl-4'-(trifluoromethoxy) [1,1'-biphenyl]-2-yl]carbonyl]-amino]phenoxy]-1-piperidinecarboxylate;
- ethyl 4-[3-[[[6-methyl-4'-(trifluoromethoxy) [1,1'-biphenyl]-2-yl]carbonyl]-amino]phenoxy]-1-piperidinecarboxylate;
- phenylmethyl 4-[3-[[[6-methyl-4'-(trifluoromethoxy) [1,1'-biphenyl]-2-yl]-carbonyl]amino]phenoxy]-1-piperidinecarboxylate;
- 2-methylpropyl 4-[3-[[[6-methyl-4'-(trifluoromethoxy) [1,1'-biphenyl]-2-yl]-carbonyl]amino]phenoxy]-1-piperidinecarboxylate;
- 4-nitrophenyl 4-[3-[[[6-methyl-4'-(trifluoromethoxy) [1,1'-biphenyl]-2-yl]-carbonyl]amino]phenoxy]-1-piperidinecarboxylate;
- S-methyl 4-[3-[[[6-methyl-4'-(trifluoromethoxy) [1,1'-biphenyl]-2-yl]carbonyl]-amino]phenoxy]-1-piperidinecarbothioate;
- 4-[3-[[[6-methyl-4'-(trifluoromethoxy) [1,1'-biphenyl]-2-yl]carbonyl]amino]-phenoxy]-N-phenyl-1-piperidinecarboxamide;

N-ethyl-4-[3-[[[6-methyl-4'-(trifluoromethoxy) [1,1'-biphenyl]-2-yl]carbonyl]-amino]phenoxy]-1-piperidinecarboxamide;

6-methyl-N-[3-[[1-[(1-methylethyl)sulfonyl]-4-piperidinyl]oxy]phenyl]-4'-(trifluoromethoxy) [1,1'-biphenyl]-2-carboxamide;

6-methyl-N-[3-[[1-(phenylsulfonyl)-4-piperidinyl]oxy]phenyl]-4'-(trifluoro-methoxy) [1,1'-biphenyl]-2-carboxamide;

6-methyl-N-[3-[[1-[(phenylmethyl)sulfonyl]-4-piperidinyl]oxy]phenyl]-4'-(trifluoromethoxy) [1,1'-biphenyl]-2-carboxamide;

N-[3-[[1-[(5-chloro-1,3-dimethyl-1H-pyrazol-4-yl)sulfonyl]-4-piperidinyl]oxy]-phenyl]-6-methyl-4'-(trifluoromethoxy) [1,1'-biphenyl]-2-carboxamide;

N-[3-[[1-(butylsulfonyl)-4-piperidinyl]oxy]phenyl]-6-methyl-4'-(trifluoromethoxy) [1,1'-biphenyl]-2-carboxamide;

N-(4-methoxyphenyl)-4-[3-[[[6-methyl-4'-(trifluoromethoxy) [1,1'-biphenyl]-2-yl]carbonyl]amino]phenoxy]-1-piperidinecarboxamide;

ethyl N-[[4-[3-[[[6-methyl-4-(trifluoromethoxy) [1,1'-biphenyl]-2-yl]carbonyl]-amino]phenoxy]-1-piperidinyl]carbonyl]glycinate;

4-[3-[[[6-methyl-4'-(trifluoromethoxy) [1,1'-biphenyl]-2-yl]carbonyl]amino]-phenoxy]-N-2-propenyl-1-piperidinecarboxamide;

N-butyl-4-[3-[[[6-methyl-4'-(trifluoromethoxy) [1,1'-biphenyl]-2-yl]carbonyl]-amino]phenoxy]-1-piperidinecarboxamide;

4-[3-[[[6-methyl-4'-(trifluoromethoxy) [1,1'-biphenyl]-2-yl]carbonyl]amino]-phenoxy]-N-(phenylmethyl)-1-piperidinecarboxamide;

methyl 2-[[[4-[3-[[[6-methyl-4'-(trifluoromethoxy) [1,1'-biphenyl]-2-yl]carbonyl]-amino]phenoxy]-1-piperidinyl]carbonyl]amino]benzoate;

N-(3-cyanophenyl)-4-[3-[[[6-methyl-4'-(trifluoromethoxy) [1,1'-biphenyl]-2-yl]-carbonyl]amino]phenoxy]-1-piperidinecarboxamide;

N-[4-(methylthio)phenyl]-4-[3-[[[6-methyl-4'-(trifluoromethoxy) [1,1'-biphenyl]-2-yl]carbonyl]amino]phenoxy]-1-piperidinecarboxamide;

4-[3-[[[6-methyl-4-(trifluoromethoxy) [1,1'-biphenyl]-2-yl]carbonyl]amino]-phenoxy]-N-(2-phenylethyl)-1-piperidinecarboxamide;

N-hexyl-4-[3-[[[6-methyl-4-(trifluoromethoxy) [1,1'-biphenyl]-2-yl]carbonyl]-amino]phenoxy]-1-piperidinecarboxamide;

butyl N-[[4-[3-[[[6-methyl-4-(trifluoromethoxy) [1,1'-biphenyl]-2-yl]carbonyl]-amino]phenoxy]-1-piperidinyl]carbonyl]glycinate;

4-[3-[[[6-methyl-4-(trifluoromethoxy) [1,1'-biphenyl]-2-yl]carbonyl]amino]-phenoxy]-N-[2-(trifluoromethoxy)phenyl]-1-piperidinecarboxamide;

N-[4-(dimethylamino)phenyl]-4-[3-[[[6-methyl-4'-(trifluoromethoxy) [1,1'-biphenyl]-2-yl]carbonyl]amino]phenoxy]-1-piperidinecarboxamide;

N-[(4-methoxyphenyl)methyl]-4-[3-[[[6-methyl-4'-(trifluoromethoxy) [1,1'-biphenyl]-2-yl]carbonyl]amino]phenoxy]-1-piperidinecarboxamide;

methyl 4-[[[4-[3-[[[6-methyl-4-(trifluoromethoxy) [1,1'-biphenyl]-2-yl]carbonyl]-amino]phenoxy]-1-piperidinyl]carbonyl]amino]benzoate;

N-1,3-benzodioxol-5-yl-4-[3-[[[6-methyl-4'-(trifluoromethoxy) [1,1'-biphenyl]-2-yl]carbonyl]amino]phenoxy]-1-piperidinecarboxamide;

[1,1-biphenyl]-6-methyl-N-[3-[[1-(phenylmethyl)-4-piperidinyl]oxy]phenyl]-4'-(trifluoromethoxy)-2-carboxamide;

[1,1-biphenyl]-6-methyl-N-[3-[[1-(2-thienylmethyl)-4-piperidinyl]oxy]phenyl]-4'-(trifluoromethoxy)-2-carboxamide;

N-[3-[[1-(2-benzofuranylmethyl)-4-piperidinyl]oxy]phenyl]-6-methyl-4'-(trifluoromethoxy) [1,1'-biphenyl]-2-carboxamide;

methyl 4-[3-[[[4-(trifluoromethoxy) [1,1'-biphenyl]-2-yl]carbonyl]amino]-phenoxy]-1-piperidinecarboxylate;

methyl 4-[3-[[[4-(trifluoromethyl) [1,1'-biphenyl]-2-yl]carbonyl]amino]-phenoxy]-1-piperidinecarboxylate;

2-methoxyethyl 4-[3-[[[6-methyl-4'-(trifluoromethoxy) [1,1'-biphenyl]-2-yl]-carbonyl]amino]phenoxy]-1-piperidinecarboxylate;

2-methoxyethyl 4-[3-[[[4'-(trifluoromethoxy) [1,1-biphenyl]-2-yl]carbonyl]-amino]phenoxy]-1-piperidinecarboxylate;

2-methoxyethyl 4-[3-[[[4-(trifluoromethyl) [1,1'-biphenyl]-2-yl]carbonyl]amino]-phenoxy]-1-piperidinecarboxylate;

ethyl 4-[3-[[[4-(trifluoromethoxy) [1,1'-biphenyl]-2-yl]carbonyl]amino]-phenoxy]-1-piperidinecarboxylate;

N-[3-[[1-(4-methoxybenzoyl)-4-piperidinyl]oxy]phenyl]-6-methyl-4'-(trifluoro-methoxy) [1,1'-biphenyl]-2-carboxamide;

N-[3-[[1-(5-isoxazolylcarbonyl)-4-piperidinyl]oxy]phenyl]-6-methyl-4'-(trifluoro-methoxy) [1,1'-biphenyl]-2-carboxamide;

N-[3-[[1-[2-(4-methoxyphenyl)acetyl]-4-piperidinyl]oxy]phenyl]-6-methyl-4'-(trifluoromethoxy) [1,1'-biphenyl]-2-carboxamide;

N-[3-[[1-[2-(acetyloxy)acetyl]-4-piperidinyl]oxy]phenyl]-6-methyl-4'-(trifluoro-methoxy) [1,1'-biphenyl]-2-carboxamide;

N-[3-[[1-(3,4-dimethoxybenzoyl)-4-piperidinyl]oxy]phenyl]-6-methyl-4'-(trifluoromethoxy) [1,1'-biphenyl]-2-carboxamide;

N-[3-[[1-(4-nitrobenzoyl)-4-piperidinyl]oxy]phenyl]-4'-(trifluoromethoxy) [1,1'-biphenyl]-2-carboxamide;

N-[3-[[1-(5-isoxazolylcarbonyl)-4-piperidinyl]oxy]phenyl]-4'-(trifluoromethoxy) [1,1'-biphenyl]-2-carboxamide;

6-methyl-N-[3-[[1-[(2E)-1-oxo-2-butenyl]-4-piperidinyl]oxy]phenyl}-4'-(trifluoromethoxy)[1,1-biphenyl]-2-carboxamide;

6-methyl-N-[3-[[1-(2-methyl-1-oxopropyl)-4-piperidinyl]oxy]phenyl]-4'-(trifluoromethoxy) [1,1'-biphenyl]-2-carboxamide;

methyl 4-[3-[[[6-methyl-4-(trifluoromethyl) [1,1'-biphenyl]-2-yl]carbonyl]amino]phenoxy]-1-piperidinecarboxylate;

methyl 4-[3-[[(4-methoxy[1,1-biphenyl]-2-yl)carbonyl]amino]phenoxy]-1-piperidinecarboxylate;

1,1-dimethylethyl 4-[3-[[[6-methyl-4-(trifluoromethyl) [1,1'-biphenyl]-2-yl]-carbonyl]amino]phenoxy]-1-piperidinecarboxylate;

1,1-dimethylethyl 4-[3-[[(4-methoxy[1,1-biphenyl]-2-yl)carbonyl]amino]-phenoxy]-1-piperidinecarboxylate;

6-methyl-N-[3-(4-piperidinyloxy)phenyl]-4'-(trifluoromethyl) [1,1'-biphenyl]-2-carboxamide; or 2-methoxyethyl 4-[3-[[[6-methyl-4-(trifluoromethyl) [1,1'-biphenyl]-2-yl]-carbonyl]amino]phenoxy]-1-piperidinecarboxylate; or or a geometrical isomer, optical isomer, epimer, tautomeric form, oxidized form, or pharmaceutically acceptable salt thereof.

8. A process for the preparation of a compound according to claim 1, said process comprising:

reacting an acid of formula (II) together with an amine of formula (III) by an amide synthesis reaction

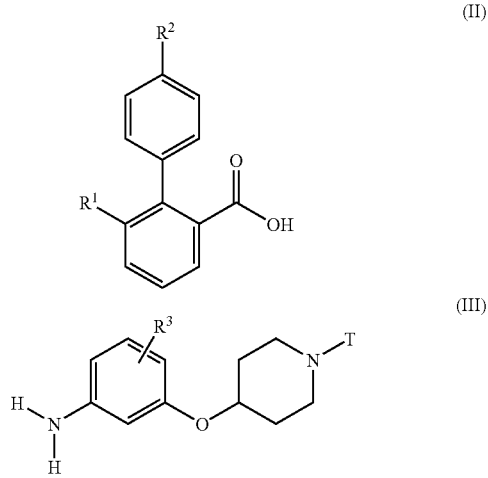

wherein T is a labile protecting group, to obtain a compound of formula (IV)

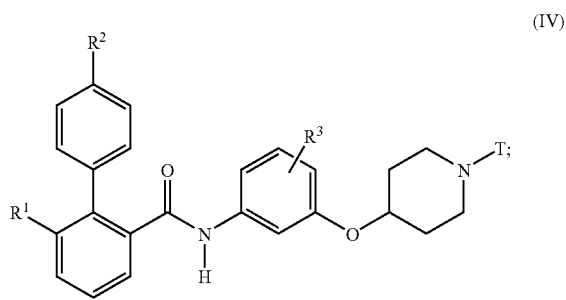

removing the labile protecting function T to obtain a compound of formula ($I_A$):

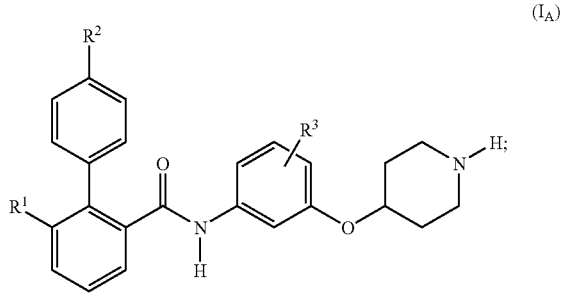

optionally converting the amine of formula ($I_A$) into an amine compound of formula (I) in which $R^4$ not hydrogen;

optionally purifying the resultant compound;

optionally separating the geometrical and/or optical isomers;

optionally converting the resultant compound into an oxidized form, and/or into a solvated or hydrated form; and optionally salifying the compound with an acid or a base, to obtain the corresponding pharmaceutically acceptable salt.

9. A pharmaceutical composition comprising a pharmaceutically effective amount of a compound according to claim 1, in combination with one or more pharmaceutically acceptable vehicles.

10. A method for treating a patient suffering from diabetes-related hypertriglyceridaemia, hypercholesterolemia, dyslipidaemia, or obesity, comprising administering to said patient an effective amount of a compound according to claim 1.

11. A method according to claim 10, wherein said patient is suffering from diabetes-related hypertriglyceridaemia.

12. A method according to claim 10, wherein said patient is suffering from hypercholesterolemia.

13. A method according to claim 10, wherein said patient is suffering from dyslipidaemia.

14. A method according to claim 10, wherein said patient is suffering from obesity.

15. A compound according to claim 4, wherein $R^2$ is trifluoromethoxy or trifluoromethyl.

16. A compound according to claim 6, wherein $R^2$ is trifluoromethoxy or trifluoromethyl.

17. A compound according to claim 1, wherein alkyl is in each case methyl, ethyl, propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, or 1-methyl-1-ethylpropyl;

alkenyl is in each case pent-1-en-1-yl, pent-2-en-1-yl and pent-3-en-1-yl radicals, but also the pent-1-en-2-yl, pent-2-en-2-yl and pent-3-en-2-yl radicals, and equally the pent-1-en-3-yl, pent-2-en-3-yl, or pent-3-en-3-yl;

alkynyl is in each case pent-1-yn-1-yl, pent-2-yn-1-yl and pent-3-yn-1-yl radicals, but also the pent-1-yn-2-yl, pent-2-yn-2-yl, pent-3-yn-2-yl, pent-1-yn-3-yl, pent-2-yn-3-yl, or pent-3-yn-3-yl;

alkoxy in each case is —O-alkyl wherein alkyl is as defined above;

cycloalkyl is cyclopropyl, cyclobutyl, cyclopentyl, cyclohexyl, cycloheptyl, cyclooctyl, cyclodecyl, adamantyl, diamantyl, nor-bornyl, or bornyl;

heterocyclyl is in each case morpholino, morpholinyl, piperidinyl, thiazolidinyl, oxazolidinyl, tetrahydrothienyl, tetrahydrofuryl, tetrahydropyranyl, pyrrolidinyl, isoxazolidinyl, imidazolidinyl, pyrazolidinyl, quinuclidinyl, indolinyl, isoindolinyl, chromanyl, isochromanyl, benzodioxolanyl, pyridine, furan, thiophene, pyrrole, imidazole, thiazole, isothiazole, isoxazole, furazane, pyridazine, pyrimidine, pyrazine, thiazines, oxazole, pyrazole, oxadiazole, triazole, thiadiazole, indolizine, indole, isoindole, benzofuran, benzothiophene, indazole, benzimidazole, benzothiazole, benzoxadiazole, benzofurazane, benzothiofurazane, purine, quinoline, isoquinoline, cinnoline, phthalazine, quinazoline, quinoxaline, naphthyridines, pyrazolotriazines, pyrazolopyrimidine, or pteridine;

heteroaryl is in each case pyridine, furan, thiophene, pyrrole, imidazole, thiazole, isothiazole, isoxazole, furazane, pyridazine, pyrimidine, pyrazine, thiazines, oxazole, pyrazole, oxadiazole, triazole, thiadiazole, indolizine, indole, isoindole, benzofuran, benzothiophene, indazole, benzimidazole, benzothiazole, benzoxadiazole, benzofurazane, benzothiofurazane, purine, quinoline, isoquinoline, cinnoline, phthalazine, quinazoline, quinoxaline, naphthyridines, pyrazolotriazines, pyrazolopyrimidine, or pteridine;

cycloalkylalkyl, heterocyclylalkyl, arylalkyl and heteroarylalkyl groups in each case are cycloalkyl, heterocyclyl, aryl and heteroaryl groups as defined above, which replace a hydrogen of an alkyl group as defined above; and arylalkenyl in each case is an aryl group as defined above, which replaces a hydrogen of an alkenyl group as defined above; and arylalkynyl in each case is an aryl group as defined above, which replaces a hydrogen of an alkynyl group as defined above.

18. A pharmaceutical composition comprising a pharmaceutically effective amount of a compound according to claim 7, in combination with one or more pharmaceutically acceptable vehicles.

19. A method for treating a patient suffering from diabetes-related hypertriglyceridaemia, hypercholesterolemia, dyslipidaemia, or obesity, comprising administering to said patient an effective amount of a compound according to claim 7.

20. A method according to claim 19, wherein said patient is suffering from diabetes-related hypertriglyceridaemia.

21. A method according to claim 19, wherein said patient is suffering from hypercholesterolemia.

22. A method according to claim 19, wherein said patient is suffering from dyslipidaemia.

23. A method according to claim 19, wherein said patient is suffering from obesity.

24. A compound according to claim 6, wherein $R^1$ is methyl and $R^2$ is trifluoromethoxy.

25. A compound according to claim 6, wherein $R^1$ is hydrogen and $R^2$ trifluoromethoxy.

26. A compound according to claim 6, wherein $R^1$ is hydrogen and $R^2$ trifluoromethyl.

27. A compound according to claim 6, wherein $R^1$ is hydrogen and $R^2$ methoxyethoxy.

28. A compound according to claim 6, wherein $R^1$ is hydrogen and $R^2$ methoxy.

* * * * *